(12) United States Patent
Solinsky

(10) Patent No.: US 9,186,096 B2
(45) Date of Patent: Nov. 17, 2015

(54) SYSTEM AND METHOD FOR MEASURING BALANCE AND TRACK MOTION IN MAMMALS

(71) Applicant: James C. Solinsky, Holly Springs, NC (US)

(72) Inventor: James C. Solinsky, Holly Springs, NC (US)

(*) Notice: Subject to any disclaimer, the term of this patent is extended or adjusted under 35 U.S.C. 154(b) by 1 day.

(21) Appl. No.: 13/842,030

(22) Filed: Mar. 15, 2013

(65) Prior Publication Data

US 2013/0324888 A1 Dec. 5, 2013

Related U.S. Application Data

(60) Division of application No. 12/805,496, filed on Aug. 3, 2010, now Pat. No. 8,626,472, which is a continuation-in-part of application No. 12/581,875, filed on Oct. 19, 2009, now Pat. No. 8,209,147, which is a division of application No. 11/878,319, filed on Jul. 23, 2007, now Pat. No. 7,610,166.

(60) Provisional application No. 60/832,129, filed on Jul. 21, 2006, provisional application No. 61/344,260, filed on Jun. 21, 2010, provisional application No. 61/344,026, filed on May 10, 2010, provisional application No. 61/282,527, filed on Feb. 25, 2010.

(51) Int. Cl.
*G06F 15/00* (2006.01)
*A61B 5/11* (2006.01)
*A61B 5/22* (2006.01)
*A61B 5/00* (2006.01)
*G01C 22/00* (2006.01)

(52) U.S. Cl.
CPC .............. *A61B 5/112* (2013.01); *A61B 5/1114* (2013.01); *A61B 5/1122* (2013.01); *A61B 5/224* (2013.01); *A61B 5/6831* (2013.01); *A61B 2562/0219* (2013.01); *A61B 2562/0223* (2013.01); *G01C 22/006* (2013.01)

(58) Field of Classification Search
CPC ...... A61B 5/112; A61B 5/224; A61B 5/6831; A61B 5/1122; A61B 5/1114; G01C 22/006
USPC ........... 702/19, 160; 600/595; 607/46, 48, 49, 607/59, 72, 149, 152
See application file for complete search history.

(56) References Cited

U.S. PATENT DOCUMENTS 3,881,496 A * 5/1975 Vredenbregt et al. .......... 607/49
4,416,293 A 11/1983 Anderson et al.
(Continued)

FOREIGN PATENT DOCUMENTS

WO 2008/124481 10/2008

OTHER PUBLICATIONS

H Gray, *Anatomy of the Human Body*, www.thedora.com/anatomy; Human Body> IV.Myology> /The_Muscles_and_Fasciae_of_ the_Iliac_region.html, _Thigh.html, _Leg.html, _Ankle html, _Foot.html (1918).
(Continued)

*Primary Examiner* — Carol S Tsai
(74) *Attorney, Agent, or Firm* — Nixon & Vanderhye, P.C.

(57) ABSTRACT

An example sensor band configured for attachment to a calf of a mammal and used in measuring track and balance motion of the mammal includes one or more first sensors for sensing muscle circumferential pressure at multiple positions; one or more second sensors for sensing Earth's magnetic field; and one or more third sensors for sensing Earth's gravitational field.

5 Claims, 28 Drawing Sheets

(56) References Cited

U.S. PATENT DOCUMENTS

| | | | |
|---|---|---|---|
| 4,600,016 A | 7/1986 | Boyd et al. | |
| 4,631,676 A | 12/1986 | Pugh | |
| 4,635,932 A | 1/1987 | Dewees | |
| 4,745,930 A | 5/1988 | Confer | |
| 4,813,436 A | 3/1989 | Au | |
| 4,834,057 A | 5/1989 | McLeod, Jr. | |
| 4,969,471 A | 11/1990 | Daniel et al. | |
| 5,186,062 A | 2/1993 | Roost | |
| 5,299,454 A | 4/1994 | Fuglewicz et al. | |
| 5,311,880 A | 5/1994 | Lancaster et al. | |
| 5,474,087 A | 12/1995 | Nashner | |
| 5,511,561 A | 4/1996 | Wanderman et al. | |
| 5,613,690 A | 3/1997 | McShane et al. | |
| 5,623,944 A | 4/1997 | Nashner | |
| 5,724,265 A | 3/1998 | Hutchings | |
| 5,899,963 A | 5/1999 | Hutchings | |
| 5,952,585 A | 9/1999 | Trantzas et al. | |
| 5,955,667 A | 9/1999 | Fyfe | |
| 6,292,106 B1 | 9/2001 | Solinsky et al. | |
| 6,305,221 B1* | 10/2001 | Hutchings | 73/488 |
| 6,360,597 B1 | 3/2002 | Hubbard, Jr. | |
| 6,663,519 B2 | 12/2003 | Kuhn et al. | |
| 6,699,207 B2 | 3/2004 | Tasch et al. | |
| 6,784,826 B2 | 8/2004 | Kane et al. | |
| 6,807,826 B2 | 10/2004 | Fenton | |
| 6,813,582 B2* | 11/2004 | Levi et al. | 702/141 |
| 6,831,603 B2 | 12/2004 | Menache | |
| 6,836,744 B1 | 12/2004 | Asphahami et al. | |
| 7,233,881 B2* | 6/2007 | Kobayashi | 702/188 |
| 7,552,538 B1 | 6/2009 | Bushman et al. | |
| 7,610,166 B1 | 10/2009 | Solinsky | |
| 7,611,520 B2 | 11/2009 | Broers et al. | |
| 7,620,520 B2 | 11/2009 | Vock et al. | |
| 7,627,451 B2 | 12/2009 | Vock et al. | |
| 7,632,239 B2 | 12/2009 | Dar et al. | |
| 7,640,804 B2 | 1/2010 | Daumer et al. | |
| 7,647,196 B2 | 1/2010 | Kahn et al. | |
| 7,648,472 B2 | 1/2010 | McCarthy et al. | |
| 7,756,585 B2* | 7/2010 | Embrey et al. | 607/49 |
| 8,628,485 B2* | 1/2014 | Wilson et al. | 600/592 |
| 8,744,783 B2* | 6/2014 | Templeman | 702/44 |
| 2004/0154192 A1 | 8/2004 | Bengtsson et al. | |
| 2006/0000420 A1 | 1/2006 | Davies et al. | |
| 2006/0155386 A1 | 7/2006 | Wells et al. | |
| 2006/0195050 A1 | 8/2006 | Alwan et al. | |
| 2007/0021689 A1 | 1/2007 | Stergiou et al. | |
| 2007/0179561 A1* | 8/2007 | Embrey et al. | 607/49 |
| 2007/0229552 A1 | 10/2007 | Shih et al. | |
| 2007/0250286 A1 | 10/2007 | Duncan et al. | |
| 2007/0263001 A1* | 11/2007 | Trzecieski | 345/473 |
| 2008/0077326 A1* | 3/2008 | Funk et al. | 701/220 |
| 2008/0146580 A1* | 6/2008 | Flores et al. | 514/250 |
| 2008/0146968 A1 | 6/2008 | Hanawaka et al. | |
| 2008/0167580 A1* | 7/2008 | Avni et al. | 600/587 |
| 2008/0210477 A1* | 9/2008 | Takenaka et al. | 180/8.6 |
| 2008/0285805 A1 | 11/2008 | Luinge et al. | |
| 2008/0287832 A1* | 11/2008 | Collins et al. | 600/587 |
| 2008/0292179 A1* | 11/2008 | Busch | 382/154 |
| 2009/0124938 A1* | 5/2009 | Brunner | 600/595 |
| 2009/0198155 A1* | 8/2009 | Bonnet | 600/595 |
| 2009/0206058 A1* | 8/2009 | Iwata et al. | 216/71 |
| 2009/0260426 A1* | 10/2009 | Lieberman et al. | 73/65.01 |
| 2010/0035727 A1* | 2/2010 | Brunner | 482/8 |
| 2011/0054809 A1* | 3/2011 | Templeman | 702/44 |
| 2012/0035509 A1* | 2/2012 | Wilson et al. | 600/592 |
| 2012/0054809 A1* | 3/2012 | Chowdhury et al. | 725/93 |
| 2013/0165820 A1* | 6/2013 | Lin et al. | 600/595 |
| 2013/0166198 A1* | 6/2013 | Funk et al. | 701/446 |

OTHER PUBLICATIONS (Ibid.); Human Body> XII.Surface Anatomy and Surface Markings> surface_anatomy_of_the_lower_extremity.html (1918).

DE Hokanson, DS Sumner, DE Stirandness, "An Electrically Calibrated Plethysmograph for Direct Measurement of Limb Blood Flow," IEEE Trans Bio Eng BME22 (1) 25-29 (Jan. 1975).

WJ Freeman, *Mass Action in the Nervous System*, Academic Press, NY, NY, (1975).

N Yamazaki, H Ishida, T Kimura, M Okada, "Biomechanical analysis of primate bipedal walking by computer simulation," J of Human Evolution 8 (3) 337-349 (Mar. 1979).

JG Reid, PA Costigan, "Trunk muscle balance and muscular force," Spine 12 (8) 783-786 (Oct. 1987).

GM Shepherd, "Neurobiology," 2nd Ed, Oxford Pres, p. 286, 412 (1988). See also H Markl, "The perception of gravity and of angular acceleration in invertebrates," Handbook of Sensory Physiology 6 *Vestibular Systems*, Springer-Verlag p. 17-74 (1974).

A. Katbab, "Analysis of human torso motion with muscle actuators," Ann. Biomedical Eng., 17 (1) 17-91 (Jan. 1989).

PJ Pretorius, NT Malan, HW Huisman, PJ Laubscher, FC Eloff, FAJ deKlert, SJ van der Merwe, "The use of a continuous non-invasive blood pressure recorder to study experimental stressors," IEEE Eng in Med & Bio Soc 11th Int Conf, CE2770, p. 0128-0129 (Jun. 1989).

G Nemeth, H Ohlsen, "Moment arms of hip abductor and adductor muscles in vivo computed tomography," Clinical Biomechanics 4 (3) 133-136 (Aug. 1989).

A Urso, R Shankar, B Szabo, "Design of a High Signal to Ratio Electrical Impedance Plethysmograph," Proceed SouthEastcom, Session 11F5, p. 1100-1104 (1990).

NN Byl (also N Niles), P Sinnott, "Variations in balance and body sway in middle-aged adults: Subjects with healthy backs compared with subjects with low-back dysfunction," Spine 16 (3) 325-330 (Mar. 1991).

RJ Elble, SS Thomas, C Higgins, J Colliver, "Stride-dependent changes in gait of older people," J of Neurology 238 p. 1-5 (1991).

SI Sagatum, TI Fossen, "Lagrange Formulation of Underwater Vehicles," IEEE Conference (ISSN# 0-7803-0233), p. 1029-1034 (Aug. 1991).

GS Berns, ML Hull, HA Patterson, "Strain in the anteromedial bundle of the anterior cruciate ligament under combination loading," J Orthop Res 10 (2) 167-176 (Mar. 1992).

J Perry, *Gait Analysis: normal and pathological function*, p. 114-124, 414-421 (1992).

E Barrey, P Galloux, JP Valette, B Alvinet, R Wolter, "Stride characteristics of over ground versus treadmill locomotion in saddle horses," Acta Anatomica 146 (2-3) 90-94 (1993).

JE Bullock-Saxton, Vladimir Janda, MI Bullock, "Reflex activation of gluteal muscles in walking: An approach to restoration of muscle function for patients with lower back pain," Spine 18 (6) 704-708 (May 1993).

D Intiso, V Santilli, MG Grasso, R Rossi, I Caruso, "Rehabilitation of walking with electromyographic biofeedback in foot-drop after stroke," 25, p. 1189-1192 (1994).

V Dietz, KL Leenders, G Colombo, "Leg muscle activation during gait in Parkinson's disease: influence of body loading," ECG and Clinical Neurophysiology/EMG and Motor Control 105 (5) 400-405 (Oct. 1997).

RE Ballard, DE Watenpaugh, GA Breit, G Murphy, DC Holley, AR Hargens, "Leg intramuscular pressures during locomotion in humans," J Appl Physiol 84 p. 1976-1981 (Feb. 1998).

EM Abdel-Rahman, MS Hefzy, "3D dynamic behavior of the human knee joint under impact loading," Med Engr Physics 20 (4) 276-290 (Jun. 1998).

M Vistintin, H Barbeau, N Korner-Bitensky, NE Mayo, "A new approach to retrain gait in stroke patients through body weight support and treadmill stimulation," Stroke, 29, p. 1122-1128 (Jun. 1998).

K Hase, N Yamazaki, "Computational evolution of human bipedal walking by a neuro-musculo-skeletal model," Artificial Life Robotics, Otila Japan, 3 (3) 133-138 (Sep. 1999).

WJ Freeman, "A proposed name for aperiodic brain activity: stochastic chaos," Neural Networks 13, p. 11-13 (2000).

LY Griffin, J Agel, MJ Albohm, EA Arendt, RW Dick, WE Garrett, JG Garrick, TE Hewett, L Huston, ML Ireland, RJ Johnson, WB Kibler, S Lephart, JL Lewis, TN Lindenfield, BR Mandelbaum, P Marchak, CC Teitz, EM Wojtys, "Non-contact ACL injuries, risk factors, and prevention strategies," J Am Acad Orthop Surg 8 (3) 141-150 (May/Jun. 2000).

(56) References Cited

OTHER PUBLICATIONS

BP Boden, GS Dean, JA Feagin, WE Garrett, "Mechanisms of anterior cruciate ligament injury," Orthopedics 23 (6) 573-578 (Jun. 2000).
M Rebel, HH Paessler, "The effect of knee brace on coordination and neuronal leg muscle control: an early postoperative functional study in anterior cruciate ligament reconstructed patients," Knee, Surg, Sports Traumatol, Arthrose 9, p. 272-291 (2001).
MS Puniello, CA McGibbon, DE Krebs, "Lifting strategy and stability in strength-impaired elders," Spine 26 (7) 731-737 (Apr. 2001).
ML Kaplan, JH Heegaard, "Predictive algorithms for neuromuscular control of human locomotion," J Biomechanics 34 (8) 1077-1083 (Aug. 2001).
L Vogt, K Pfeifer, M Portscher, W Banzer, "Influences of nonspecific low back pain on 3D lumbar spine kinematics locomotion," Spine 26 (17) 1910-1919 (Sep. 2001).
YS Song, RE Debski, V Musahl, M Thomas, M Gabriel, J Gil, SL-Y Woo, "Stress distribution within the anteromedial and poster lateral bundles of ACL under anterior tibial load," U Pittsburgh MRC, Dec. 14, 2001, (http://www.ruf.rice.edu/~preors/Yuhua-Song.pdf).
S Delorme, M Lamontagne, S Tavoularis, "Kinematic measurements of snowboarder's ankles," World Congress on BioMech, Calgary Canada (2002).
AI Beutler, LW Cooper, DT Kirkendall, WE Garrett, "Electromyographic analysis of single-leg, closed chain exercises: Implications for rehabilitation after anterior cruciate ligament reconstruction," J of Athletic Training 37 (1) 13-18 (Mar. 2002).
AS Ali, KA Rowen, JF Iles, "Vestibular actions on back and lower limb muscles during postural tasks in man," J. Physiol. 546.2, p. 615-624 (Dec. 6, 2002).
FE Zajac, RR Neptune, SA Kautz, "Biomechanics and muscle coordination of human walking: Part I Introduction to concepts, power transfer, dynamics and simulations," Gait & Posture 16 (3) 215-232 (Dec. 2002).
FE Zajac, RR Neptune, SA Kautz, "Biomechanics and muscle coordination of human walking: Part II Lessons from dynamical simulations and clinical implications," Gait & Posture 17 (1) 1-17 (Feb. 2003).
A Seyfarth, H Geyer, H Herr, Swing-leg retraction: a simple control model for stable running. J of Exp. Biology 206, p. 2547-2555 (Feb. 22, 2003).
R Brill, "Motion analysis finds modern applications," Honolulu Star-Bulletin Business, *Facts of the Matter,* http://archives.starbulletin.com/2003/06/15/business/brill.html, (Jun. 15, 2003); (see also http://www.mofoxtrot.com/wilson/foxtrot.htm and http://bowlingsite.mcf.com/Movement/Hcan.html).
MG Pandy, "Simple and complex models for studying muscle function in walking," Phil. Trans. R. Soc. Lond. B 358, p. 1501-1509 (Aug. 11, 2003).
H Sjostrom, JH Allum, MG Carpenter, AL Adkin, F Honegger, T Ettlin, "Trunk sway measures of postural stability during clinical balance tests in patients with chronic whiplash injury symptoms," Spine 28 (15) 1725-1734 (Aug. 2003).
R. Allendorfer, DE Koditschek, P Holmes "Towards a factored analysis of legged locomotion models," IEEE proceedings Int. Conf Robotics & Automation, Taipei, Taiwan, p. 37-44 (Sep. 14-19, 2003).
SG McLean, AJ van den Bogert, "Development and validation of a 3-D model to predict knee joint loading during dynamic movement," Trans. of ASME 125, p. 864-874 (Dec. 2003).
YP Ivanenko, RE Popple, F Lacquaniti, "Five basic muscle activation patterns account for muscle activity during human locomotion," J Physiol 556.1, p. 267-282 (2004).
SG McLean, X Huang, A Su, AJ van den Bogert, "Sagittal plane biomechanics cannot injure the ACL during sidestep cutting," Clinical Biomechanics 19, p. 828-838 (Jun. 6, 2004).
A Lamontagne, J Fung, "Implications for speed-intensive gait training after stroke," Stroke 35 p. 3543-2548 (Nov. 2004).
P Terrier, V Turner, Y Schultz, "GPS analysis of human locomotion; further evidence for long-range correlations in stride-to-stride fluctuations," Human Movement Science 24 (1) 97-115 (2005).

GS Berns, ML Hull, HA Patterson, "Strain in the anteromedial bundle of the anterior cruciate ligament under combination loading," J of Orthopaedic Research 10 (2) 167-176 (Feb. 2005).
T Krosshaug, TE Anderson, O-E Olsen, G Myklebust, R Bahr, "Research approaches to describe the mechanisms of injuries in sport: limitations and possibilities," Br J Sports Med 39, p. 330-339 (Feb. 27, 2005).
Wininger et al., "A novel means for detection of muscular activity," Biomedical Engineering Society Annual Fall Meeting, Baltimore, MD, Oct. 10, 2005.
BJ West, N Scafetta, "A multifractal dynamic model of human gait," Fractals in Bio & Med, Birk. Basel (May 2006), p. 131-140 (2005).
TJ Withrow, LJ Huston, EM Wojtys, JA Ashton-Miller, "The relationship between quadriceps muscle force, knee flexion, and anterior cruciate ligament strain in an in vitro simulated jump landing," AOSSM $31^{st}$ Meeting, Keystone CO, (Jul. 2005); published in Am J Sports Med 34 (2) 269-274 (Feb. 2006).
VP Ivanenko, G Cappellini, RE Popple, F Lacquaniti, "Coordination of locomotion with voluntary movements in humans," J of Neuroscience 25 (31) 7238-7352 (Aug. 2005).
C Toulotte, A Thevenon, E Watelain, C Fabre, "Identifaction of healthy and elderly fallers and non-fallers by gait analysis under dual-task conditions," Clinical Rehabilitation 20 (3) 269-276 (2006).
MG Bowden, CK Balasubramanian, RR Neptune, SA Katz, "Anterior-posterior ground reaction forces as a measure of paretic leg contribution in hemiparetic walking," Stroke 37 p. 872-876 (Mar. 2006).
G Brambilla, J Buchi, AJ Ijspeert, "Adaptive four legged locomotion control based on nonlinear dynamical systems," Proceedings $9^{th}$ Int Conf on the Simulation of Adaptive Behavior (SAB 2006), p. 1-12 (Preprint May 2006).
H Geyer, A Seyfarth, R Blickhan, "Compliant leg behavior explains basic dynamics of walking and running," Royal Soc. Proceedings B, p. 1-7 (Jun. 2006).
LL Nuffer, PM Medvick, HP Foote, JC Solinsky, "Multi-/Hyper-Spectral Image Enhancement for Biological Cell Analysis," Cytometry, Part A 69A (8) 897-903 (Aug. 1, 2006).
W Wang, R Crompton, A Minetti, M Gunther, W Sellers, R Abboud, RM Alexander, "A muscle-driven model of human walking and estimate of metabolic expenditure on muscles," J of Biomechanics 39 (1) S36 (Aug. 25, 2006).
SD Glassman, K Bridwell, JR Dimar, W Horton, S Berven, F Schwab, "The impact of positive sagittal balance in adult spinal deformity," Spine 30 (18) 2024-2029 (Sep. 2006).
A Hreljac, RT Imamura, RF Escamilla, WB Edwards, "When does a gait transition occur during human locomotion," J of Sports Science and Med 6, p. 36-43 (2007).
N Scafetta, RE Moon, BJ West, "Fractal response of physiological signals to stress conditions, environmental changes, and neurodegenerative diseases," Complexity, Wiley Interscience, 12 (5) 12-17 (2007).
S Mallau, G Bollini, JL Jouve, C Assiante, "Locomotor skills and balance strategies in adolescents idiopathic scoliosis," Spine 32 (1) E14-E22 (Jan. 2007).
U van Daele, F Hagman, S Truijen, P Vorlat, B van Gheluwe, P Vaes, "Differences in balance strategies between nonspecific chronic low back pain patients and healthy control subjects during unstable sitting," Spine 34 (11) 1233-1238 (May 2007).
AA Biewener, MA Daley, "Unsteady motion: integrating muscle function with the whole body dynamics and neuromuscular control," J Exp Biology 210, p. 2949-2960 (Jun. 12, 2007).
D Saha, S Gard, S Fatone, S Ondra, "The effect of trunk-flexed postures on balance and metabolic energy expenditure during standing," Biomechanics 32 (15) 1605-1611 (Jul. 2007).
G Scivoletto, A Romanelli, A Mariotti, D Marinucci, F Tamburella, A Mammone, E Cosentino, S Sterzi, M Molinari, "Clinical factors that affect walking level and performance in chronic spinal cord lesion patients," Spine 33 (3) 259-264 (Feb. 2008).
KJ Parsons, T Pafau, AM Wilson, "High-speed gallop locomotion in the thoroughbred racehorse I. The effect of incline on stride parameters," J of Exp Biology 211 p. 935-944 (Feb. 2008). See also, K Phillips (<kathryn@biologists.com>), "How horses gallop up hill," http://jeb.biologists.org/cgi/content/full/211/6/ii (2008).

(56) References Cited

OTHER PUBLICATIONS

KJ Parsons, T Pafau, AM Wilson, "High-speed gallop locomotion in the thoroughbred racehorse. II. The effect of incline on center of mass movement and mechanical energy fluctuation," J of Exp Biology 211 p. 945-956 (Feb. 2008a).

CH Cheung, KH Lin, JL Wang, "Co-contraction of cervical muscles during Sagittal and coronal neck motions at different movement speeds," Eur J Appl Physiol 103 (6) 647-654 (Aug. 2008).

MA McDowell, CD Fryar, CL Ogden, KM Flegal, "Anthropometric Reference Data for Children and Adults, 2003-2006," CDC National Health Statistics Reports (10) (Oct. 22, 2008).

RR Neptune, DJ Clark, SA Kautz, "Modular control of human walking: a simulation study," J Biomechanics 42 (9) 1282-1287 (2009).

CK Balasubramanian, RR Neptune, SA Kautz, "Variability in spatiotemporal step characteristics and its relationship to walking performance post stroke," Gait & Posture 29, p. 408-414 (2009).

RR Neptune, CP McGowan, SA Kautz, "Forward Dynamics Simulations Provide Insight Into Muscle Mechanical Work During Human Locomotion," Exercise Sports Sci Rev 37 (4) 203-210 (2009b).

DR Wilderman, SE Ross, DA Padua, "Thigh muscle activity, knee motion, and impact force during side-step pivoting, in agility trained female basketball players," J Athletic Training 44 (1) 14-25 (Feb. 2009).

B Chuckpaiwong, JA Nunley, RM Queen, "Correlation between static foot type measurements and clinical assessments," Foot Ankle Int. 30 (3) 205-212 (Mar. 2009).

AP Claus, JA Hides, GL Moseley, PW Hodges, "Different ways to balance the spine: Subtle changes in Sagittal spinal curves affect regional muscle activity," Spine 34 (6) E208-E214 (Mar. 2009).

KM Brown, DE Bursey, LJ Arneson, CA Andrews, PM Ludewig, WM Glasoe, "Consideration for digitization precision when building coordinate axes for a foot model," J BioMech 42 (19) 1263-1269 (Apr. 2009).

N Scafetta, D Marchi, BJ West, "Understanding the complexity of human gait dynamics," Chaos 19 (026108), p. 1-20 (May 2009).

S Gillain, E Warzee, F Lekeu, V Wojtasik, D Maquet, JL Croisier, E Salmon, J Petermans, "The value of instrumental gait analysis in the elderly healthy, MCI or Alzheimer's disease subjects and a comparison with other clinical tests used in single and dual-task conditions," Ann Phys Rehabil Med 52 (6) 453-474 (May 2009).

C Enzinger, H Dawes, H Johansen-Berg, D Wade, M Bogdanovic, J Collett, C Guy, U Kischka, S Ropele, F Frazekas, PM Matthews, "Brain activity changes associated with treadmill training after stroke," Stroke 40 p. 2460-2467 (Jul. 2009).

J Chappell, D Kirkendall, C Giuliani, B Yu, WE Garrett, "Kinematics and EMG landing preparation in vertical stop-jumps: Risks for non-contact ACL injury," AJSM_20060510_BYU.doc, Preprint (received Dec. 2009).

WE Garrett, B Yu, "Chapter 10: Congruence between existing prevention programs and research on risk factors and mechanisms of non-contact ACL injury," Chapter_10_Injury_mechanism_Risk_Factors_training_Program.doc, Preprint (received Dec. 2009).

WE Garrett, B Yu, "Mechanisms of Non-Contact ACL Injuries," Garrett ACL mechanism.doc, Preprint (received Dec. 2009b).

"Tri-Axis Inertial Sensor with Magnetometer ADIS16405," Analog Devices, Dec. 31, 2009.

RM Kiss, "Comparison between kinematic and ground reaction force techniques for determining gait events during treadmill walking at different speeds," Med Eng and Physics (in press Mar. 2010).

CB Beaman, CL Peterson, RR Neptune, SA Kautz, "Differences in self-selected and fast-comfortable walking in post-stroke hemiparetic persons," Gait & Posture 31 311-316 (2010).

International Search Report for PCT/US2011/000351 dated Nov. 14, 2011.

Written Opinion of the International Searching Authority for PCT/US2011/000351, dated Nov. 14, 2011.

Supplementary European Search Report mailed Apr. 2, 2015 in counterpart European Patent Application No. 11747820.6.

L Olson, http://olympics.fanhouse.com/2010/02/17/star-crossed-in-snowboard-cross/ (2010).

Q-angle1 http://www.healthexpertadvice.org/medical_dictionary/index.php?1=Q (2010).

Q-angle2 http://nbata.com/EducationResearch/GlossaryofTerms/Knee/tabid/1619/Default.aspx (2010).

Q-angle3 http://www.womens-weight-training-programs.com/weighttrainingterms.html (2010).

Energy1 http://en.wikipedia.org/wiki/Kinetic_energy (2010).

Energy2 http://en.wikipedia.org/wiki/Principle_of_least_action (2010).

Answers1 http://www.answers.com/topis/lower-limb (2010).

Answers2 http://www.answers.com/topic/lower-limb#Muscles (2010).

Gray432 http://en.wikipedia.org/wiki/File:Gray432_color.png (2010).

Gray440 http://en.wikipedia.org/wiki/File:Gray440_color.png (2010).

Anatomy http://fitstep.com/Advanced/Anatomy (2010).

Anatomy2 http://en.wikipedia.org/wiki/Anatomical_terms_of_motion (2010).

Biosyn Systems http://biosynsystems.com (2010).

Mathiyakom http://www.usc.edu/dept/LAS/kinesiology/exsc301/LabManual/Introduction.pdf (2010).

Locomotion http://www.univie.ac.at/cga/courses/be522/ts.html (2010).

Stride http://moon.ouhsc.edu/dthompso/gait/knmatics/stride.htm (2010).

McNicholas http://www.mcnicholaskneeclinic.co.uk/pdfs/aclreconstruction.pdf (2010).

Performance_Corps http://www.performancecorps.com/Performance_Corps/Articles.html (2010).

Polhemus http://www.polhemus.com/polhemus_editor/assets/USOCWeightLiftingElbow.pdf (2010).

Polhemus2 http://www.polhemus.com/?page=Motion_Case_Studies_AMM (2010).

Automatics http://automaticswingtrainer.com/ (2010).

Ascension-tech http://ascension-tech.com (2010).

Baker http://www.brainandspinalcord.org/blog/2010/01/21/physical-exercise-a-panacea-for-body-and-brain/ (2010).

SOAR http://www.soarmedical.com/ (2010).

Extended European Search Report mailed Aug. 25, 2015 in counterpart European Patent Application No. 11747820.6.

* cited by examiner

3D Parametric Amplifier- Inverted, Compliant Pendulum
(Mass M, Inertia I, Gravity G, Leg Force A, Mag Orientation B)

Figure 6A — Running Locomotion (Changing Angular Momentum)

SYSTEM AND METHOD FOR MEASURING BALANCE AND TRACK MOTION IN MAMMALS

CROSS-REFERENCE TO RELATED APPLICATIONS

This application is a divisional of application Ser. No. 12/805,496, filed Aug. 3, 2010, now U.S. Pat. No. 8,626,472, which is a continuation-in-part of application Ser. No. 12/581,875, filed Oct. 19, 2009, now U.S. Pat. No. 8,209,147, which is a divisional of application Ser. No. 11/878,319, filed Jul. 23, 2007, now U.S. Pat. No. 7,610,166, which claims the benefit of provisional application No. 60/832,129, filed Jul. 21, 2006. The contents of each of these applications are incorporated herein in their entirety.

Application Ser. No. 12/805,496 also claims the benefit of provisional application No. 61/344,260, filed Jun. 21, 2010; provisional application No. 61/344,026, filed May 10, 2010; and provisional application No. 61/282,527, filed Feb. 25, 2010. The contents of each of these applications are incorporated herein in their entirety.

BACKGROUND AND SUMMARY

This application describes example systems and methods for placing onto a mammal's lower body, leg and thigh limbs, a set of paired bands to measure the lower body locomotion (for bipedalism, upright locomotion) and, if desired, additional arm strapped forearm and arm paired bands on the upper body (for complex motion, crawling, and in other applications, or four calf limb quadrupedalism locomotion). Each band contains multiple MEMs force sensors that measure muscle circumferential pressure at multiple positions, along with Earth's magnetic and gravitational fields. On-band data processing and networked, intra-band RF connectivity from multiple limbs, can be used to produce simple, energy-optimized, least-action metrics of mammal locomotion of two, interrelated functions defined as 1) Track, being a walking, running or other dynamic, from forward footpath creation over firm surfaces such as the ground, water-floats, or snow and ice, and 2) Balance, being required to efficiently move the lower body and/or upper body under Track. These technology metrics include assessment of locomotion related neurological functionality of body, limbs, and muscle disorders.

Details of Track differences in maintaining Balance are related to other physiological disorders, including detecting mental precursors, such as for fall-down behavior. An example system can be worn by many simultaneously and uniquely identified users, with metrics and location of each user being displayed on a laptop through additional RF connectivity, such as in recreational and professional sports. The system's on-band data processing units using battery supplied power, integrate the sensing to determine kinetic and potential energy of the body locomotion over time in a method that integrates out the aperiodic motion of the upper body and extended appendages, about center of mass (ACM), and uses the residual motion to measure the periodic center of mass (CM) locomotion from a known point.

The example systems and methods are self-calibrating, using calibration data collected when standing and jumping, at positions facing compass points. A GPS system can be incorporated for continuous motion measurement, to be used for calibration of the locomotion when GPS satellite data is available, and to establish the initiation geolocation point when beginning operation in GPS-denied regions for navigation, or to relatively geolocate multiple players in sport activities.

The body movement data, when combined with the band pressure and gravity data, removes the effects of the aperiodic, nonlinear locomotion, and leaves the residual movement for determining Track and Balance through a Euler-Lagrangian representation of the Equations of Motion.

The example systems and methods can be embodied for many applications (including the use of metric feedback for improved Balance and Track optimization), such as for human and non-human (e.g., horse) sports trainers, elder health care providers, and physical therapists for prevention and recovery from injuries of the back, knee, spine, and brain, such as from stroke, Alzheimer and Parkinson diseases, and dementia, as well as for other uses in mammal navigation and location purposes.

BRIEF DESCRIPTION OF THE DRAWINGS

This patent or application file contains at least one drawing executed in color. Copies of this patent or patent application publication with color drawing(s) will be provided by the Office upon request and payment of the necessary fees.

FIGS. 6A to 6E show combined model elements of stiff and compliant locomotion w/data.

GLOSSARY

Figure 1:
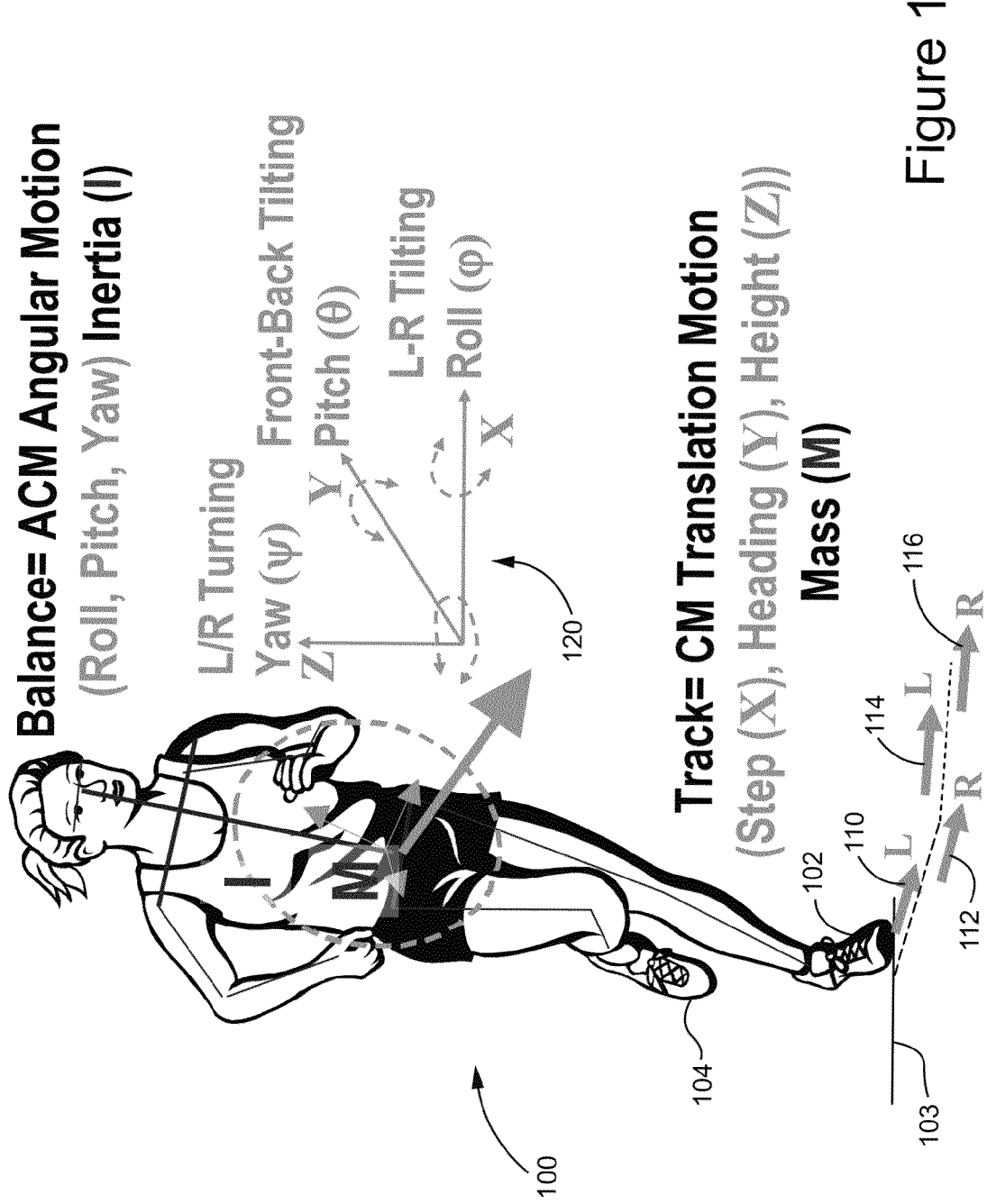
FIG. 1 shows modeled mammal ACM and CM Track and Balance locomotion axes.

A—Vector mechanical force from along limb locomotion foot thrusts
a—Acceleration of mass (M) from foot thrust force A; a=A/M
ACL—Anterior Cruciate Ligament
ACM—About Center of Mass (as measurements of jointed limb mass locations moving in angular dynamic motion to a relatively net zero gravitational energy expenditure)
AMB—Anterior-medial bundle
B—Vector magnetic force from Earth's magnetic field defining angular limb orientation
CM—Center of Mass (as measurements of forces to central mass made along limbs through joints)
CCW—Counter Clockwise
CW—Clockwise
DOF—Degree of Freedom
EMG—Electromyogram
Figure Labeling:
UL—Upper left
UR—Upper right
LL—Lower left
LR—Lower right
G—Vector gravitational force from Earth's gravity field defining dynamic CM energy
g—Acceleration of mass (M) in gravitational force G; g=G/M
g—Representation of mass as a weight force in the Earth's gravitational force.
Gait Metrics:
Stance phase—when one leg is supporting the body weight with the foot on the ground
Swing phase—when one leg is moving to a new position to support body weight
TO—Takeoff, toe off, etc., referring to the toe leaving the surface as an execution of that leg's beginning the swing phase in the gait.
TD—Touchdown, heel strike (or foot strike in small angle), etc., referring to the toe arriving on the surface as an execution of that leg's beginning the stance phase in the gait (definition of initiating the gait cycle).
Step—Forward motion of the leg moving the toe off the ground (TO) to the opposite leg dropping the heel to the touchdown (TD) to the ground as a step-length between two foot steps
Stride—One L and one R foot step taken in sequence (in length as two step-lengths, being the distance between sequential TO events from the same foot)
Gait cycle—cycle of one stride; in units of stride-length or time (stride-time)
Cadence—Step rate in steps/min, defining the stride-length as (120*speed)/cadence
Speed—Distance per time period (cadence*stride-length)/120 (m/sec)
Step-length—linear (diagonal) distance between footsteps
Stride-length—linear distance between L/R sequential footsteps
Walking base—perpendicular distance between footsteps
SRV—Stride-to-stride rate variability
L—Left (e.g., leg motion)
R—Right (e.g., leg motion)
GRF—Ground Reaction Force
RH—Right hand rotational motion model to a linear axis
Linear Motion:
x—X-axis translational distance vector (X-axis surging forward of step distance)
y—Y-axis translational distance vector (Y-axis swaying as angular change from X for heading)
z—Z-axis translational distance vector (Z-axis heaving as vertical changes of height, h)
h—Height above support surface (e.g., ground, h=Z-axis)
dx—Differential X-axis vector element
dt—Differential element in time describing motion dynamics, as a short time interval
v—Linear velocity vector in X (dx/dt)
M—Total body mass at CM location; M=∫dm(r)
dm(r)—differential distributed mass element at vector location r from the CM
Rotational Motion:
$\phi$-Tait Brian angle about X-axis (roll, also uses $\alpha$-Euler)
$\theta$—Tait Brian angle about Y-axis (pitch, also uses $\beta$-Euler)
$\psi$—Tait Brian angle about Z-axis (yaw, also uses $\gamma$-Euler)
r—Radial translational radius vector
dr—Differential r-radial axis vector
$\tau$—Torque force of angular motion, which also is a form of mechanical work normal to r
$\omega$—Angular velocity vector defining angular motion
I—Moment of mass inertia (inertial angular mass distribution in ACM location); I=∫$r^2$ dm(r), as a 2D tensor representation
Band Components:
MSM—Multi-sensor Module component of band
r—Index number on MSM board for band sensors
R—linear distance on band from buckle used to measure force field derivatives, as sensor data differences
θ—Angle location along the circumference of the band for each MSM placement relative to the elliptical, bone centered foci for mapping of the muscle cross-sections for thigh and calf midsections.
m—Index for band number to be used in RF connectivity correlation analysis
FSR—Force sensitive resistor for muscle pressure (P) MSM measurements
$P_r$—Pressure of each $r^{th}$ MSM FSR
$\Delta P^r$—Difference in pressure between sequential MSMs (dP/dR)
$P_R$—Average of band MSM pressures
$A_p$—Area of pressure sensitive resistor sensor (converts pressure sensing to force, which includes any area transitioning involving a mechanical coupling of the measurement, e.g., using a "puck" or force "amplifier")

Band Computational Techniques:

Coordinate Representation:
- q—Generalized coordinate system for the Lagrangian EOM motion representation.
- $\Im$—Functional (nonlinear) mapping of sensing coordinates into computational coordinates, or in mapping pressure to force measurements Signal Processing:
- PCA—Principal component analysis
- ICA—Independent component analysis
- HOS—Higher-ordered statistics, referring to statistics with correlations beyond the second order of Gaussian statistics, such as with a representation in Gram-Charlier excess probability density functions (PDF) and cumulative distribution functions (CDF)
- HOS Cumulants—non-zero correlation beyond second order, e.g., for fourth order HOS of mean-$\mu$, variance-$\sigma^2$, skewness-S, excess kurtosis-K
- IMP—Inter Muscle Pressure
- $TF_{dr}$—Transfer function in Fourier analysis of coherent noise removal Metrics:
- W—Work as the mechanical dynamic of the spatial path integration of forces (G, A); $W=\int A \cdot dh$
- E—Energy as the integration of Power (P) over short time intervals (dt); $E=\int P dt$
- P—Power as rate of energy expenditure (dE/dt)
- PE—Potential Energy
- KE—Kinetic Energy
- L—Lagrangian Energy (KE-PE)
- S—Action is the integration of the energy (E) over time intervals, and for the Lagrangian energy, this is a goal for minimization in locomotion metrics of Track and Balance during gait cycles; i.e., $S=\int L dt$ is minimized
- EL—Euler-Lagrange Equations of Motion (EOM)

DETAILED DESCRIPTION OF EXAMPLE EMBODIMENTS

The example systems and methods relate to the automation of the general field of determining mammal locomotion metrics, from a simple viewpoint when muscular-driven support members propel the body, being that of linear momentum relative to the ground or other surfaces, defined as Track-movement, and being that of angular momentum relative to the body, defined as Balance-movement. This is uniquely different from gait analysis because these measurements are made by totally self-contained, strap-on-bands that can be worn in any type of locomotion activity including sports, and also by other mammals, such as horses, and does not require human analysis of any collected data. The example systems and methods incorporate band sensors worn on body limbs with networked RF connectivity to compute, using related sensor data, muscular motion across multiple band links and within a group of interacting sports players or racing mammals.

Because this real-time measurement and monitoring is being made with a very high fidelity, and is made outside the laboratory in the world of more natural activities, the Track and Balance motion viewpoint allows the measured information to be used in physical and mental health assessment. The metrics are in a database format for easy long-term trend analysis and population demographic characterization. Examples include use in sports training, in therapeutic injury-recovery monitoring (e.g., from either a predicted potential-injury diagnosis, or from post-disorders and post-injury repair assessment), and in general health care and treatment of the elderly.

Real-time Track and Balance monitoring, with inexpensive components providing feedback to the individual, can also lead to mental changes for improved physical performance and mental stability. The system complements many of the laboratory based gait analysis techniques using treadmills and photographic or video analysis of body motion. By ignoring the detailed biometric models of individual muscle contributions to locomotion, it uniquely measures a subset of individual muscle action components and limb locations during interaction tasks, at a very fine detail to integrate local muscle's neural oscillator controlling functionality of Balance, with a global, brain controlling functionality of Track.

Mammal locomotion is the process of self-powered movement, through muscular tension against bone stiffness that creates singular, two point limb-contacts with the ground by a foot (e.g., a "footprint" path of heel-strike or touchdown (TD) to toe-off (TO) defined contact periods, depending upon walking and running activities), using a complex pattern of continuous periodic and aperiodic activity, which leads to forward motion. Human's walk forward as if falling, but recover balance in the landing and sequence to the next step, similar in part to riding a Segway® 2-wheel tracking vehicle that falls forward if not kept in balance by the driver's balance. The human muscular functions involve a pre-planned control, based on a perceptual awareness of dynamic surroundings and limb locations, and current goal driven action-requirements. The motion changes with the speed of advancement and the number of "legs" being utilized, and is generally classified as gait analysis, because the legs lift the feet and place them at a forward location as a sequence of steps along a "track." Failures in reacting to unforeseen changes in this locomotion advancement, especially when foot placement dramatically changes as a step-and-cut running motion, can lead to physical injury. A problem is to determine for a variety of applications, specific biomechanical and neurological disorders that can be measured in a more representative activity and with an automated analysis approach, than currently is practiced through gait laboratory measurements and data analysis being made by gait professionals. Here, the relevant information, e.g., as shown in FIG. 1, would be quite useful if made through a simpler measurement, and metrics were automatically computed in real-time, where information could be made available for not only diagnosis and assessment, but also for immediate training feedback during the occurrence of the physical locomotion events. The metrics can also include derived common gait and knee angle assessment parameters.

The following description demonstrates, among other things, the complexity of the prior art, which is why current gait analysis uses intensive human analysis of clinical recordings with no automated analysis, and hence a problem solution requires a simplification of biomechanical modeling metrics, used in diagnosis and assessment from current gait analysis, in order to have a more general utility. This simplification, described next, suppresses much of the biomechanics of locomotion, and injects new concepts involving other neural function beyond simple brain control functions of muscles, in order to develop simple methods for identifying locomotion and brain/neural control disorders.

Prior techniques in gait analysis measure force plate data from a force plate in contact with the heel to determine heel strikes. The systems and methods described herein do not require such measurements. Instead, heel strikes can be measured by processing, for example, pressure measurement of the muscle and changes in location. Thus, the disclosed systems and methods move away from the traditional analysis of determining heel strikes. Consequently, the systems and methods described herein use, for example, the muscles to determine the "cycle."

Among other things, this advantageously allows these systems and methods to be used in situations in which, for example, the heel does not strike first (e.g., the toes strike or impact before the heel) or there is no heel strike (e.g., a surfer "pumping" a surf board). Thus, there is no requirement of measuring heel strikes.

Paddleball Analogy for Human Locomotion

FIG. 1 illustrates a physical model of Balance and Track. In FIG. 1, the body 100 is moving along with one foot 102 on the ground (schematically shown at 103) on Track 110 and the other foot 104 off the ground in the swing phase. At the completion of this swing phase, foot 104 gets placed down on the ground on the next Track 112.

Figure 2:
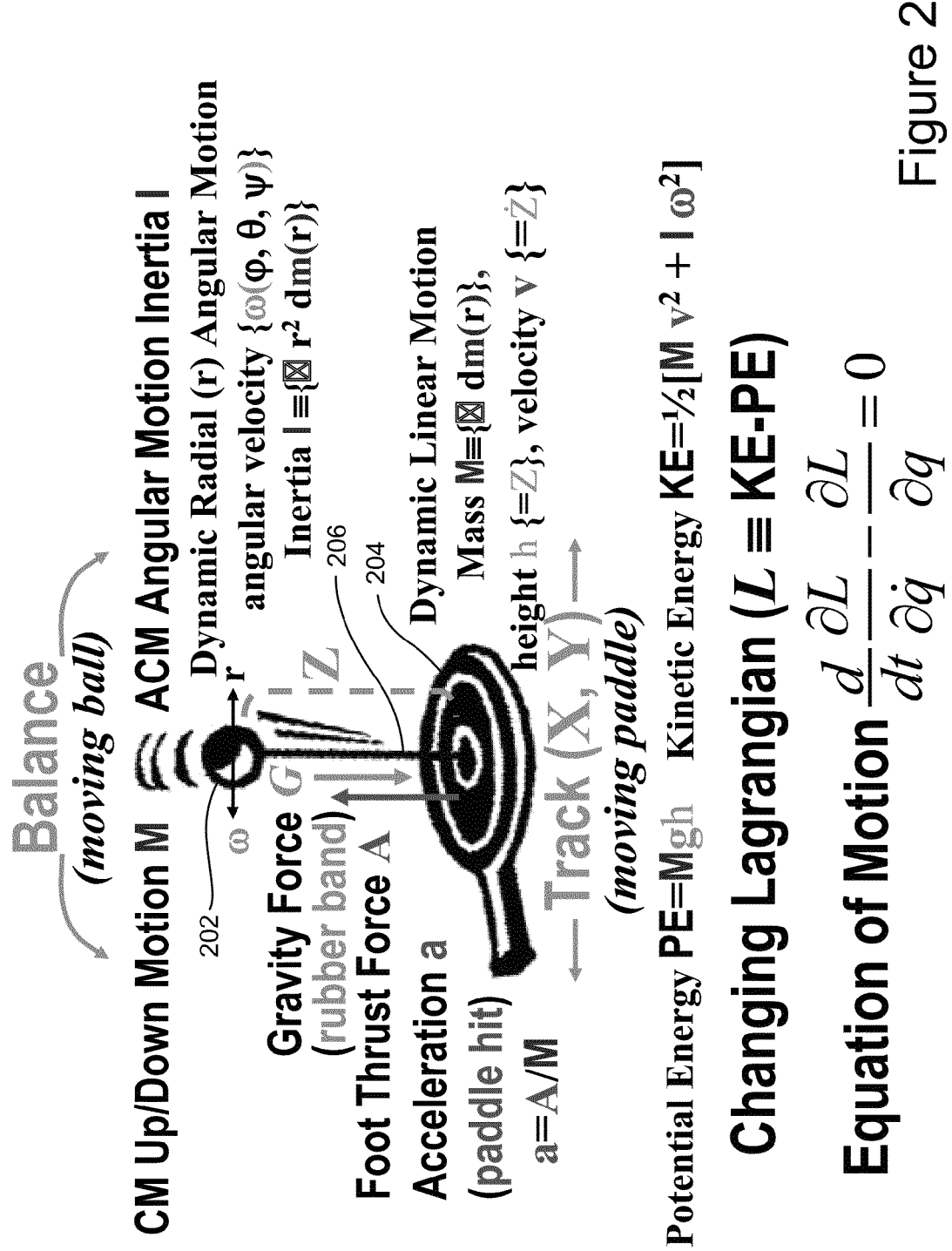
FIG. 2 shows an analogy of FIG. 1 motion using a toy paddleball representation.

FIG. 1 shows human locomotion actions with a toy paddleball analogy being shown in FIG. 2. FIG. 1 defines Track and Balance locomotion metric representations for the foot placement on a firm surface, as that of tracing out a sequence of footfalls along a changing track for the body weight (as mass M, being the sum of all mass elements, dm(r) at vector location r), shown in the figure at the body center to a gravitational vector force G (see FIG. 3, with a projected forward motion vector in coordinates X, Y, Z). This motion continuously sweeps out a six degree of freedom (DOF), "rigid body" parametric as an up and down center of mass (CM) motion like the ball in FIG. 2, being paddled up by the foot vector force thrusts, A, made to the 'ground,' and then with the 'gravitational' forces of the rubber band, G, pulling the ball back down to the 'ground' of the paddle.

The Track is in linear orthogonal dimensions as (X, Y, Z), with the linear inertial momentum energy coming from the periodic motion of the body CM moving up/down and forward from foot thrust forces A in:

1) step forward motion (X surging), as a 'diagonal' sequence of a left-to-right and right-to left (L/R, R/L) stance step set, through each leg stance placement, during opposite-leg swinging motion, as labeled in FIG. 1 with "L" and "R" for each "footprint" step in front of the runner's Track,
2) heading (Y swaying, as angular change away from X, which changes the heading angle from a Y contribution, making the footprint tracks 114 and 116 change in relative angle to the first two tracks 110 and 112 shown in FIG. 1) of forward motion, and
3) height (Z heaving) changes in vertical motion.

The height and step motion combines as a parabolic CM half-period, of a periodic cyclic motion, with the L/R transition being the heading motion change from the changed foot angle placement. These steps start at heel-strike stance, by defining a step-length of forward momentum, and end with the toe-off of the swing, by defining a foot thrust of angular momentum, and for the case of the same foot repeating, this is a two step, gait stride-length (here the perpendicular distance between sequential foot steps is the walking base).

FIG. 1 also shows the same 6-DOF upper body gyration motion, to swing the lower body legs as in standard Euler angles ($\alpha$, $\beta$, $\gamma$), but here in a Tait-Brian rigid body angle formulation ($\phi$, $\theta$, $\psi$) (as shown at 120 in FIG. 1), where the linear axis is body centered, as an angular motion description for the ball in FIG. 2, moving freely from left-to-right above the paddle (ball spin-motion as yaw is not shown).

The Balance is in an angular, about center of mass (ACM) motion creating changing angular inertial momentum energy in:

4) roll (Left/Right tilting side-to-side, RH angle on X as $\phi$),
5) pitch (Forward/Backward tilting, RH angle on Y as $\theta$), and
6) yaw (Left/Right turning, RH angle on Z as $\psi$)

as shown at 120 in FIG. 1.

Balance is not as a linear mass motion, but is an angular mass motion, with a moment of inertia, I, shown in FIG. 1 as the dashed elliptical region. Here, I computed from the squared radial (r) distance product, with the mass components dm(r), at r locations, summed over all mass elements, becoming a 2D tensor representation. This creates angular momentum from the aperiodic motion of the inertial mass elements, arising from the twisting spine moving the pelvis, hips, shoulders, head, and combined radial distance changes to mass, by the limb angle changes from the calf and thigh knee-joint angle, and from the forearm and arm elbow-joint angle.

Figure 3:
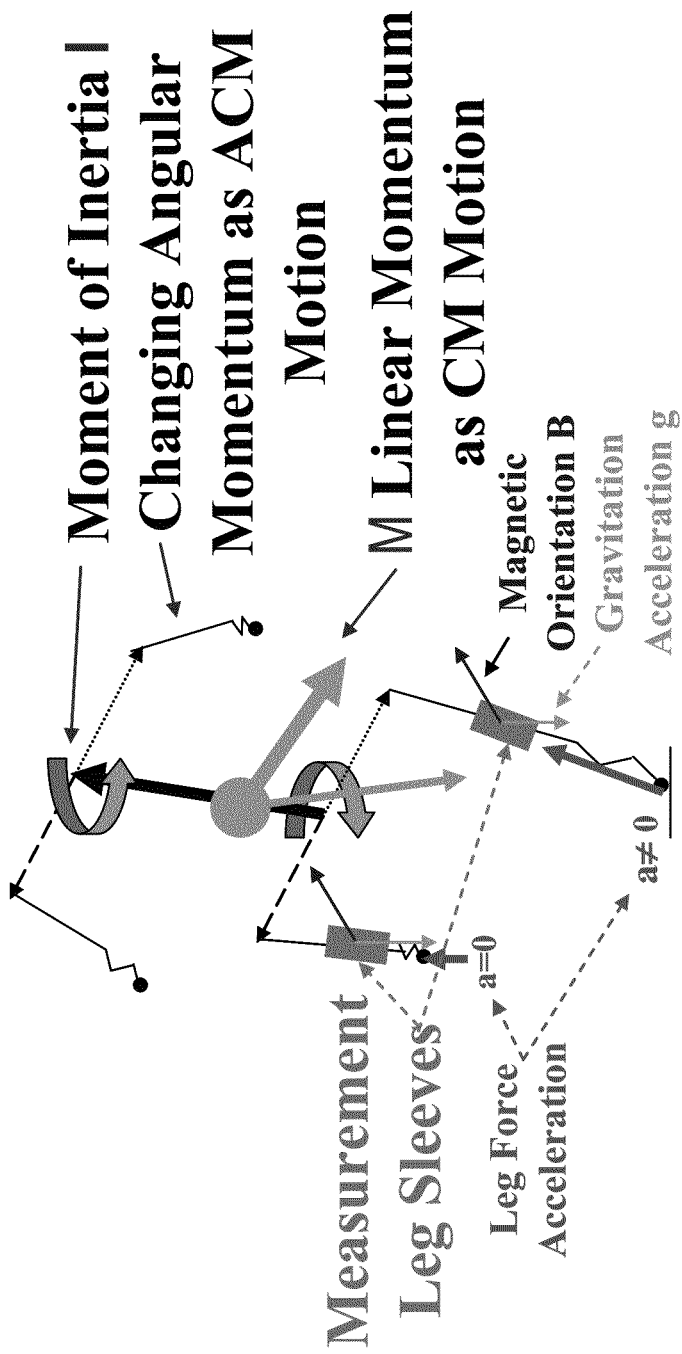
FIG. 3 shows body motion sensing as leg sensors, to measure leg thrust acceleration (a), within the Earth's gravitational acceleration (g) and magnetic field (B) orientation.

Here, the body is modeled in FIG. 3, simply as a twisting and turning, synchronized motion in angular momentum, driving an inverted pendulum swinging the body mass M through gait steps, in a parametric amplifier description (e.g., a parametric amplifier is what a child does to increase the height, while swinging on a swing set). The thigh motion of knee lifting and calf thrusting on/off foot placement, as a compliant component of tendon, muscle, and bone, yields forward locomotion as Track, and the angular momentum is related to Balance.

More specifically, when a child swings on a swing, he/she pulls on the chains/ropes from which the seat is suspended and to lift his/her body up a little bit. This pumps in energy so that the child can swing higher and higher. This is essentially the same concept, which is illustrated in FIG. 3 with respect to gyration of a person's limbs. If done synchronously, motions of shoulders, arms, head, etc. and the twisting of spine pump energy into the lower body, which is then translated into foot thrust for moving the person forward. The pumping in of energy in this manner relates to a mental construct that allows all of a person's limbs to be synchronized for a particular purpose (e.g., walking, running, swinging a golf club or tennis racket, etc.). The parametric amplifier schematically shown in FIG. 3 illustrates that dynamic oscillation parameters of the shoulders, arms, head, spine through the gait phases, can be changed to pump energy into foot thrust. As will be discussed in greater detail below, one of the new features of the systems and methods described herein is including the upper body gyrations into the analysis. Specifically, the systems and methods make measurements using leg bands (e.g., around the calf and thigh) to get full body gyration dynamics.

One can see these two body dynamic Track and Balance functions active in sports, such as in the 2010 Canadian Winter Olympics in BC, where Lindsey Jacobellis, the favored winner for the snowboard cross, followed Maelle Ricker over the first jump in an airborne ballet, where Lindsey made an airborne correction to her Balance in order to avoid a collision with Maelle, which then upset her Track when she returned to the snow, and she wiped out to not even finish the race (Olson 2010). Similar "accidents" occurred in the downhill slalom race, where racers would lean onto the inside ski to round a gate, and in order to continue into the next gate track, they would shift their weight to the other ski, but because of failure in trying also to bring the previous ski back down to the snow, in time to regain Balance for tracking before the next gate, they also wiped out from the race.

An unusual locomotion process governs these sports actions of shifting between angular momentum and linear momentum, which is not really an engineering miracle of the human body. Rather, it is a combination of the biomechanics of the body muscle locomotion, being driven by a high level of the brain's functional cognition-requests, combined with a low level of local muscle actions, driven by neural oscillator firings, which is self governing. The action is not really reproducible, but is more regular in an aperiodic functionality: i.e., multiple components contribute to the end action, but not in a regular manner, and thus, the Olympian has learned how to train these lower level muscle functions to interact with the sensed actions that align Track and Balance for an end goal. This is similar to the auto mechanic listening to the 'sound' of a car engine, with all of the explosions from sparkplug firings, gear turnings, muffler sounds, and body shakes making an overall humming sound, thus, becoming a global indication of engine 'health.' However, this identification is made not by directly defining 'correctness' as being related to the mechanical details of the periodic crankshaft rotations and the aperiodic engine reactions to the impulsive piston forces, but rather as a symphony of synchronized aperiodic components in phase-locked, synchronized interaction producing acoustic energy.

Hence, the complexity of understanding human locomotion as a collection of many components interacting together, is similar to that of a car engine's interacting components, and identifies a physical mathematical construct of the "Many Bodied Problem," i.e., describing many (as in 10-100), simultaneous force-mass interactions. In astrophysics, this can be a collection of planets moving with gravitational forces around the sun, where a complex circular motion pattern exists that is very different in detail from simple ellipses, because each component motion affects all of the other component's motion. Thus, in a similar manner, the locomotion of the limbs is more complex than simple singular muscles causing limb rotation, or as an extension increasing the limb joint angles (and flexion as a decreasing of the joint angles). Automation of understanding complex motion requires an integration of component measurements for simplification.

This locomotion CM/ACM distinction, in changing the Lagrangian and its Equation of Motion (EOM), is defined in the lower section in FIG. 2, which can be further linked to the paddleball analogy. Here, one starts hitting the ball 202 downward, but with some skill, this hitting can be migrated to an upward motion to keep the ball in the air above the paddle 204, as shown in FIG. 2. From a simple physics model, one can relate concepts of limb motion dynamics to energy, work, and power, in order to describe muscle expenditure of potential energy as kinetic action (shown in FIG. 2 as a simple 1D Z-axis dynamic of height h):

1. The kinetic energy (KE) of this ball dynamic is mechanical work (W), as the vector product along a path of spatial integration (W=$\int A \cdot dh$) of the force (A) over small height lengths (dh), affecting mass inertia dynamics of linear momentum (Mv) or can be mechanical work of torque forces ($\tau$) in angular lengths (d$\theta$), affecting mass dynamics of rotational inertia I (Energy1 2010).
2. In general, energy (E) is the temporal integration (E=$\int P dt$) of power (P, as the rate of work being performed, e.g., as force times velocity (v=dZ/dt=$\dot{Z}$) or torque times angular velocity ($\omega$), here as a function of rotational angles ($\psi$, $\theta$, $\phi$), being made over small time periods (dt), such as expressed by muscle potential energy (PE) action, produced from short bursts of power.
3. The Lagrangian (L) is defined in FIG. 2 in terms of energy differences between kinetic and potential energy (L=KE−PE). Hence, because action (S) is the dynamic containment of the energy differences in time using the Lagrangian, defined as (S=$\int L dt$), in locomotion one can substitute mechanical work of mass location changes (dh, dr) with temporal mass dynamics (dt).
4. This allows one to use magnetic field vector orientation (B/B) changes sensed at the limb masses, as a mass relative position locater in spatiotemporal integrations, and to find an optimization of energy expenditure in 'correct' locomotion using the principle of least action (minimizing S), as a 'sound' of healthy locomotion.

Here in FIG. 2, ball 202 represents the body mass M, which is moving in a CM linear motion up and down in the gravitational field force G as the rubber band 206 of the toy (on the left side of FIG. 2), and each step of this inverted pendulum is where the body is vaulting over the leg, raising the entire mass center to an increased height (h) above the ground's gravitational vector force acceleration (here, as bolded character notation, g). Thus, changes in height "h" are increasing the potential energy (PE=M|g|h) of the body motion. The paddle 204 has to be moved each time, as a linear Track dynamic, to be where the ball 202 will be landing, and this motion also causes the ball to move away from the previous top position as a sideways motion, requiring a correction to when the paddle hits it again, to return the ball to the same place in the air. The paddle 204 is providing a thrust force (A), as acceleration (a=A/M) with each strike of the ball 202, sending it back up in the gravitational field, only to be brought back down, thus creating a linear momentum sequence of the ball each time it is hit, with heading changed by the direction from the foot (paddle) placement, or from changes in the forward speed (here, as the amplitude value of the up/down velocity along the h length motion). This changes the linear kinetic energy (KE=½M|v|$^2$, for total body mass M, for the forward speed vector velocity (v) of this momentum (Mv), as a Track of footfalls.

At the same time, the ball 202 can move from side to side, due to changes in the paddle position when the ball is being brought down by the ('gravitational') rubber band 206, causing a sideways motion about its center position, thus creating an angular momentum sequence of the ball 202 before it is hit again, with roll, pitch, or yaw changes in direction due from the paddle-spin (e.g., locomotion shoe-slip), as an ACM angular motion (on the right side of FIG. 2). This creates an angular velocity ($\omega$) of a mass inertia I (as an integration of the mass points, dm(r), along the angular radial distance (r), here as the normal to the height motion), which also contributes an angular kinetic KE energy (KE=½I|$\omega$|$^2$) for total mass inertia I.

An important concept in this simple, analogous representation of a Lagrangian EOM is that of Euler's definition of action (S), defined as the temporal integration (S=$\int E dt$) of the energy (E), and when combined together with the Lagrangian (Sagatum, 1991), thus becoming the Euler-Lagrange (EL) equations (EOM). In the example Track and Balance systems and methods described herein, the periodic nature of leg-stance gait cycles, when combined with the aperiodic nature of leg-swing gait cycles, allows for a spatiotemporal force integration approach in a minimized or least action principle (Energy2 2010), which creates a means of estimating Track and Balance metrics from nothing more than integration within defined cycles of the time-varying data that also is measuring spatial dynamics. This physically modeled requirement involves distinguishing periodic from aperiodic cycles in the gait analysis between stance and swing motion, because this is the Track and Balance discrimination. While typically the TD/TO temporal locations are measured in gait analysis, with a force plate or instrumented shoe, they are not specific to the physical model, which treats these impulses only through their contribution to A.

Thus, if the Track motion is perfectly linear, as a periodic cycle shifting between stance leg placements, then the ACM dynamic is also periodic with no loss of energy from aperiodic dynamics, and the ball motion above the paddle is in a symmetric Balance to Track. The Lagrangian formulation in FIG. 2 of the body dynamics, shows L as the energy difference between the KE and the PE, and it is assumed that energy efficiency in locomotion indicates balance. Thus, in mammal locomotion, ACM angular momentum must be conserved, with the entire, linearly orthogonal, forward and periodic-height motion, contributing to the KE (i.e., step-length integrated, simultaneous two leg-stepped, gait cycle). Because the PE contributions are from the cyclic gravitational motion, it is exactly balanced with the foot thrust forces of takeoff (TO) and touchdown landing (TD, or heel-strike). FIG. 2 shows this dynamic EOM as derivatives of a generalized representation for L from the moving mass-point vector coordinates (q, which can be quite different from the original modeled coordinates, when using a function $\Im$; i.e., $q=\Im\{X, Y, Z; \alpha, \beta, \gamma\}$). Further details explicitly show a dissipative force vector from 'shoe-slip' as the thrust vector $\tau$ being related to the L EOM, but with the efficient form of the PE term being on average close to a constant (e.g. set to zero; Solinsky U.S. Pat. No. 7,610,166; FIG. 3 and following therein from Eq L3). This physical description of locomotion mechanics can now be related to the energy from spatiotemporal integration of muscle pressure measurements, for use in locomotion descriptions.

Locomotion Using Lower Body Muscles

Figure 4:
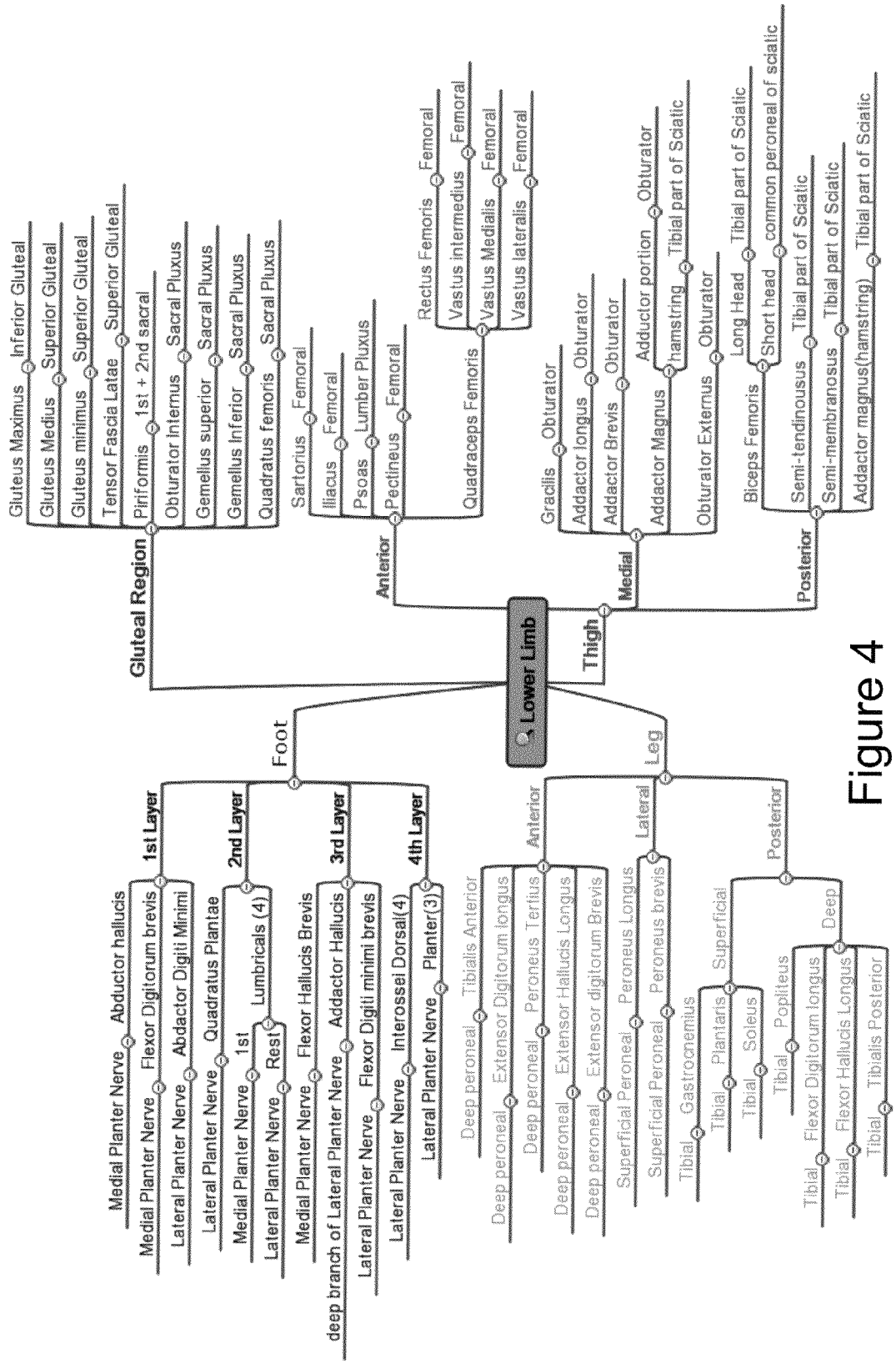
FIG. 4 shows lower limb, simplistic muscle groupings, as partial element labeling of hip (Gluteal), Thigh (without knee joint), calf (Leg without ankle joint), and Foot regions.

Because the human torso uses muscle actuators to "rock" the upright body to move forward, lower body muscle actions create the body locomotion action, shown in FIG. 3 as a parametric amplifier. During the locomotion stance phase, the muscles perform Track thrusts (extensor and abductor muscles) that sequentially push each foot off of the ground to swing the legs, which create sequential foot placements on a footpath. The lower body muscles are connected to the body at the hip, where body gyration during the swing phase (flexor muscles) maintains Balance during lifting and placing the other leg on the ground as a second footpath placement. The gyration motion of the shoulders and pelvis, shown in FIG. 3, is a form of twisting the spine and muscles extending and contracting as a further form of body dynamics in PE and KE energy transfers, but the upper body dynamics will be ignored for now in this simple model of gait locomotion using mostly the lower body components. An example of categorizing these muscles for the lower body is shown in FIG. 4 (Answers2 2010), which omits certain details (e.g., among other omitted components are the knee and ankle joints). As will be shown, numerous muscle groups are used in biomechanical modeling of locomotion, but which might be linked to a smaller set of pseudo muscle groups, as low in number to possibly being only five, using a principle component analysis (PCA) of the data, as derived from measurements of over 20 individual muscle components (Ivanenko 2004); independent component analysis (ICA) of nonlinear data might be more appropriate, due to nonlinear aperiodic dynamics being nonGaussian (Nuffer 2006).

Because direct measurement of the loads of the spine and contraction forces of contributing muscles are not always possible, nor is it possible to know what specific sensory signals occur between the muscles and the nervous system, it has been shown to be more practical to use a simulation and compare global locomotion models with experimental gait analysis. This motion can be modeled as a human torso motion with 3D muscle actuators, including actual trunk muscle balance and force measurements (Reid 1987). Along these lines, modeled locomotion stability examples have been achieved among pairs of muscles in both open and closed loops, where modeled feedback is tuned by higher centers of the nervous system (Katbab, 1989).

Furthermore, confirming this modeling of body motion can be measured using a force plate for foot placement as 3D thrust forces, along with video and photographic views of body motion planes (Perry 1992). The different types of muscles used for motion are 1) along the limb axis as rotation, and 2) transverse to the limb axis as a) extension and flexion (up/down vertical motion from the body median plane), b) sagittal to the limb axis (medial/lateral left/right sway motion from the body center plane) and c) coronal to the limb axis (frontal plane as fore/aft about the head/spine plane). This motion is made relative to the limb axis as abduction (away from the median plane) and adduction (towards the median plane).

The physical force modeling in gait locomotion uses a weight of the total body mass being supported by the lower body leg forces, which change force from a 'zero' weight at standstill (1 g), to a 110% increase of mass-weight during foot thrusting (2.1 g), being reduced to an 80% of mass-weight during foot-leg swings (1.8 g) and back to a peak of 110% for the last foot placement (2.1 g) during just 62% of the gait cycle of one stride length. There is little lateral and progressional shear force during walking. During a slow walk, these two peaks flatten out to 100% of the body weight (2 g), and during running these peaks become one peak at 220% of the body weight (3.2 g) for just the first part of the gait cycle (e.g., both feet are off the ground at one point during running; see Perry 1992). Clinically, it is important to also separate motion of the thigh from motion of the pelvis, such as when measuring the thigh position from the vertical axis to the horizon.

During this cyclic gait motion of foot placement, the hip moves as the unloaded side of the pelvis swings, in coronal motion as a small arc of adduction and abduction following the swing. During the stride of heel to toe placement, the limb moves through an arc of transverse hip motion, creating a thigh rotation. The angle between the Femur and Tibia limb axes is also useful in the locomotion analysis, and is related to body training and knee injury reduction e.g., it is important in anterior cruciate ligament (ACL) analysis to also measure the knee Q-angle. The Q-angle can be defined for a number of locomotion practices, such as being the angle formed by lines representing the pull of the quadriceps muscle and the axis of the patellar tendon (Q-angle1, 2010), or the normal angle of quadriceps relative to the patella and is 10 degrees for males (Q-angle2, 2010), or the angle at which the femur (upper leg bone) meets the tibia (lower leg bone), where it is linked to a greater incidence of sports injuries in woman, caused by a wider pelvis than in men (Q-angle3 2010), and thus can possibly be derived from a calibrated, outer limb relative measurement between the thigh and the calf component location, from ground referenced limb position measurements.

Figure 5:
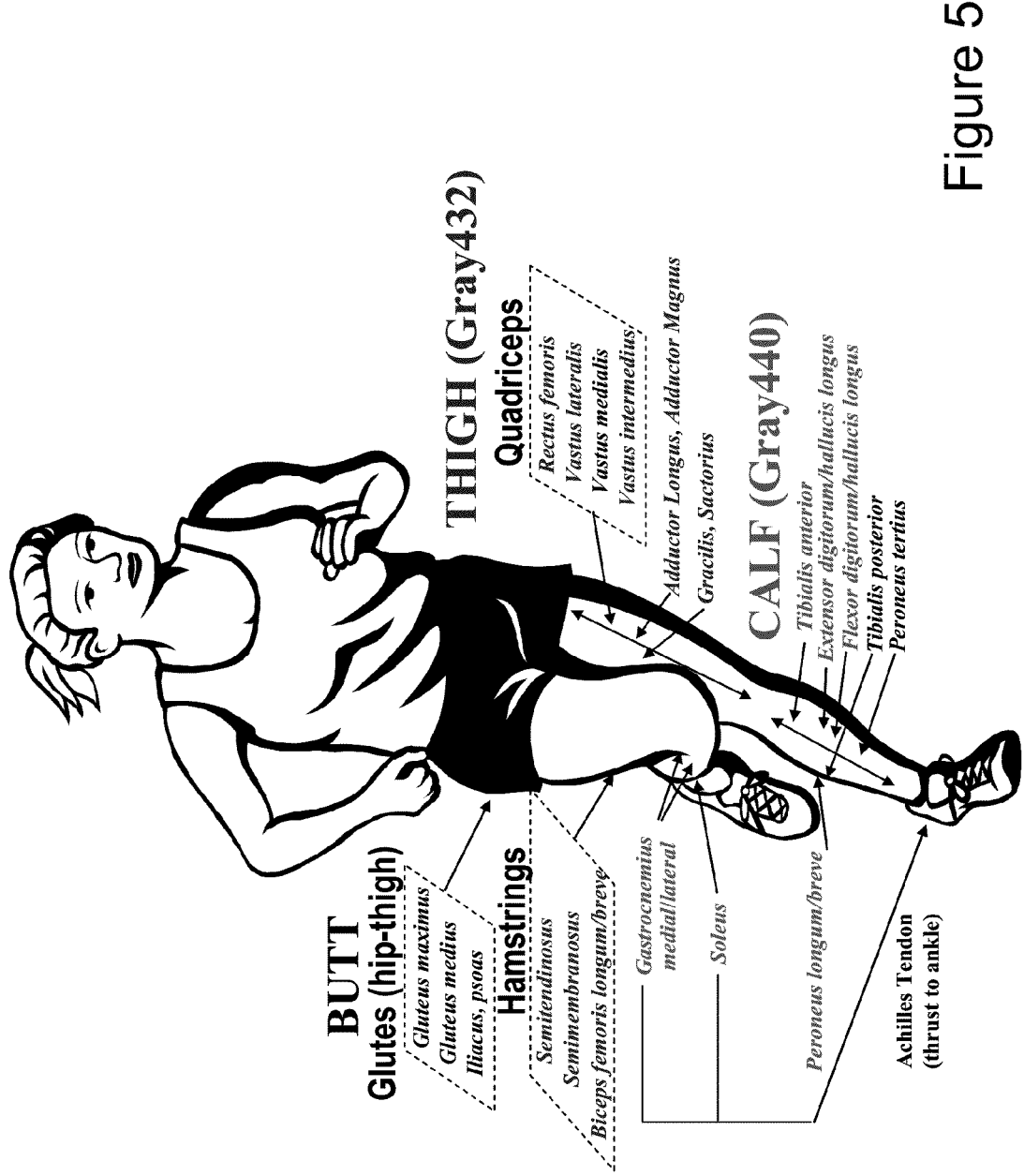
FIG. 5 shows '18' specific thigh and calf muscles contributing locomotion thrusts, as a subset of FIG. 4, with color-highlighting of mid calf and thigh cross-sectional, muscle contributions to circumferential pressure.

The major muscles involved in lower body locomotion can include 1) Biceps femoris longhead, 2) Semimembranosus, 3) Semitendinosus, 4) Adductor magnus, and 5) Gluteus maximus, as measured with human locomotion muscles using electromyogram (EMG) technology (Chappell 2009). FIG. 5 shows a more complete set of dominant locomotion muscles (e.g., '20' muscles for the calf and thigh midpoint cross-sections), and also shows the Achilles tendon element being driven by the Soleus and Gastrocnemius muscles. These muscle groupings are used in simulations and robotics; specific hip abductor and adductor muscles have even been measured in vivo to compute multidimensional-plane moment-contributions, such as in the knee joint stability (Nemeth, 1989). During the late-to mid-swing phase the Hamstring muscles come into play (Semimembranosus, Semitendinosus, and Biceps femoris longhead), with the medial hamstrings (Adductor magnus, Gluteus maximus) also coming into play as a relaxation just before the end of the phase. The hip abductors are the major functioning muscles during the initial stance phase using the 'Glutes' (Gluteus medius/maximus, and Tensor fascia latae).

The mid-thigh and mid-calf cross-section (e.g., Gray432 2010, Gray440 2010) muscles are highlighted in color in FIG. 5. Another important element in this modeling is the actual moment arms present during locomotion phases in abduction or adduction, and estimation of metabolic expenditure on muscle movement (Wang 2006).

Hence, there is a means of measuring a smaller number of muscle forces or after PCA/ICA analysis, to reduce the analysis to pseudo muscles as in a manner that might dominate Track and Balance function computation. This requires understanding what are the easily accessible, noninvasive, and measurable muscles, and then what one can infer from further muscle interaction with the brain requests, for forming metrics of Track and Balance.

Perceptive Brain Control of Muscle Functionality

In an examination of the neurophysiological basis of adaptive behavior through EEG measurements, Freeman (1975) has shown a mass action model for collections of neural "masses," with time-space behavior in a feedback loop control, which includes limit or terminal cycles, from impulse driven oscillations having characteristic frequencies from a periodic driven nature, or an aperiodic behavior at the subsystem levels. On a global scale, these are brain wave frequencies of alpha (8-12 Hz), theta (3-7 Hz), beta (13-30 Hz), and gamma (30-100 Hz), which are steady state, self-sustaining activities, but show a very short spectral resolution, as an inverse square frequency roll-off for temporal correlation (see Freeman 2000). Freeman proposes the aperiodic activity as stochastic chaos, which is a "ringing" of limit cycle attracters. One can extend this model to dynamic locomotion muscle actions as being impulse driven, aperiodic behavior at the local level, which is globally maintained in a more periodic control function based on the cognitive intentions of the brain.

Hence, in gait analysis, one can see stride-to-stride rate variability (SRV, West 2005, Scafetta 2009), representing human walking locomotion as an interaction of the central nervous system in the neural functions of the brain, and the intraspinal nervous system with the mechanical periphery at the bones and muscle levels, as a biomechanical model. This is a proprioception sense of locomotion, because there is a balance feedback from the limb tendons, muscles, and articular joints. However, kinesthesia is distinguished from locomotion by excluding the sense of balance. Proprioception is considered a feed-backward perception by making post-action adjustments of gait with 100 msec delays; however the feed-forward component for balance is also postulated in proprioception, where it is used for more rapid actions based on a pre-action knowledge of the limb locations, such as used in placing the fingers on the nose during a sobriety test requiring a placement accuracy to be within 20 mm. This feed forward/backward activity is one of the complexities in neural functionality in locomotion modeling.

Various training mechanisms can improve this balance sensing, e.g., using enhanced baseballs for proprioceptive pitch training, (Kuhn U.S. Pat. No. 6,663,519), gait analysis using walkers (Lancaster U.S. Pat. No. 5,311,880), and juggling or standing on a wobble board (Dewees U.S. Pat. No. 4,635,932, McShane U.S. Pat. No. 5,613,690), which is enhanced with the eyes closed. Also, a relatively new professional in human locomotion is the MD Physiatrists, which is an MD that has completed a Physical Medicine and Rehabilitation residency (also known as PM&R), who specializes in a wide range of things including neurological issues as well as orthopedic issues, and is mostly dedicated to the care and rehab of elderly patients, i.e., mostly those in rehabilitation. For example, after the acute medical issues are resolved in the hospital, many patients who are not ready to go home are placed under the care of a Physiatrist, such as for post stroke patients. These doctors are responsible for coordinating all of the care for these patients (e.g., non-operative modalities for many chronic conditions). Physiatrists also use motion and EMG analysis in treatment (SOAR 2010). This is a recent recognition of the link in locomotion between the biomechanical modeling and the neural feedback control derived from many perceptual properties.

Thus, locomotion is a combination of sensing footfall placement on a track of footprints after they occur, and a sense of balance used for anticipating the next footfall, thus, creating a feed forward track motion. Gait analysis using IR stroboscopic photometry has shown that elderly subjects had up to 20% reduction in velocity and length of stride (with stooped posture, faster cadence, and increased double limb stance) over young adults, and which also included reductions in toe-floor clearance, arm swing, and hip and knee rotations. This reduced combination of cadence and stride normally reduces the expenditure of energy, under the criteria of energy conservation. This reduced action, defined here as an integration of energy in time, can be considered that of a change in the neurological health of the elderly. This is why the combined determination of Track and Balance, when studying the conservation of energy in gait analysis, is critical to avoid artificial effects from stiff joints or absence of breath in the elderly (i.e., requiring a normalization within a variety of studied gaits; Elble 1991).

There are five basic temporal patterns in locomotion conditions, and when studied with four walking conditions (normal, kicking a ball, stepping over an obstacle, and stooping right and left while grasping an object), when using EMG muscle recordings from between 16 to 31 ipsilateral limb and trunk muscles in a set of 8 subjects, it showed that muscle activation associated with voluntary tasks was either synchronized with the locomotion, or had additional activations supporting a superposition model of compound movements (Ivanenko 2005). This complexity can be modeled with nonlinear mathematics shown in multifractal and chaotic EOM, and exhibit periodic and aperiodic behavior, which also exhibits irregular SRV, leading to falls in young children.

Unsteady locomotion is a sign of poor integration of muscle function with whole body dynamics and neuromuscular voluntary control, where fast-motion (e.g., running) depends more on local control that can be best modeled with spring-mass dynamics, which creates stabilization during unsteady running by animals from changes in terrain, lateral impulsive perturbations, and changes in substrate stiffness (Biewener 2007). These stabilization modes might be based on initial conditions, as seen in chaotic models, where the conditions arise from proximo-digital differences in limb muscle architecture, function, and control strategy. Nonlinear fractal exponent modeling for the data has supported correlation with forced pace gait conditions (i.e., metronome pace) having similar exponent values (−0.2) to Parkinson's disease (Scafetta 2007), and similar results were shown on a larger and more accurate measurement of analysis of cadence fluctuations from one stride to the next, which adjusted to provide optimal mechanical output at minimum energy (Terrier 2005).

There is also a feedback that compensates for length dependent neural control, using ground contact sensing from ground reaction forces (GRF), which cause a redistribution of energy by the distal muscles through their tendons. The optimization, of this energy use in locomotion, can allow mammals to achieve stability under a variety of conditions. Comparisons between GRF and kinematic (ultrasound) gait measurements of heel-strike and toe-off identification show high correlation, with slight differences with gait speed (Kiss 2010), implying that force inference does not have to be based on GRF measurements alone. This basic locomotion biomechanics is a vaulting over stiff legs in walking and compliant legs in running, but further analysis of these models with data requires a compliant leg for both, and shows that gait is but one of many legged motion solutions accessed by energy and speed, and is a useful model for representing stable animal and robotic locomotion (Geyer 2006, Altendorfer 2003).

Figure 6B:
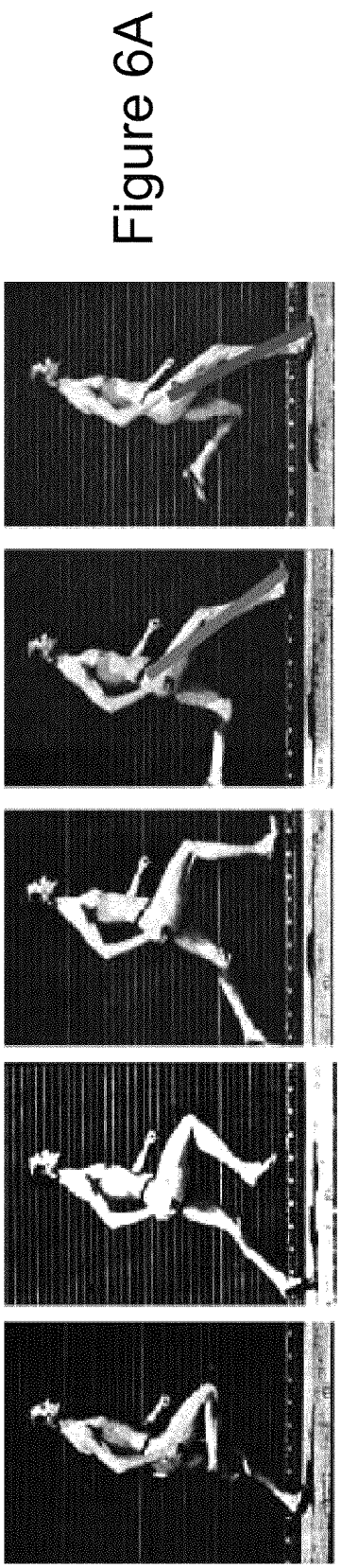
Figure 6B:
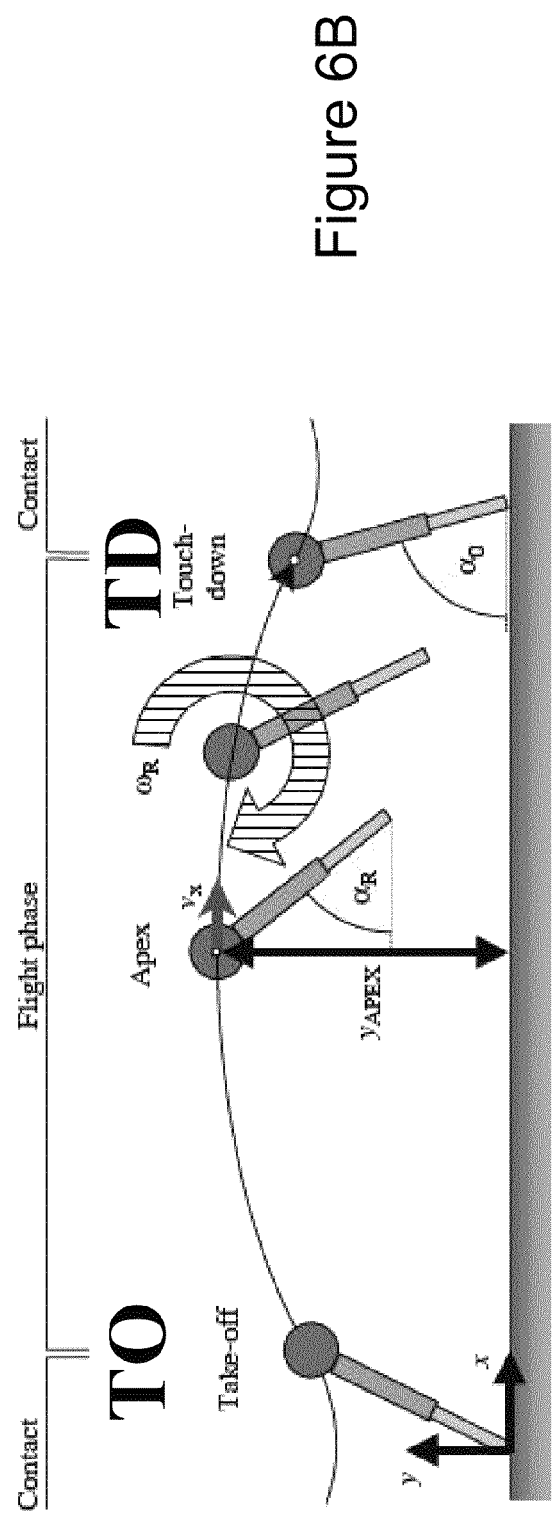

Another element of stability is in the use of a retraction of the swing leg through rotation, just prior to contact with the ground, changing the spring-mass angle-of-attack in responses to disturbances of stance-limb stiffness and forward speed, or a combined stiff, compliant limb, moving as a pendulum, but which is inverted, as an inverted pendulum model. Also shown in FIGS. 6A-1 to 6A-5 is a classic set of early still photos (Muybridge 1955; see Seyfarth 2003) of a runner leaving the ground without either limb touching. Thus, there is time during running in which the runner is airborne. FIG. 6B shows a spring model with retraction of the length of the limb after TO, and followed by right side TD landing after the flight-phase apex of maximum height, with a TD angle $\alpha_0$ (Seyfarth 2003, FIG. 1). With reference to FIGS. 6A-1 to 6A-5, the second frame shows the runner's left foot in the thrust mode going into TO and the last frame show the runner's right leg in TD.

Figure 6C:
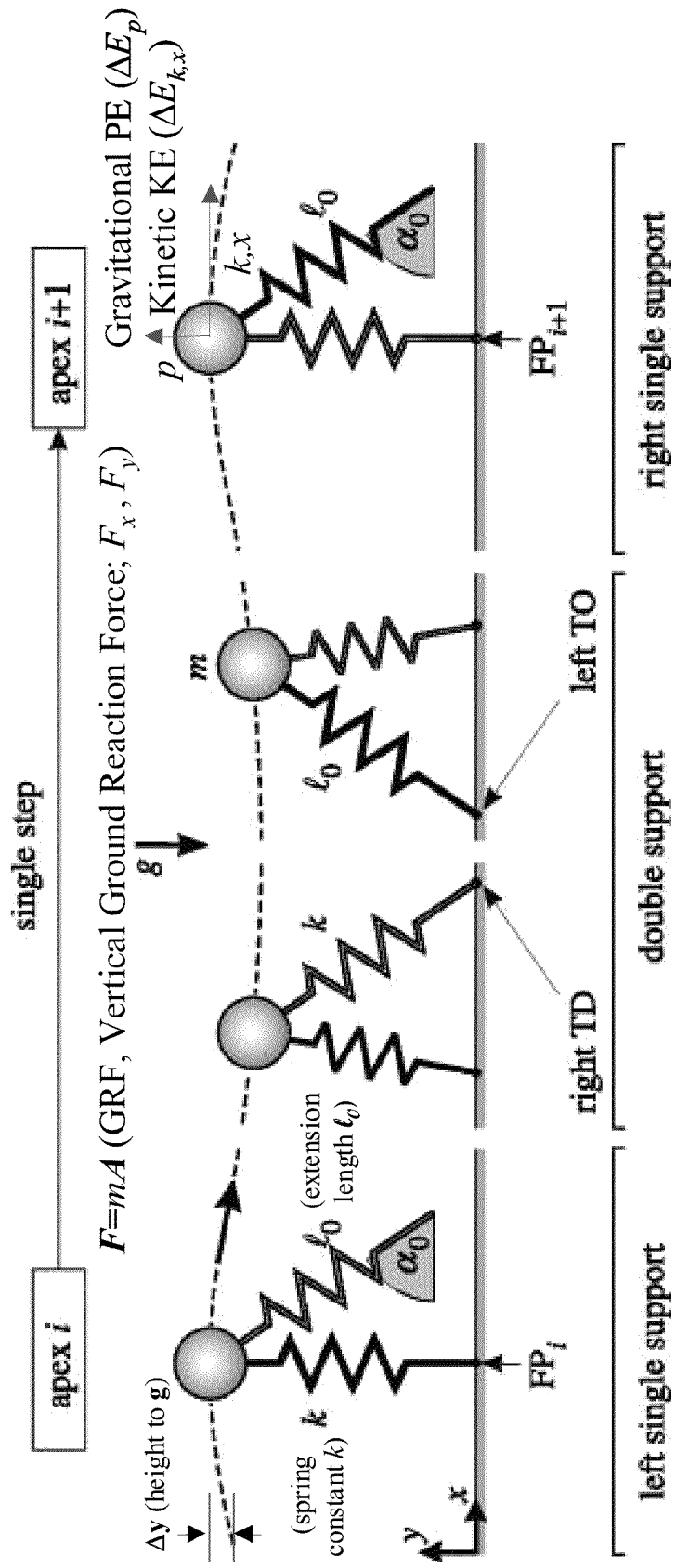
Figure 6D:
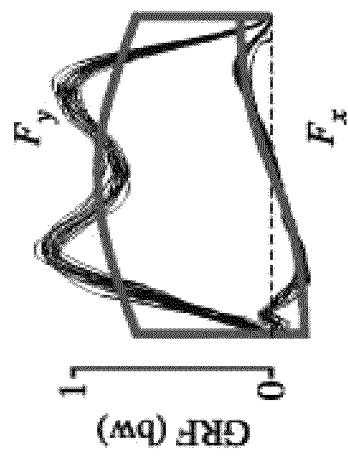
Figure 6D:
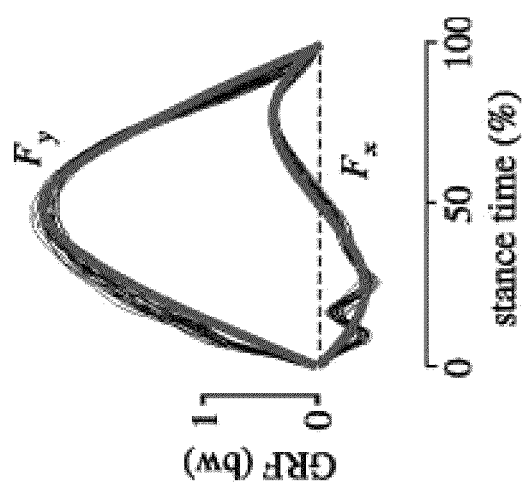
Figure 6D:
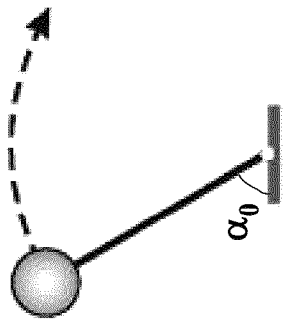
Figure 6D:
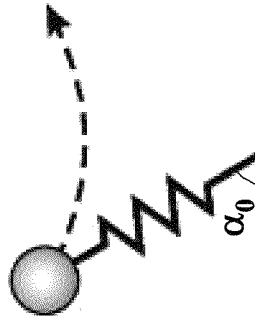
Figure 6E:
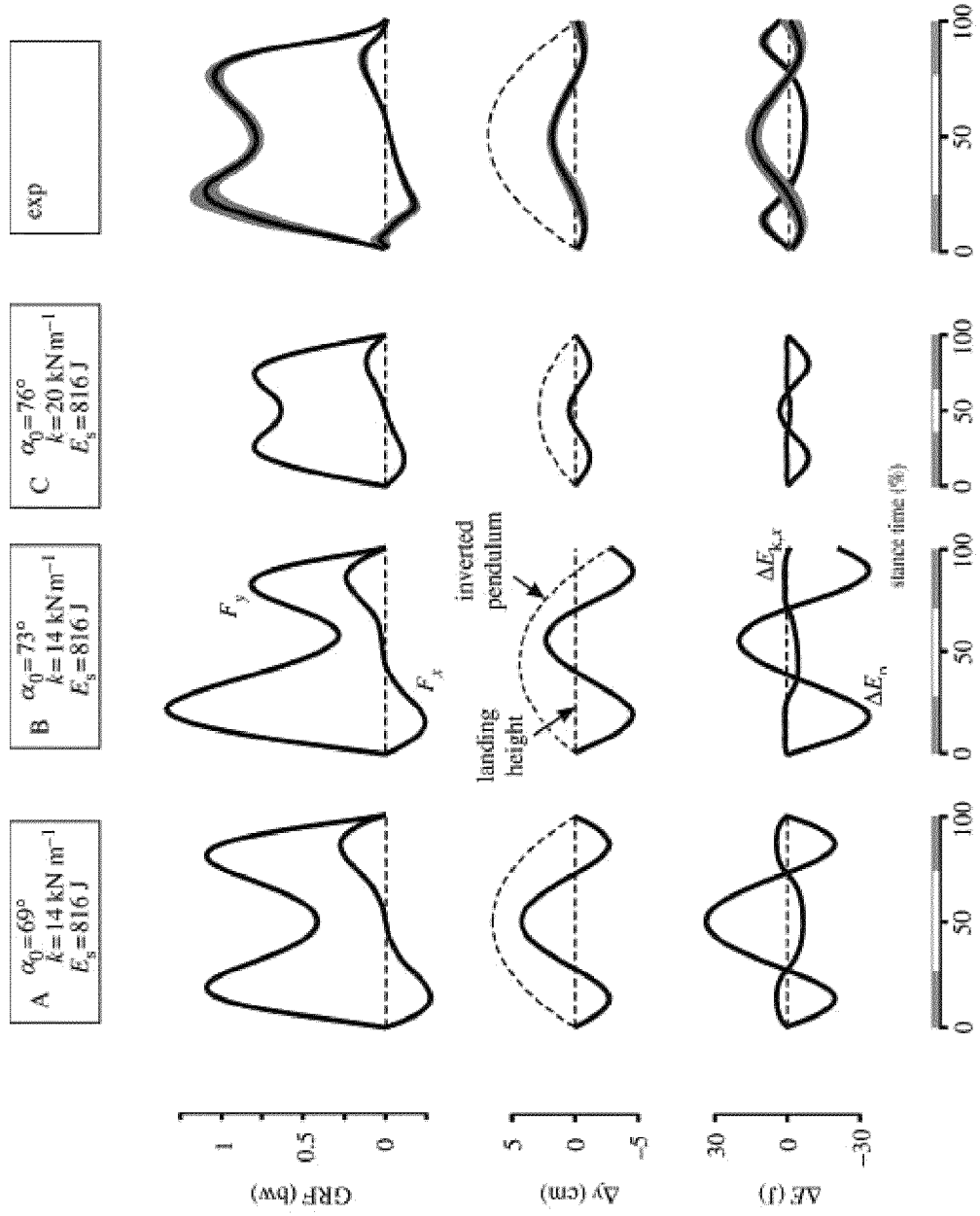

Another model detail is shown in FIG. 6D, where the inverted pendulum is modified from walking to having a spring for running to compress the muscle as a deceleration. The GRF is also shown in the figure as a percentage of the stance time, having the double hump for walking and a flatter, single hump for running. FIG. 6D shows that the compliance models fit the data reasonably well for the running, but less so for walking. FIG. 6C shows this two spring model (in which both legs have springs), with the single foot support, moving from left stance, to both in stance, to right stance, and during the double support at the center, with the transfer between the right-leg TD and the left-leg TO. The model's agreement with data measurements, shown in FIG. 6E is quite good, for three parameters: horizontal-axis stance time (%) and vertical-axis for 1) PE changes (J), 2) Height in G (cm), and 3) GRF (in body weight). Here, there are three model parameter sets (parameter value sets A, B, C, including touchdown angle $\alpha_0$), being the closest to the data ("exp") at $\alpha_0=76°$ (Geyer 2006FIGS. 1, 2, 3). This similar model by Geyer showed basic dynamics of combined running and walking, and used the swing leg parameters listed above, and the constant system energy in the conserved energy assumption (Geyer 2006 pg 5). The earlier model by Seyfarth also uses parameters of leg angle $\alpha_0$, but also leg length $l_{LEG}$, to show swing leg retraction in FIG. 7 (Seyfarth 2003FIG. 7), having a stance phase in this two parameter space that moves on the cycle from TD to TO as being periodic over a half cycle, and then moves into a very nonlinear behavior during the swing phase (TO to TD) that includes retraction, thus changing the angular momentum in an aperiodic part of the cycle (with a reversal nonlinearity shown in the magnified section on the right side of the FIG. 7), with a further example of this distortion, shown in FIG. 7, being amplified for disturbed running conditions (Seyfarth 2003FIG. 7). These models are used in robotic studies of four-legged locomotion in simulated and real environments that are optimized to minimize the system energy used in gait locomotion (Brambilla 2006).

Figure 7:
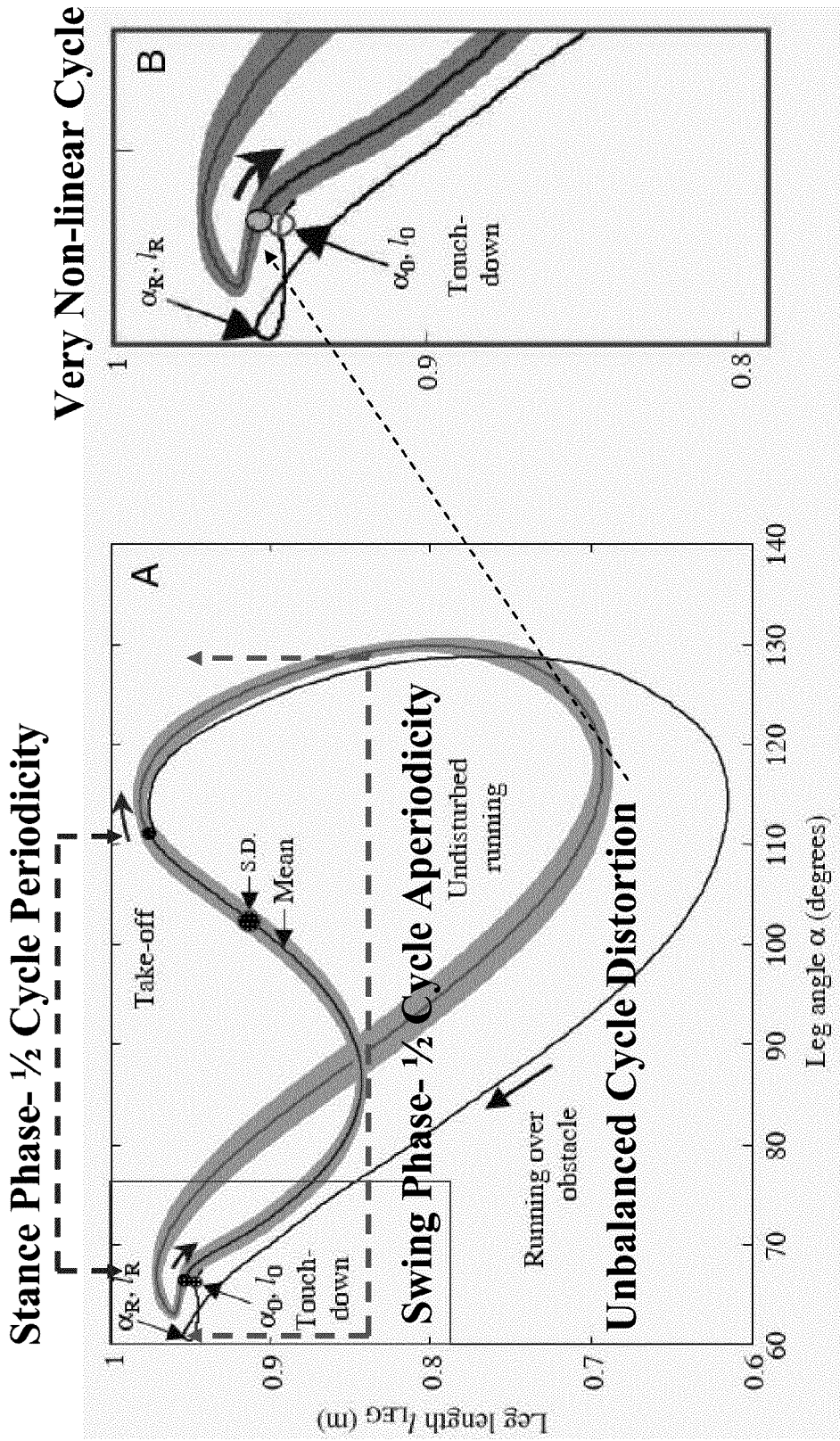
FIG. 7 shows modeled periodic and aperiodic leg motion for stance and swing phases.

FIG. 7 shows a locomotion cycle for a leg in the coordinates of the leg angle a and the leg length. Referring to the left side of the figure, starting at TD, the cycle proceeds in a sinusoidal manner to TO. Thus, in the stance phase, the leg has touched down and is simply swinging forward. After TO, there is an aperiodic phase (i.e., does not proceed in a sinusoidal manner) during which the leg returns to TD. The left side of the figure also shows a situation in which the person has lost balance and there is a very different cycle between TO and TD. Thus, FIG. 7 shows a first "stance" phase with ½ cycle periodicity and a second "swing" phase with ½ cycle aperiodicity. The example systems and methods described herein do not require knowledge of leg position. Instead, as explained in greater detail below, these systems and methods determine the change from periodic to aperiodic (or sine to "non-sine") shown in FIG. 7 to find TO and TD. For example, a fourth-order detector can be used during data correlation to determine changes from periodic to aperiodic and from aperiodic to periodic. During the periodic ½ cycle, the fourth-order detector will have a zero output. This output will become non-zero during the aperiodic ½ cycle and the transition corresponds to TO. At the end of the aperiodic ½ cycle, the output will again become zero and the transition corresponds to TD. In short, the fourth-order statistics are zero during the periodic stance phase and non-zero during the aperiodic swing phase and the transitions between the phases can be used to determine TO and TD. By finding these two points in the dynamic of a gait cycle, integration can be performed to obtain the energy. This can be used to, among other things, obtain gait metrics as well as Track and Balance. The metrics can show, for example, optimization of the use of energy by being in balance and show that optimization at any different rate at which a person runs, walks, moves, etc.

Finally, complex models (e.g., 54 muscles with 23 DOF in 3D motion) are argued to be required for discerning the functional role of muscles in locomotion that include the centrifugal joint motion and gravitational forces, as well as being used to understand which muscles contribute to the two peaks in FIG. 6E experimental results. Much has been learned through simulating 3D walking humans, including suggesting that hip muscles contribute to vertical CM motion not present in the double inverted pendulum, 2D model. Here, the second pendulum is the knee angle changing with the thigh motion, as a mass movement from the calf to foot angle as the first pendulum (Pandy 2003). This can also be another parameter in the EL generalized coordinates.

Thus, recent brain control research in locomotion functionality has shown that locomotion dynamics might be overly simplified in gait parametric modeling, and a much finer scale of global and local neurobiological nonlinear modeling is required for a detailed representation to develop Track and Balance metrics. A further element in human locomotion and muscle exertion is the modeling of energy expenditure, which is discussed next.

Energy Expenditure in Human Locomotion Models

Human balance (Shepherd 1988) uses open-loop sensors of changing tilt (statocyst as velocity, v, and also gravitation, g, or as a gravireceptor) and closed loop sensors of rotation from shear force motion (canal as angular acceleration ω). Human locomotion (Shepherd 1988) is primarily developed by exertion of thrust forces from external limbs, involving external surface contact, and muscular contractions moving the skeleton structures in the limbs (vertebrates). This locomotion is modeled as being controlled by synchronized nerve firings, to execute muscular contractions, in conjunction with states of motion constraints, using closed-loop sensor feedback (e.g., walking, running, crawling, movements, resulting from the transmission of a limb pressure area in contact with the ground surface that generates the body thrust force). Early computer simulations for primate bipedal walking used biomechanical models of displacements, with data substitutions for acceleration, joint angles, CM to gravity, foot force (e.g., GRF), joint moments, muscular force, power from the leg, and energy expended during walking (Yamazaki 1979).

As previously stated, this motion is in the form of an oscillating pendulum, but that is inverted, and hence has to be kept in balance. This synchronized limb movement is an aperiodic oscillation pattern of contact, which is created to conserve the angular momentum of the body's balance, during the oscillations of the upper torso, and thus the inverted-pendulum (upright human) does not fall over. Three neural components of muscle exertion and sensing feedback achieve this aperiodic, motion balance (i.e., 1) environmental contact of effector organs with reflexive feedback, 2) central pattern organs with spinal twist and turn feedback, and 3) higher levels of control in the brain). The motion of the runner photos in FIGS. 6A-1 to 6A-5 emphasize this balance, from only one foot touching the ground in walking, and sometimes for short periods in running, neither leg is touching the ground (or even with four-legged horses; Brill 2003). The complexity of achieving a similar balance in extreme sports is now obvious.

Modeling improvements in bi-pedal walking have become more complex in order to study body evolution; e.g., with ten 2D links, of 26 muscles, and 18 neural oscillators for the local cycles; using an evolutionary genetic algorithm, of the neuromuscular skeletal model under minimized energy locomotion, made the body shape model migrate from a chimp shape to a human shape. This shows the dramatic need for reducing the skeletal loading and increasing the efficiency for human locomotion models (Hase 1999). Complex models for neuromuscular control of human locomotion have suffered from computational inefficiency; however using a min-max strategy in a generalized Newton method, an example of predictive control in a seven segment model with 18 independent muscle groups was found to agree well with EMG experimental data (Kaplan 2001). While there have been many human locomotion models for various applications, body dynamics and power transfer between limbs has been dominate in modeling and simulation of muscle driven dynamics (see Zajac 2002, Zajac 2003), which has provided a better understanding of locomotion data using a synergistic action of other non-energy producing muscles, which produce instantaneous accelerations and redistribution of segmental energy. This is similar to a muscular process of neurologically lighting "firecrackers" of injected energy at the parts of the limb muscle to effect movement, but without a well-defined biomechanical component.

These models use a multi-segmented ballistic and passive mechanics of walking, yielding clues to healthy and pathological gait. They also can include detailed 3D models of the joints (Abdel-Rahman 1998), and can be complex with knee joint loading and predictive neuromuscular control effects leading to ACL injuries. Model parameters are varied to achieve motion and GRF within a 1-rms error to experimental data results as an optimization of muscle stimulation patterns during a sidestepping task (McLean 2003). Agreement with data is achieved in many cases when the model assumes a minimization of energy per unit distance, and the simulations also show two muscle modules active in that expenditure: Module 1 (gluteus medius, vasti, and rectus femoris), and Module 2 (Soleus and Gastrocnemius), which are similar to thigh and calf cross-section muscle monitoring midpoints (Neptune 2009). A recent spring loaded inverted pendulum model (Allendorfer 2003) uses the form of leg swing as the inverted pendulum, and foot slip for self-stability. One critical assumption in this approach is to show the conservation of torque in the human locomotion by the arms and legs, for a constant linear CM movement (i.e., aperiodic, but still cyclic to a zero point oscillation). This new human locomotion modeling has added features to this component of the simulation, e.g. leg swing and self-stability.

Figure 8:
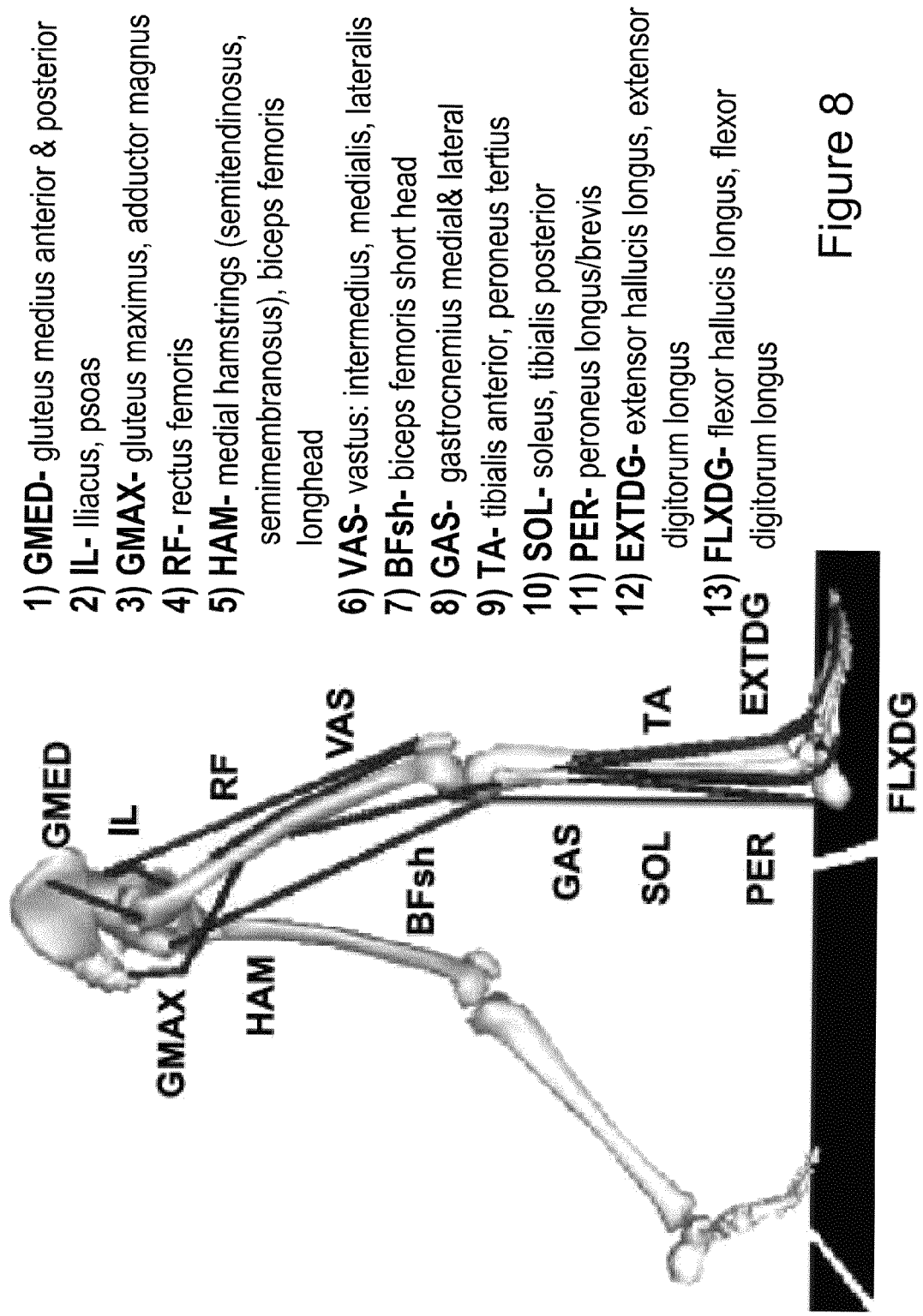
FIG. 8 shows the dominant lower body muscles used in locomotion simulations.

FIG. 8 illustrates the dominate muscles of the lower body used in this motion simulation (Neptune 2009b), similar to the dynamic simulation example of FIG. 3, where the human locomotion is modeled as a dynamic parametric amplifier. These muscles used in simulation are listed from the hip, to the thigh, calf, ankle, and toes, as being the "18" muscles in the lower body (e.g., the number of muscles identified in the literature for lower body dynamics is not consistent in detail, and quotes are used here for the numeric value).

Thus, the motion of the runner in FIG. 3 is simplified as "rigid body" motion of the spine twisting, the arms and legs "pumping," and the side-to-side rocking of the body from the changing leg forces from the footfalls. Because this motion is about the vertical gravity vector, as stated earlier and shown as a green arrow in the figure, it is considered as the motion of an inverted pendulum. Also, because it is similar to the cyclic motion of the swing dynamics changing from KE to PE to KE, it can also be considered as a parametric amplifier with the length of the arm or leg being the changing parameter of the nonlinear amplification dynamic and time period (e.g., the swing pumping is in phase with the peak/valley PE points of the cycle). This is similar to children pulling the swing ropes, while swinging on a playground swing set, which increases their swinging to a higher level (e.g. as modifying the rope length parameter in synch with the peak height, thus amplifying the motion). This is a mass movement parametric amplification, only here, the runner in the figure is changing the mass positions in phase with the torso twisting, which is in phase with the footfalls. The locomotion models discussed earlier addressed such concepts, but without the component of the twisting spine and the arm length/angles also being changed in a synchronous manner. Among other things, these models did not simplify this metric for a Track/Balance segmentation of the gait cycle dynamics.

All of this research shows that the locomotion muscle actions are in a much more detailed neural control across many levels of local-global abstraction than simple biomechanical models indicate, and argues for a simplification of this complexity in utilizing automation for enhancing the utility of gait metrics.

Gait Analysis Techniques

The analysis of gait movement is performed in laboratories measuring the body motion (kinematics) and forces involved to produce this movement (kinetics), such as force plates being stepped on (Roost U.S. Pat. No. 5,186,062, Fuglewicz U.S. Pat. No. 5,299,454), with walkways and treadmills for constrained motion, and strobe lighting of photographic images, video recordings, and multiple cameras for 3D limb location. Also, marker systems are used for reflecting from body placed reflectors (Pugh U.S. Pat. No. 4,631,676) at specific locations using IR lighting and cameras, or these can be beacon emissive illuminators. A trajectory of the motion is derived from computer analysis. All of this motion and force measurement use Newton's Equations to compute joint dynamics and forces, and net moments of force at each joint. The analysis is limited to individual muscle groups, such as extensor or flexors of the limb. Specific muscles can be instrumented with surface electrodes for EMG recordings for activation timing and level, which measures contributions to gait and prosthetic limb control (Wells US 2006/0155386). Analysis of this gait data, as deviations from normality, is used to diagnose specific conditions (e.g., compensation for underlying pathologies, and application of rehabilitation engineering), or in clinical applications for sports training and effects of corrective Orthopedic surgery, and to predict outcome from treatments, or measure the effectiveness of training programs.

Existing gait analysis equipment includes laboratory instrumentation of foot placement position on force plates using treadmills or on sensing cross-wire grid pathways (Trantzas U.S. Pat. No. 5,952,585, Boyd U.S. Pat. No. 4,600,016), and with/without upward looking cameras, and can be instrumented using force plates for detecting heel-strike and toe-off (Nashner U.S. Pat. No. 5,474,087, Nashner U.S. Pat. No. 5,623,944). These measurements are also used for podiatric diagnosis (Anderson U.S. Pat. No. 4,416,293). Simultaneous body motion analysis is made using video recordings of joint markers, positioned on the outer body sides, or 1) using beacons (e.g., visible and RF tags (Au U.S. Pat. No. 4,813,436, Menache U.S. Pat. No. 6,831,603), 2) ultrasonic, 3) RF (Kane U.S. Pat. No. 6,784,826, 4) RF tracking (Polhemus.com) of snowboard ankle location and joint rotation (Delorme 2002), and 5) pulsed EM tracking (Ascension-tech 2010) of foot for building models (Brown 2009), 6) combined RF and ultrasonics (Solinsky U.S. Pat. No. 6,292,106), and 7) IR emitters to locate body parts, when placed on the body for 3D ranging solutions. Most all gait analysis is either in a laboratory environment, or as an embedded system, such as in a testing room or in a hallway using step vibration monitoring (Alwan US 2006/0195050).

Direct placement of MEMS acceleration and rotation sensors on the body is generally on the foot as point measurements (e.g., in the shoe-sole (Hubbard U.S. Pat. No. 6,360,597, Wanderman U.S. Pat. No. 5,511,561), shoe-top, shoe-back, shoe-heel, or multiple shoe positions about the shoe sole (e.g., Confer U.S. Pat. No. 4,745,930, McCarthy U.S. Pat. No. 7,648,472, Asphahani U.S. Pat. No. 6,836,744, Hutchings U.S. Pat. No. 5,724,265, Hutchings U.S. Pat. No. 5,899,963, Fyfe U.S. Pat. No. 5,955,667, Farringdon U.S. Pat. No. 6,807,869, and Bengtsson US 2004/0154192), and on the wrist, hip, waist, back, chest, head, etc., with direct wired (Stergiou US 2007/0021689) or RF connectivity (Hanawaka US 2008/0146968, and as motion capture (Biosyn Systems 2010) for data collection. Additionally, limb relative position measurements to determine relative joint angle motion can incorporate mechanical ligament testing (Daniel U.S. Pat. No. 4,969,471), wired goniometric sensors strapped to the limbs (McLeod, U.S. Pat. No. 4,834,057) or as rotational, optically coordinated sensing using attached limb locations (Broers U.S. Pat. No. 7,611,520).

These direct sensor measurements placed on the body have allowed for mammal motion analysis of humans in both gait, activity, and navigation applications with/without RF connectivity (Solinsky U.S. Pat. No. 7,610,166 (using Hg Loop sensors on muscles, indicating pressure changes from stressors, see Hokanson (1975), Pretorius (1989), Urso (1990)), Kahn U.S. Pat. No. 7,647,196, Daumer U.S. Pat. No. 7,640,804, Dar U.S. Pat. No. 7,632,239, Hanawaka US 2008/0146968), and for other mammal motion analysis, such as horses in both gait and health applications (as video (Wang, US 2007/0229552), as track placed sensors (Tasch, U.S. Pat. No. 6,699,207) or sensors placed on back and foot (Davies US 2006/0000420, Bushman U.S. Pat. No. 7,552,538) as for heel strike and weight sensing (Vock U.S. Pat. No. 7,627,451, Vock U.S. Pat. No. 7,620,520).

However, these direct sensor approaches involve at least one sensor attached to the foot, and an offline analysis of the data to have utility, because the sensed data from two or more limbs is not being compared in real-time. It is not clear that a Track and Balance approach requires defining the gait cycle with on-foot, TD/TO measurements, or by using GRF force plate measurements.

Gait Analysis Metrics

The anatomical terms of locomotion are defined as the movement of the body structure by the contraction of the muscles, and are defined by the direction that the muscles move skeleton parts relative to each other (e.g., flexion (bending) and extension (straightening), abduction (pulls away from body midline) and adduction (pulls toward body midline), internal or medial rotation (turn hip, shoulder, toes inward towards midline) and external or lateral rotation (turn hip, shoulder, toes, arms outward towards midline), elevation (as superior direction up) and depression (as inferior direction down); there are also special terms for the hands and feet (as surfaces, forearm rotation, flexion of the entire foot, and movement of the foot sole away/towards the median plane) (Anatomy2 2010).

The study of kinesiology in physical therapy is not limited to gait analysis, and combines human movement with physiology, and began with early descriptions of complex rotary (ACM) and translatory motion (CM). The analysis divides actions as events, being the definition of phases of movement (e.g., descending and ascending with a squat, and the two knee flexions), specification of the joint involved, and of the axis and plane of the movement, and the internal and external involved forces, with identifying contributing muscles. Each plane of motion has a variety of axes and angular directions for specification. This is combined with forces and moments acting around a joint. Hence, much of the body kinesiology involves angular motion creating thrusting (e.g., acceleration, deceleration) forces (Mathiyakom 2010).

The basis of gait analysis lies in the changes during the vertical, lateral sheer, and progressional sheer forces during the GRF pattern, of the stance phase of gait, in terms of body weight or vertical acceleration. With no force, the weight is considered to be the actual weight on a scale. Changes above and below the scale weight are forces of acceleration and deceleration of the body, which change with gait speed. Slower speeds as in walking create the two peaks of the 62% period of the gait cycle for walking, and a reduction in the running phase to half that for slow walk, and a flattening into one wide peak at body weight for running. The moment of torque in the joint movements creating a rotary force that moves the joint occurs when the mass of the body is not vertically aligned over the joint; muscle actions restrain a postural collapse. Sagittal plane angles for thigh and hip joint motion change during the gait cycle (flexion/extension: thigh (20°/20°) and hip (30°/10°) for 0% and 50% of the gait cycle, with (25°/35°) for 85% of the gait cycle), indicating relative changes of the thigh must be separated from the hip motion, which is done from an axis vertical to the horizon. This hip torque changes significantly in amount between flexion and extension motion during the stance phase, accompanied by a change in the body weight vector, which is a change in the constant gravitational acceleration (g) from the thrust force acceleration (a) of the foot as a misalignment of the vectors, which is quickly re-aligned (e.g., 2% of cycle, see FIG. 6). Such alignment can only be determined with direct measurements on the limbs of a and g.

Dominant hip muscle groups are the hamstrings (biceps femoris longhead, semimembranosus, semitendinosus, and adductor magnus and gluteus maximus) contract in late mid swing (80% of gait cycle) and relax just before contact, but with differences in the overlapping activity. A similar analysis can apply to other muscles groups (Perry 1992). More recent in vivo tomographic analysis has indicated that more muscles might be involved than just the abductor and adductor groups for joint stability, in order to properly represent hip forces, based on 3D analysis of subject data and computed moment arms (Nemeth 1989).

Biomechanics analysis of the gait cycle of a stride, consisting of two steps taken in a stride time (actually the number of steps in the gait cycles are as there are number of legs, thus differing between humans and horses), beginning the cycle with the initial contact of the limb on the ground surface (heel-strike or foot-fall, TD, etc.), where toe-off (TO) begins for walking at 62% of this cycle, dividing the cycle into the stance and swing phases, with a forward normal or natural walking speed at 1.5 m/s. Foot-angle or toe out is the deviation of the foot mid-point muscles from the placement from the forward progression line. The step-length is the distance between the heel-strike of one foot to the following opposite foot, heel-strike, and walking base is the length in perpendicular measurements defining forward motion. The step rate is the cadence in steps/min, defining the stride length as (120*speed)/cadence, which is normally 1.5 m. Various analyses of gait parameters has proven useful, such as data at natural, fast, and slow categories of speed cadence and step length, and in scatter-grams of cadence vs. walking, stride length vs. speed, natural stride length vs. height and leg length, and cadence vs. root-square of leg length. Results show linear and quadratic relationships for regression analysis of these scatter grams (Locomotion 2010). Mean values differ between males and females (M/F) as step-length (cm) 79/66, stride-length (cm) 158/132, cadence (steps/min) 117 [60-132]/117[60-132], speed (called velocity in m/s) 1.54/1.31, and walking-base (cm) 8.1/7.1, and foot-angle (degrees) 7/6 (Stride 2010). In addition, an analysis by members of the orthopedic profession showed agreement on rear-foot angle as a means of defining clinical assessment of foot type variances, indicating the utility of this metric in gait analysis (Chuckpaiwong 2009). Thus, current gait analysis metrics are still focused on foot joint angle modeling, with demographic representations of simplified, standardized measurements.

Gait Analysis Applications

The various techniques described above, for assessing locomotion through gait metrics, are applied for a variety of applications in diagnosis, physical therapy, training, and post operation treatments, such as in sports injuries (including ACL injuries), elderly care, orthopedics and chiropractory, which are among others in the following examples:
1. Sports injuries (e.g. activities of football, basketball, skiing, skating, snowboarding, and contact/non-contact, and male vs. female knee ACL injuries):
   a. General research has shown a variety of technologies useful in studying sports injury mechanisms, involving video (ACL, lateral ligament (leg side), modeling, interviews, cadaver and dummy analysis, in vivo (strain & force measurements) and clinical (arthroscopy, radiology, CT, MRI) studies, are required in combination and also with the mechanisms leading up to and at the injury time (e.g., landing with sidestep cutting, unforeseen footpath changes/obstructions) (Krosshaug 2005), (Withrow 2006).
   b. Gait transitions in walk run (WR) and run walk (RW) on treadmills suggest they occur over extended times beyond a step up to a stride (Hreljac 2007).
   c. ACL injury mechanisms are more dominantly from non-contact injuries (72% vs. 28%), occurring at foot-strike (TD) with the knee close to full extension, such as during deceleration prior to a change of direction or landing motion, where contact was related to a collapse of the valgus, collapsing of the knee. Conjecture is that the extensor mechanism can strain the ACL and maximum, eccentric muscle force conditions, with also the quadriceps playing a disruption role, where the passive protection by the hamstrings has been reduced from an above average flexibility (Boden 2000).
      i. There are over 200,000 ACL injuries in the US, with 50% being surgically corrected. The ACL injury is a tearing of the ligament and an injury to the joint surfaces or menisci (articular or footballer's cartilage), which inhibits the normal ACL information about balance to the joint and surrounding muscles, and allows the knee to give way; this can be improved with specific exercise and reconstruction surgery and a proper rehabilitation exercise program. However, full recovery from the injury is never complete, and avoidance of ACL injuries is preferred (McNicholas 2010).
      ii. The use of braces in post surgery rehabilitation has not always been beneficial, due to potentially a decrease in neuromuscular activity as measured from coordination tests and EMG in drop jump tests. Analysis showed that improvements were due more to mechanical action, enhanced coordination, and a psychological effect (Rebel 2001).
      iii. Risk factor analysis of ACL injuries show a dominance of athletic movements, and a potential for miss identifying risk factors leading to non-optimal injury prevention programs. The injury is based on an excessive tension force loading being applied, which can occur under non-contact conditions. This loading is driven by the interplay of the GRF and the quadriceps muscle contraction force. Biomechanical studies are not always predictive of valgus moment loading, but a vertical drop landing did show predictability. In particular, soccer, basketball, and volleyball players over three seasons showed knee abduction angle at landing was 8° greater in ACL injuries, vs. non-injuries (Garrett 2009b). This strain was measured in the anteromedial bundle (AMB) of the ACL using strain gauges, which showed that the anterior tibial force was the primary determinant of AMB strain, when increasing with angle from 0° to 30°, and when the AMB medial force was combined with anterior forces, it was shown to account for 50% of the strain, being similar to valgus torque and internal axial force combinations. This is an increased strain for injuries being attributed to muscle combinations, not well represented in single muscle actions of simple biomechanical models (Berns 1992, Berns 2005).
      iv. Knee angle data and thigh muscle activity EMG measurements in woman showed for squats and step-ups to be dominated by quadriceps activation and hence be an inexpensive exercise for ACL rehabilitation (Beutler 2002).
      v. During preparation for landing in vertical stop jump is related to risks for non-contact ACL injury that is greater in females than males. Males exhibited a motor control pattern of increased hip and knee flexion to absorb GRF in preparation for impact and ACL loading, as shown from increased quadriceps and hamstring EMG activity (Chappell (2009).

vi. Approaches studying ACL injuries from the sidestep cutting motion, modeled dynamic skeletal behaviors for 10 males and 10 females from force plate measurements, and examined the external knee anterior force and valgus internal rotation moments. Kinematics came from 3D coordinates of skin marker motion using 6-shuttered video cameras. Modeling used 12 DOF from 5-supporting skeletal segments with 31 muscles. Modeled peak anterior drawer muscle forces were below levels required for ACL injuries. However, valgus loads did reach values high enough to rupture ligaments, and was a more likely injury in females. In disagreement with past publications (Griffin 2000), the new study concluded that modifying the Sagittal plane biomechanics would be unlikely to prevent ACL injuries (McLean 2004); see Griffin article cited by 56 articles from 2000 through 2010; see also (Song 2001), for a similar 3D modeling with less than 10% error between computations and experimental measurements, where the issues of including ACL material properties might improve further injury predictions.

vii. Agility training improved medial hamstrings activity (as measured with EMG in rectus femoris, vastus medialis oblique, medial hamstrings, and lateral hamstrings, and EM kinematic motion analysis) in female basketball players during a sidestep pivot maneuver, which might reduce ACL sprains and injuries, relative to a test group without agility training (Wilderman 2009).

viii. More recent work has identified risk factors between non-contact ACL injuries and mechanisms at work, but asks more questions than answers: do training effects generalize to competitive situations, do they lead to long-term behavior change, do they scale with size, do they deal with stretching and endurance. The study identifies prevention as not only a motor control and technique issue, with repetition and practice, but these are done under very controlled and balanced conditions, and hence they do not get at the heart of the real environment that contributes to the injuries. An effective approach must be done often, and involve strength, neuromuscular control, and monitoring over a larger group with better measurements (Garret 2009).

2. Other injuries and physical training (e.g., volleyball, weightlifting, golf putting)

a. Professional volleyball sports requires stable joints in order of ankle, knees, hips, and lumbar spine, which come from walking on the balls of the feet for barefoot balance, instead of heel-strike walking, which requires non-shoe instrumentation (Performance Corps 2010). This is similar to the stable, body-centered walking used in martial arts (e.g., Aikido), and is present in many jumping and sprinting activities.

b. Olympic weightlifting in the snatch and the clean and jerk is best as a continuous motion, with training feedback derived from more typical motion analysis of noting limb positions as post action feedback, but feedback training is actually aimed at achieving a continuous balance throughout the execution (Polhemus 2010).

c. While motion analysis has been used in golf swing training (Polhemus2 2010), it has not been applied to putting, beyond constraining mechanical systems (Automatics 2010), and hence would benefit from a Track and Balance separation during analysis.

3. Post-stroke rehabilitation (600,000 survival cases per year)

a. Use of EMG feedback after stroke (accompanied with foot-drop) improved recovery of functional locomotion beyond just physical therapy (Intiso 1994). Using a percentage of body weight being supported during treadmill stimulation in gait training resulted in better walking abilities (Vistintin 1998). In general, treadmill training after stroke has improved recovery with substantially increased walking speeds, and fast walking showed speed related improvements in body and limb kinematics and muscle activations (Lamontagne 2004).

b. Reduced walking abilities in post-stroke patients was observed in spatiotemporal measurements with 3D GRF sensing, quantitatively linking the paretic leg output with this forward propulsion measurement as a possible tool for distinguishing functional compensation from physiological restitution (Bowden 2006).

c. The mechanisms underlying motor recovery after stroke are not fully understood. Using functional MRI (fMRI) analysis of brain activity has only recently been applied to the lower limbs. Partial body supported treadmill training of chronic patients with post-stroke moderate paresis was investigated. Despite strong subcortical contributions to gait control, rehabilitation-associated walking improvements with the distal ankle movements, in analogy with similar studies of hand wrist movements, are associated with cortical activation changes, with the recovery with foot movements being distinct (Enzinger 2009).

d. Impaired walking performance post stroke may be assessable through analysis of gait variability (e.g., step-lengths, stride-widths; and pre-swing, swing, and stride times), and was shown particularly for between leg differences to be useful as quantifiable markers of impaired walking performance (Balasubramanian 2009).

e. Assessment of symmetry in post-stroke hemiparetic walking relative to speed is not well defined. Variations in moving towards and away of asymmetry in split-belt gait analysis was not able to correlate step-length or propulsion symmetry with ankle impulse proportions, thus indicating kinematic mechanisms for increased speed are not currently predictable (Beaman 2010).

4. Whiplash, spine and neck issues (>5,000,000 major cases)

a. Whiplash chronic injuries involved trunk sway measurements during clinical stance, and were compared to gait tasking to see if specific patterns emerged between chronic and normal subjects. Greater trunk sway differences were noted for task-specific gaze control, such as walking up/down stairs, for chronic subjects, and less so for head movements. This is a balance disorder in performing gait tasks by chronic subjects (Sjostrom 2003). Other such results identified increased energy expenditure during standing for ankle and hip muscles as trunk-flexed posture (Saha 2007). There is a locomotion skill related to balance strategies in adolescents with scoliosis (Mallau 2007).
  b. Low back pain subjects showed more postural sway and more posterior center of foot force plate stability positioning, and less balance on one foot with eyes closed than normal subjects (NN Byl 1991). Also, chronic low back pain subjects were compared to normal control subjects under postural control strategies of the pelvis and trunk that exhibited increased postural sway; 3D movement strategies were documented with markers and cameras to estimate angular displacement, and showed a higher postural sway was correlated with rotational over more lateral flexion to adjust balance (Van Daele 2009).
  c. Chronic spinal cord lesion patients had a high correlation with strength, balance, spasticity, and age with walking performance (Scivoletto 2008).
  d. While phasic patterns and angular spinal displacements were closer to normal for patients with nonspecific back pain, they exhibited higher degrees of stride-to-stride variability from increased fluctuations of thoracic and pelvic oscillations, creating less than optimal gait patterns, and should be part of rehabilitation (Vogt 2001).
  e. Vestibular activation with galvanic stimulation causing subject sway backwards showed in EMG bilateral activation in erector spinae, gluteus maximas, biceps femoris, soleus, and intrinsic toe flexor muscles, and a sway forward with reversed polarity indicating latencies in lower limbs for control of the back when sitting and standing (Ali 2002).
  f. Elder subjects chose lifting strategies based on their hip and knee extensor strength, and could be susceptible to falls and fractures, which could be identified by muscle testing with a leg dominant lifting strategy teaching (Puniello 2001).
  g. Surface EMG measurements in cervical muscles during neck motion indicate that the stiffness of the cervical spine may indicate neck disorders in the elderly (Cheng 2008).
  h. Gluteal muscles were shown to be more effectively activated by stimulating the proprioceptive mechanisms during walking of chronic low-back pain sufferers using labile support with "balance" shoes relative to barefoot subjects as measured with EMG recordings of gluteus maximus and medius muscles (Bullock-Saxton 1993). This can lead to better shoe product development, e.g., the use of soul-slip in determining the value of a type of shoe for s specific need of human locomotion conditions.
5. Horse training
  a. Measurements of velocity-dependent changes in stride-length and stride-frequency with a French saddle horse and rider on a track and on a treadmill were made using video gait analysis. Linear relationships between stride-frequencies, increasing on the track relative to the treadmill at higher speeds, and on the walk, stride-length was significantly shorter on the track relative to the treadmill; this indicated a strong linear relationship between length and speed for both conditions, but without effects observed from incline (Barrey 1993).
  b. Incline motion of horses, requires additional power to elevate the body mass, as measured by foot-on and foot-off times during high speed locomotion over the ground, and other stride parameters (stance duration, protraction duration, stride-frequency, and duty factor). Hence, stride frequency increased during incline galloping along with hind-limb duty factor increases (Parsons 2008).
  c. The incline galloping horse energy requirements for up-slope locomotion are explained with the additional work to move a CM motion up slope in PE, with mechanical energy estimated from body and foot instrumentation, as well as vertebrae sensors. The rotational (roll, pitch, heading, and linear kinematic parameters (step, velocity and acceleration in KE) showed little body changes in the motion, but most of the affects were coming form hind limb stance (Parsons 2008a).
  d. This work in incomplete, because the issues of the rider's balance relative to the horses balance under track and treadmill situations is more complex, but it is also clear that the energy conservation and PE, KE modeling are good models for assessment of Track and Balance in horse rider applications.
6. Other locomotion products for elderly care, dementia, and Parkinson and Alzheimer diseases, suffering from problems with balance and walking, showing increased improvements with high levels of physical functioning (e.g., walking, Baker 2010).
  a. Single leg balance tests of 40 elderly subjects were performed in two groups (with/without a history of being fallers), and performed with/without eyes open, when related to gait tasks of holding/not-holding a water glass while walking, showed that falls, being defined as number of times the suspended foot touches the ground, occurred 3-times more often for known fallers (with eyes open, and twice as often with eyes closed), but little differences were found in gait parameters (cadence, speed, stride, step-time, and single-support time), indicating that balance is a more critical feedback element in detecting walking disorders, and in planning physiotherapy to prevent falls (Toulotte 2006).
  b. Gait disorders and cognitive failure in the elderly may influence each other to increase the risk of falling. Different cognitive profiles were performed on three groups of subjects living at home and free of gait impairments (e.g., control subjects, subjects with mild cognitive impairment (MCI), and subjects with Alzheimer's disease, AD). The subjects were tested on a neuropsychological battery of tests and a motor evaluation (with dual and single tasking). Gait profiles varied between the three cognitive groups and in the dual tasking, the MCI and AD groups were quite similar. Hence, various examples of cognition abnormalities can be discovered with locomotion analysis (Gillain 2009).
  c. Body unloading in upper/lower leg muscle activation on treadmill walking showed load (unloading) sensitivity of Gastrocnemius EMG as a change to existing thresholds for Parkinson's disease subjects (Dietz 1997).
7. Improvement in video gaming products, for better incorporation of body motion, to enhance achieving successful game scoring.

Metric Simplification from Stress Pressure Measurements

Leg intramuscular pressure has been identified as providing useful muscle function during human locomotion (Ballard 1998), but the explicit muscles and their functions that related to dynamic, locomotion has not been identified. Thigh and calf midpoint muscle cross-sections provide a simplification to locomotion metric measurements. An analysis of the accessible regions, used by Solinsky with Hg loop sensors, can provide further insight (Solinsky U.S. Pat. No. 7,610, 166). The example of lower body muscles summarized in FIG. 4 (answers.com 2010), can be divided more completely into six muscle group regions (below by number): the Hip (Iliac, Lower Extremity), Thigh, Knee, Leg (here used as calf muscles), Ankle, and Foot, with some muscles operating in multiple regions as measured in cross-sections of the Thigh and Calf limbs. The goal of the measurements is to capture a part of the muscle actions to infer further energy contributions, e.g. to Balance and Track locomotion through the integration of Power (P) as an energy expenditure rate. The muscle groups contributing to the measurements are discussed next (Gray 1918), and identify all of the functionality (sub-grouping by letter) for each numbered muscle groups present, but with a focus on identifying the dominant muscles shown in cross-section drawings for Thigh Gray432 and Calf Gray440 (Gray432, Gray440 2010), which are useful for determining Track and Balance metrics with loop muscle-pressure (P) sensors; here the relationship between pressure and muscle action forces (A) is made with a nonlinear mapping function, $\mathfrak{F}$. Note that many muscles listed have multiple functions.

The complete muscles present in the lower body are shown below, as a collection of web summaries and reprints, with possibly some overlap in nomenclature. The purpose in the discussion is to show the plausibility of the integrated analysis approach, but has a caveat to not represent the muscle details in connecting one region to another, e.g., knee extender to hip flexor, but more so to define regions of important muscle expenditures of energy. Note, dominant muscle names are highlighted in italics (Gray, Anatomy 2010), with bolded-italics for dominate cross-sectional size in the thigh (Gray432 2010) and calf (Gray440 2010) and also appear in later figures. Functional locomotion importance is numbered in bold from 1 to 6 (for Hip Hn, Knee Kn, Foot Fn, and cross-muscle region utility is simply underlined as $\underline{Hn}$, $\underline{Kn}$, $\underline{Fn}$ (answers.com 2010)):

1. The Hip acetabulum of the Pelvis bone has joint muscles for:
   a. Lateral (external) rotation {H1—Gluteus maximus, H2—Quadratus femoris, Obturator internus, H4—Gluteus medius/H5—minimus, Iliotibial tract [Iliotendinous, H6—Iliospoas (psoas major)], H3—Obturator externus, Priformis, Sartorius}
   b. Medial (internal) rotation {Semimembranosus, Semitendinosus, Gracillis, Sartorius, and Popliteus}; here lateral ventral muscles for balance being stronger than medial rotators
   c. Extension {Gluteus maximus/medius, Adductor magnus, Piriformis, Semimembranosus, Semitendinousus, Biceps femoris/longhead}
   d. Flexion {Iliospoas, Tensor fascia latae, Pectineus, Adductor longus, Adductor brevis, Gracillis, Rectus Femoris, Sartorius}
   e. Abduction {Gluteus medius, Tensor fascia latae, Gluteus maximus, Gluteus minimus, Priformis, and Orbturator internus}
   f. Adduction {Adductor magnus/minimus, Adductor longus, Adductor brevis, Gluteus maximus, Gracillis, Pentineus, Quadratus Femoris, Obturator externus, and Semitendinosus}
2. The Thigh femur bone has nine major anterior and posterior muscles (14 total), and muscles of functions for adductors, with the majority acting on the hip (e.g., $\underline{H2}$), leaving muscles for extensions and flexions of the knee ($\underline{K1}$, $\underline{K2}$, $\underline{K3}$, $\underline{K4}$, $\underline{K5}$, $\underline{K6}$):
   a. Anterior {Quadriceps ($\underline{K1}$) Femoris ($\underline{H2}$)[Rectus femoris, Vastus intermedius, Vastus medialis, Vastus lateralis], Sartorius}
   b. Posterior {Biceps femoris ($\underline{K5}$), Semitendinosus, Semimembranosus, and Popliteus}
   c. Lateral rotation (really knee flexion and hip extension) {Biceps femoris longhead (caput longum)/shorthead (caput breve), Tensor fascia latae (extender and flexor for stabilization) ($\underline{K2}$)}
   d. Medial rotation {Adductor magnus/minimus, Adductor longus, Adductor brevis, Gracillis, Pectineus}
   e. Extension {Quadriceps Femoris, Tensor fascia latae}
   f. Flexion {Semimembranosus ($\underline{K3}$), Semitendinosus ($\underline{K4}$), Biceps femoris, Gracillis ($\underline{K6}$) Sartorius, Popliteus, and Gastrocnemius}
3. The Knee joint (with patella bone or "knee cap") has muscles for:
   a. Lateral rotation {K5—Biceps femoris, and K2—Tensor fascia latae}
   b. Medial rotation {K3—Semimembranosus, K4—Semitendinosus, Gracillis, Sartorius, and Popliteus}
   c. Extension {K1—Quadriceps and Tensor fascia latae}
   d. Flexion {Semimembranosus, Semitendinosus, Biceps femoris, K6—Gracillis, Sartorius, Popliteus, and Gastrocnemius}
4. The Leg's tibia (shin) and fibula bones have (14) major Calf muscles, with anterior and lateral foot muscles (F1, F2, F3, F5, F6) for functions:
   a. Anterior Deep peroneal {Tibialis anterior ($\underline{F1}$), Extensor digitorum longus ($\underline{F2}$), Peroneus teritus, Extensor hallucis longus ($\underline{F3}$), Extensor digitorum brevis}
   b. Lateral Superficial Peroneal {Peroneus longus ($\underline{F5}$)/brevis ($\underline{F6}$)}
   c. Posterior Superficial Tibial {Three Gastrocnemius, Tendo maximus plantaris, Soleus}
   d. Posterior Deep Tibial {Popliteus, Flexor digitorum longus, Flexor hallucis longus, Tibialis posterior}
5. The Ankle, similar to the knee, has many pass through muscles (for the foot $\underline{F1}$, $\underline{F2}$, $\underline{F3}$, no Triceps surae, $\underline{F5}$, $\underline{F6}$) and functionally for:
   a. Tibialis anterior ($\underline{F1}$)
   b. Extensor digitorum longus ($\underline{F2}$), Extensor digitorum brevis, Extensor hallucis longus ($\underline{F3}$)
   c. Flexor digitorum longus,
   d. Peroneus longus ($\underline{F5}$)/brevis ($\underline{F6}$), Peroneus tertius
   e. Tendo calcaneus, Tibialis posterior, Tibialis anterior
6. The Foot has many bones and muscles mostly from the Leg (Calf) for:
   a. Dorsi-flexion {F1—Tibialis anterior, F2—Extensor digitorum longus, and F3—Extensor hallucis longus}
   b. Plantar-flexion {F4—Triceps surae, F5—Peroneus longus/F6—brevis, Flexor digitorum longus, and Tibialis posterior}
   c. Pronation {Peroneus longus/brevis, Extensor digitorum longus, and Peroneus tertius}
   d. Supination {Triceps surae, Tibialis posterior, Flexor hallucis longus, Flexor digitorum longus/brevis, Tibialis anterior}
   e. Abductor hallicus/digiti minimi As described herein, this muscle outline and linking between groups show a strong correlation between the thigh and calf cross-section muscles and the functions of locomotion for TD and TO occurring during the periodic motion of FIG. 7. Using Grays Plates 432 (thigh) and 440 (calf) cross sections, one finds the dominant muscles listed above in multiple cross-sectional sizes (Gray432 2010, Gray440 2010). One of the six dominant hip muscles (H1—Quadratus femoris) is also present in the thigh region, as well as all of the six dominant knee muscles (K1-K6).

This implies that the thigh muscle cross-section will be of value in knee lifting and hip swing aperiodic locomotion activities, and the calf muscle cross-section region also has a similar connection with muscles in the ankle and foot for up to the toe-off functionality of periodic locomotion, being F1-F3, and F5, F6, and possibly also in heel-strike measurements. This leads to the potential utility of muscle-pressure measurements in inferring locomotion dynamics of body force exertion, being derived from optimal use of energy expenditures. Similar conclusions are possible for arm and forearm muscle cross-section pressure measurement applications.

Summary of Simplified Human Locomotion

The body locomotion components can exhibit both periodic and aperiodic dynamics, being quite different from the articulated, linear mechanical motions of biomechanical engineering models using bones, tendons and muscle components, such as the motion defined in FIG. 1 respectively as angular and translation motion. Here, Balance refers to the ACM 3D motion, involving mostly upper-body, changing inertia actions in angular coordinates (angular momentum) of roll, pitch, and yaw, where Track refers to a forward CM 3D motion, along a footpath defined by foot placement at each step, involving mostly lower-body, thrusting action translating total body weight inertia in linear coordinates (linear momentum) of forward step-length direction, heading, and height.

FIG. 3 shows a sleeve method (Solinsky U.S. Pat. No. 7,610,166, FIG. 5 and FIG. 6) of measuring body thrust forces without accessing the full body motion, by using an Hg loop sensor (Solinsky U.S. Pat. No. 7,610,166, FIG. 7) placed on the calf, but in the example systems and methods described herein the translation of the orientation and acceleration forces are now being directly sensed on the muscles of the legs, and not on the small of the back, and sensors on the feet are not required. The thrust/compression leg force A (=M/a) for body mass M, is measured by the acceleration a, being present when the feet are thrusting on the ground (a≠0). In the '166 patent, the sleeve also has a series of individual, interwoven strip sensors around the calf to determine calf changes in location from sensed Earth's magnetic field vector orientation B (using magneto-resistive materials) and from leg muscle force-exertion as pressure, P, inferring measurements of A (using stress-resistive materials), being formed as electronic signals (Solinsky U.S. Pat. No. 7,610,166, FIG. 8), which potentially can be replaced in the systems and methods described herein with more point like sensors to increase measurement modality.

From the FIG. 1 description, the upright mammal locomotion of humans moves the complete mass forward in a linear sequence of steps along a footpath that are spaced in time as left (L) and right (R) steps in a stride, with distance between contacts as a gait cycle description of a L/R step set. Walking speed (ambulation) is the distance traveled by each stride, times the cadence or rate of steps per minute, where normal human walking speed averages 1.5 m/sec or 120 steps/min of 1.5 m stride lengths (i.e., 2-steps/stride). Each step creates a linear momentum sequence, with heading changed by the change in direction from the foot placement, or from momentum changes by the forward speed changing.

The periodic gait cycle time ends with the same starting foot re-placement on the ground (62% of a gait cycle is in the stance phase, as a slightly asymmetric cycle). This cyclic motion recovers about 60% of the energy used in the two-leg 'pendulums' and from ground reaction force bounce. Stride length changes slightly with the log of the walking speed (e.g., 0.7 to 2.0 m, for a speed of 0.5 to 2.5 m/sec), and the periodic cadence changes linearly with the speed (80 to 170 steps/min for the same range). The modeled walking as a continual double pendulum is trading off PE of the rising mass for KE of the forward and up/down motion, and is very efficient. Running changes relative to walking, with a lower mass center, when the leg is vertical, because the impact of landing is absorbed by a bending in the leg (i.e., at the thigh-calf knee joint), and storing and dissipating energy in the muscles and tendons as elastic energy, added to the PE and KE terms.

During this periodic Track motion, the limbs, torso, and appendages of the mammal are involved in a complex, aperiodic motion that drives the moving appendages to create contact with the ground with changes in the Track, represented by the angular momentum sequence of the entire body 3D inertia (I), which has a conservation over longer time periods, but with complex deviations over short time periods that allow for the Track changes. The mammal neural control of this linear and angular momentum is based on a pre-trained, primitive brain function for predicting action based on sensory perception. These actions appear in the muscle flexing and appendage motion for footfall placement that are measurable with physical pressure sensors and appendage location sensors, relative to the ground, as determined by a gravitational force direction on the CM. The location of the limbs in extensions and changes of angular momentum, when the swing and stance phases transition, could be measured with an analysis of the limb location using changes in the original magnetic field sensing described previously.

There is little prior work in biomechanical modeling, gait analysis, and lower muscle measurements and analysis to promote a representation of a proprioception locomotion model that includes the periodic and aperiodic cycles of the limb motion and muscle neural firings (i.e., from both brain and local oscillatory directed action), which is the dominant observable needed in current applications solving problems in diagnosis, therapy, and assessment of health conditions and in physical training.

Figure 9:
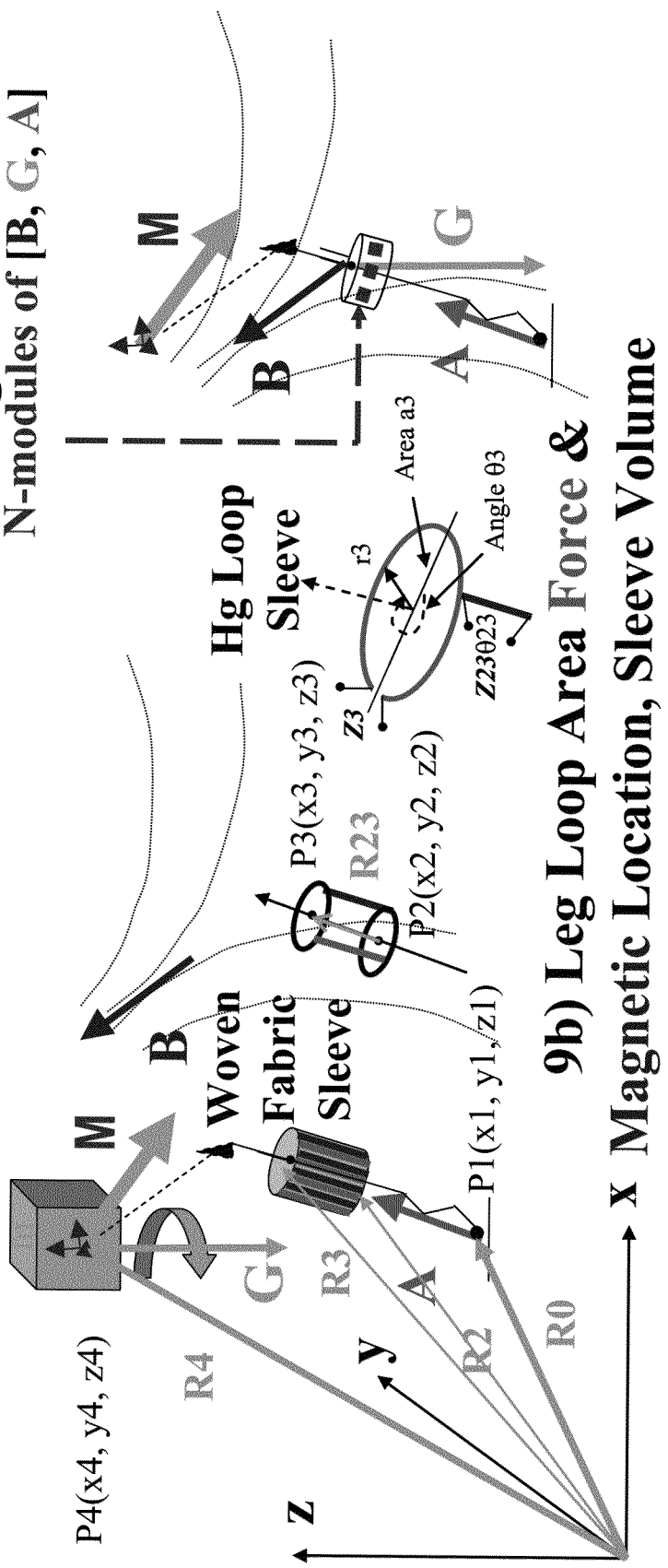
FIG. 9 shows a) previous system for back and leg-loop sensing, b) being migrated to leg-only sleeves with loops, and c) as bands of multiple sensor modules (MSM).

The approach to using a collection of individual sensors on a band placed on the leg is the migration of the use of a mercury loop sensor from previous approaches for muscle pressure measurements of blood flow, indicating muscle action (Solinsky U.S. Pat. No. 7,610,166) as shown in FIG. 9, and incorporates the limb properties, as measured when surrounded by a band sleeve that is placed in circumferentially contact with the limb skin for muscle pressure measurements (with or without a thin film membrane for cleanliness or static friction improvement). The approach also replaces the Earth's gravitational and magnetic force field measurements from being measured on the small of the back with a set of 3D vector sensors into a band of multiple 2D ("flat") MEMs sensors, also being in circumferential contact with the limb for location measurements relative to the ground or other firm placement that defines the level foot location during calibration and during gait cycle placements for assessment of Balance and Track metrics. This is accomplished using algorithms that sum 2D vector sets with calibration data into a full 3D representation, similar to the already mentioned sensing of the body in the small of the back, but here it is a 3D location of each locomotion limb "volume centroid," and in an independent manner, every band is attached around instrumented limbs having muscle pressures being measured.

The important advantage of limb sensing in the systems and methods described herein is that the thrust force acceleration from the pressure sensors is being measured exactly in the same physical component of the body thrusting limb, with a simultaneous measurement of the local gravitational 3D accelerator vector, relative to this field and can distinguish between the gravitational component of the KE element coming from thrust dynamics and from the PE element from gravitational pull. The magnetic field orientation, from the 3D construction of the 2D sensing MSM set, locates the rotational and joint motion dynamics of each limb in 3D dynamic space, such as from the calf, as well as from the translation motion from the hip and thigh, as the two pendulums in the double, inverted pendulum.

Figure 10:
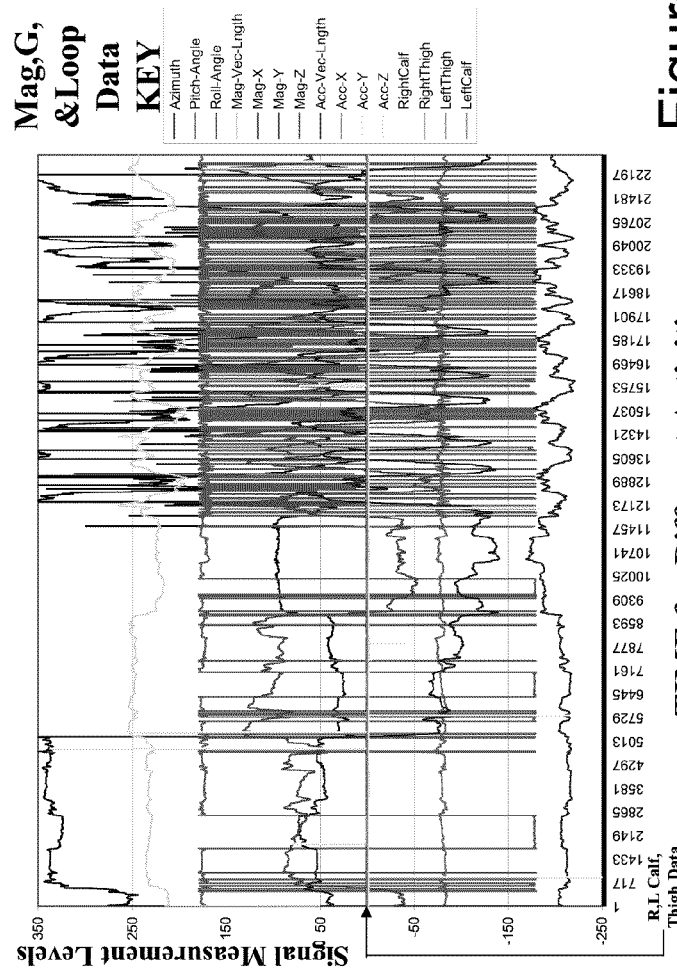
FIG. 10 shows new digital data collected in format of previous back and calf sensors.
Figure 10:
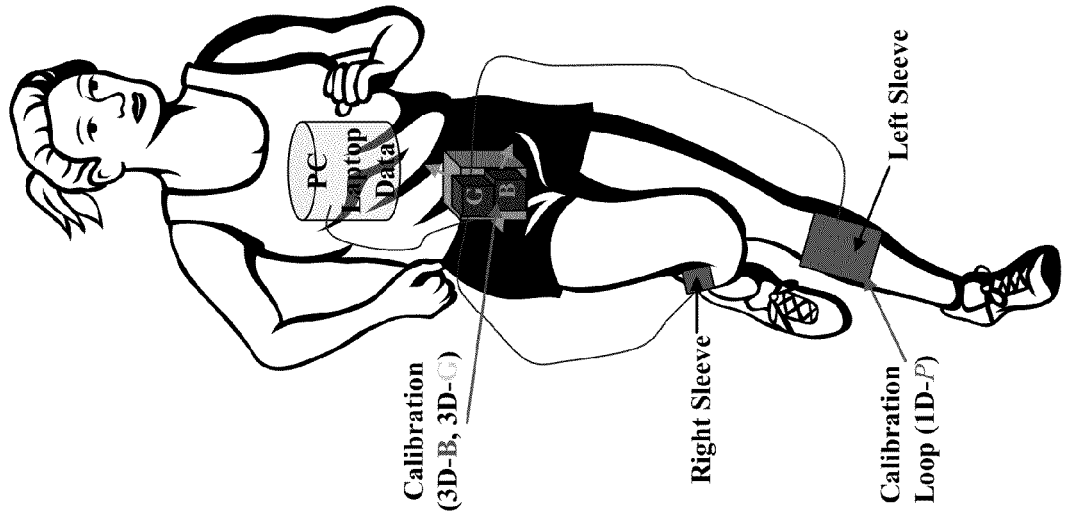

FIG. 10 shows data collected from loop bands placed on the left and right legs (L/R) shown in the sketch, where the sleeve uses the original Hg loops. The 3D B and G sensors, placed at the back, also show data as a function of time and under motion of calibration, walking, and running.

Figure 11:
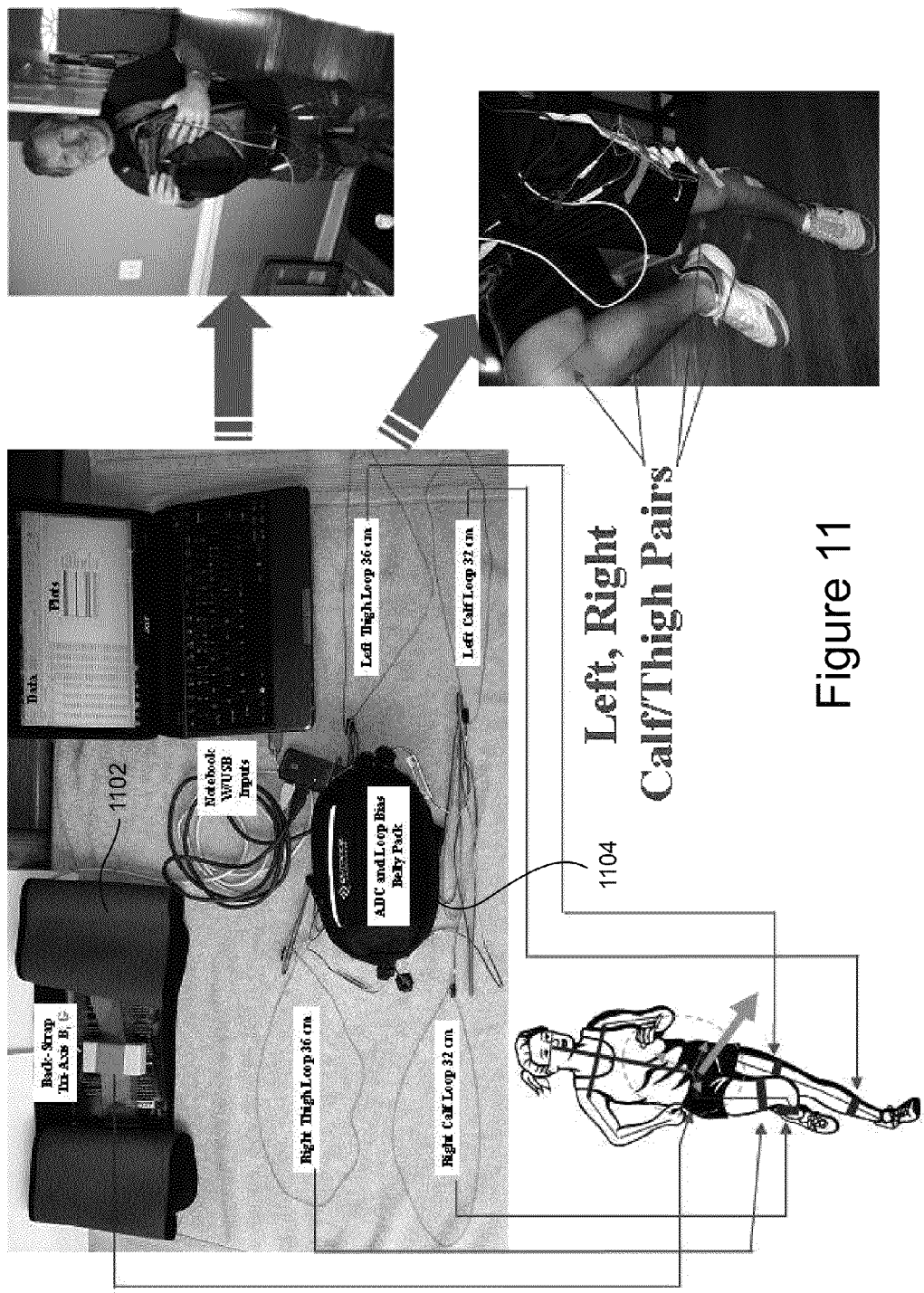
FIG. 11 shows elements for FIG. 10 (back, calf-loop sensors) w/additional thigh data.

FIG. 11 shows a further modification using the portable data recording system of FIG. 10, and the specific Hg loops are shown for both L/R calf and thigh locations at the cross-section midpoint. Thus, the FIG. 11 arrangement can be used to make synchronized measurements on both calf and thigh. In this figure, the back strap 1102 includes sensors for making 3D magnetic and gravitational measurements. The belly pack 1104 measures the four loops around the calves and thighs, each loop in this example embodiment including liquid mercury.

Figure 12:
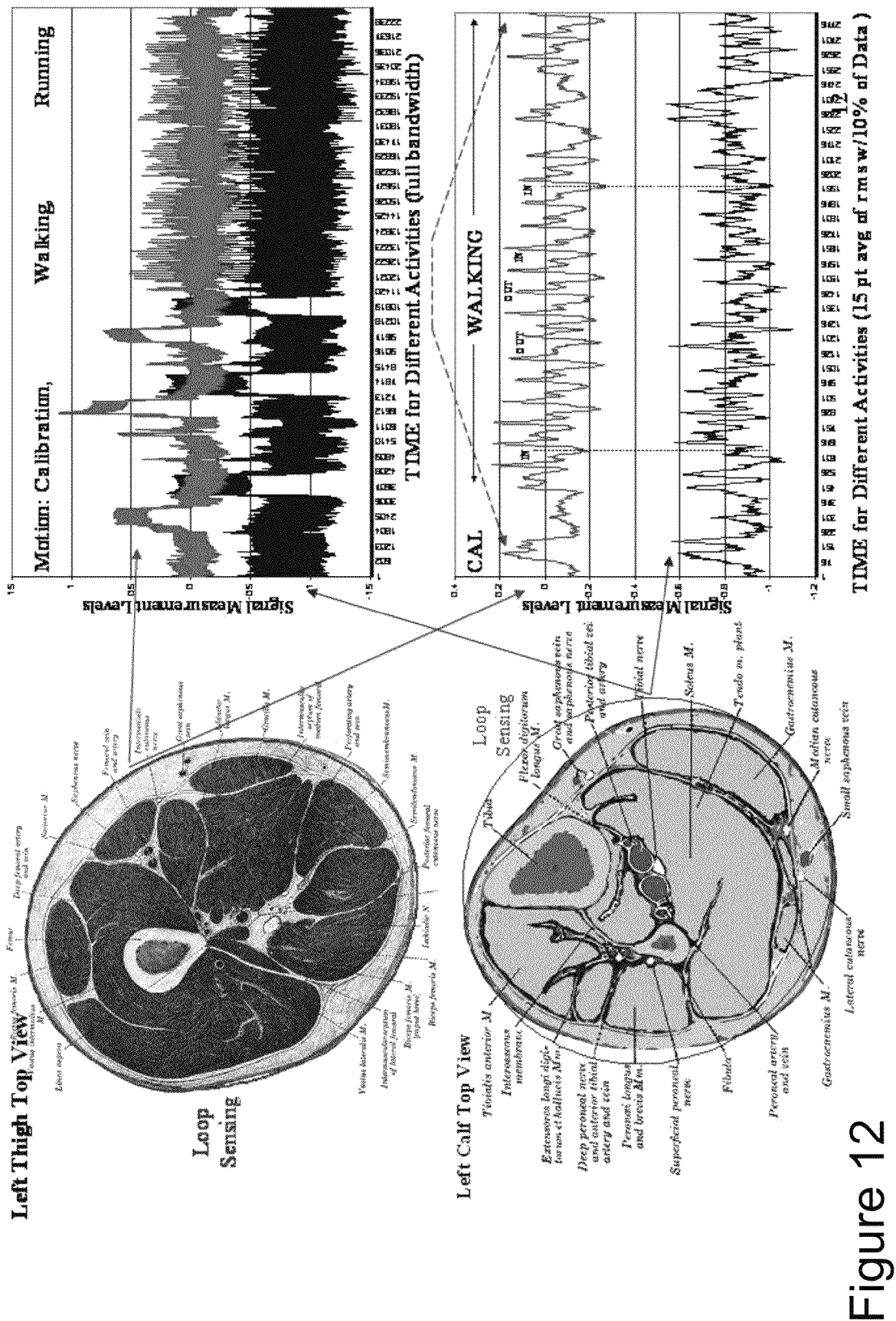
FIG. 12 shows prototype FIG. 11 left thigh/calf muscle cross-sections and loop pressure data, with 60-Hz AC noise contamination (upper) and digital filtering (lower).

FIG. 12 shows the muscle components represented in these cross-section measurements from the encirclement by the Hg loops of the cross-sectional muscles identified in (UL/LL) Grays 440/432 drawings. Clearly many muscles will contribute to the changes in pressure, but no reliable method exists for measurement of force production of individual muscles during locomotion (Ballard 1998). Intramuscular pressure (IMP) is considered to be one approach, whereas EMG is considered to not be an approach. A subset of just the loop data for the left thigh and left calf are shown in the UR/LR sides of the figure, and collected data for the three activities of FIG. 12 shown on the UR, are in a close up of the walking region on the LR side. The UR data has a 60 Hz component being measured from the magnetic "antenna" nature of the loops, which is filtered out from the digital data on the LR side of the figure. Note that in the FIG. 12 data examples, the relative gait cycles of the walking data has both in and out of phase relationships from the Calf and Thigh, as shown by the vertical lines.

Figure 13:
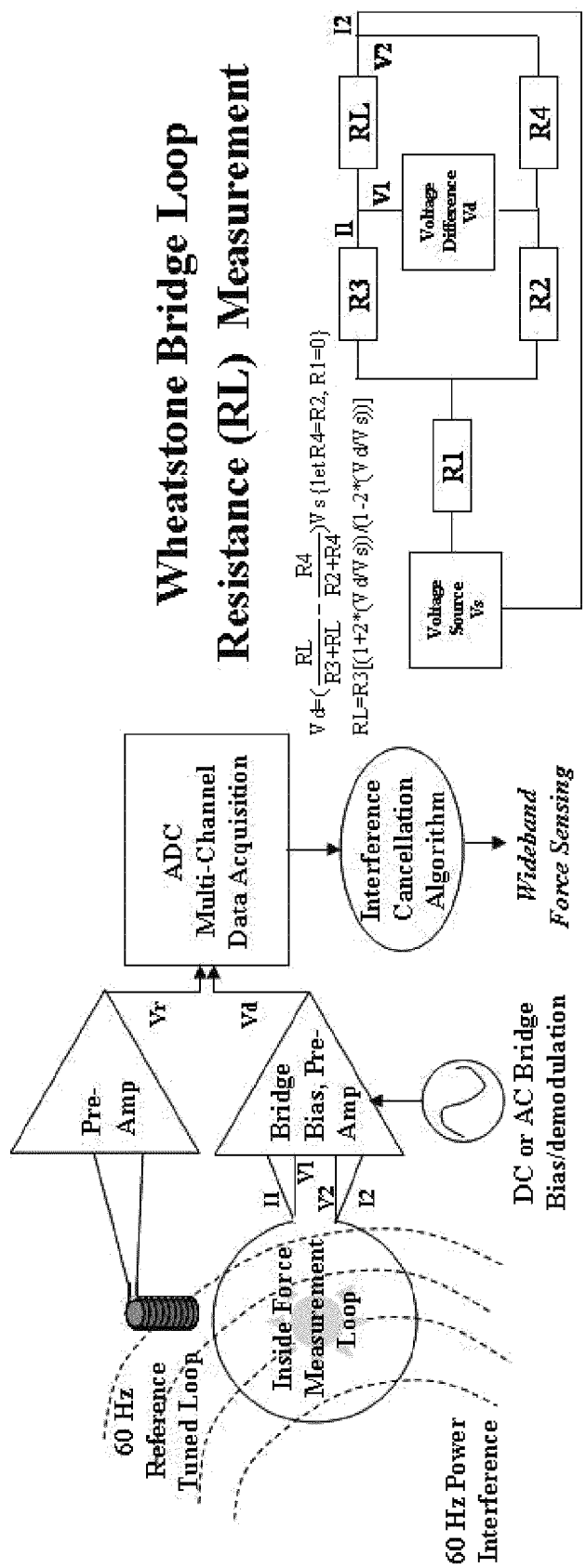
FIG. 13 shows loop measurement electronics, augmented by a noise removal sensor.

FIG. 13 shows a typical analog circuit with a small magnetic sensor being attached outside the loop tuned to 60 Hz, in order to accurately remove the 60 Hz contamination. The algorithm for this sensor data to remove the 60 Hz interference is shown in the lower part of the figure using a Fourier method of coherent noise subtraction using a complex Fourier Transfer Function $TF_{dr}$.

Figure 14:
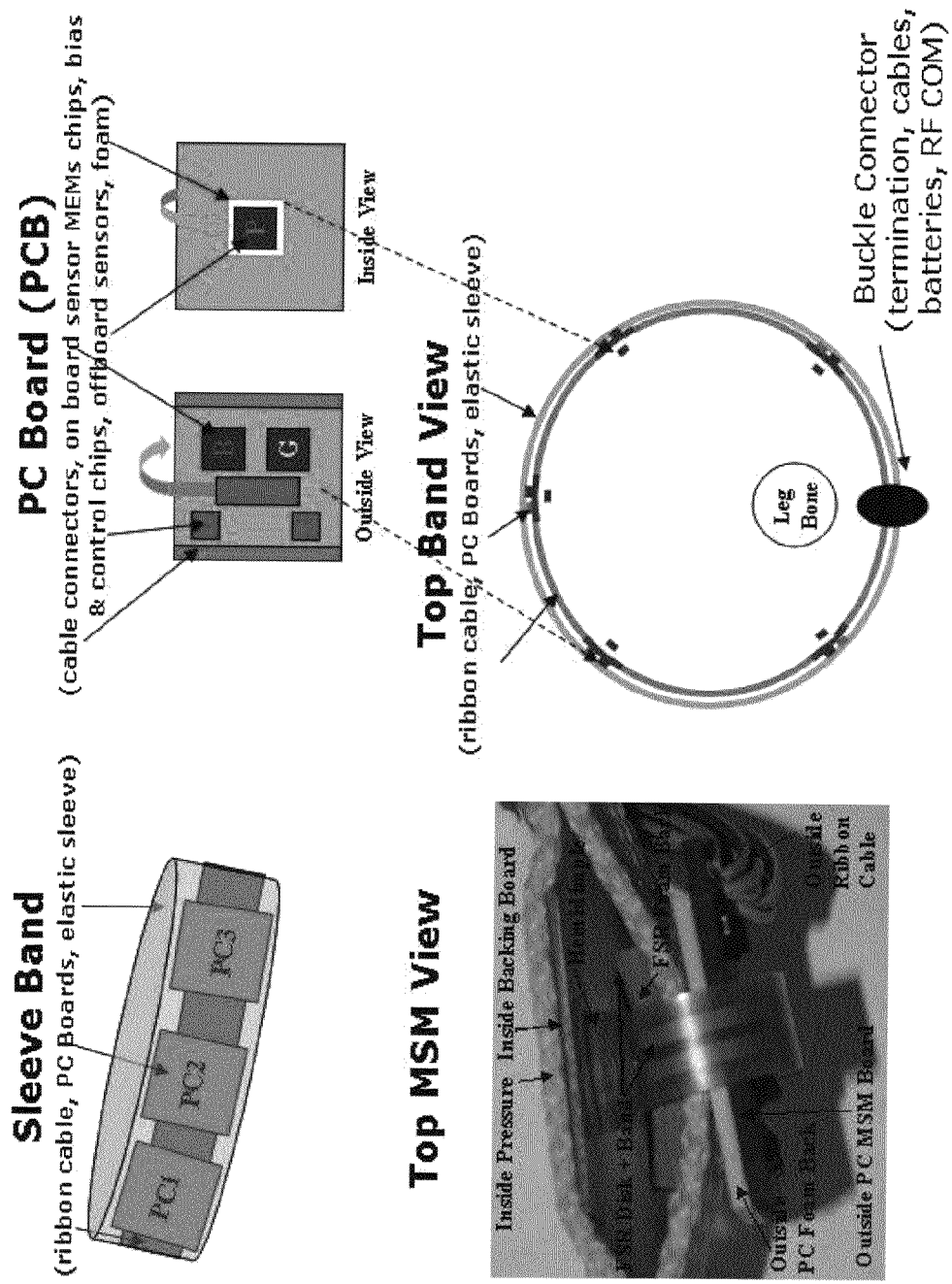
FIG. 14 shows the MSM module and sensor placement on the pre-production band.

FIG. 14 shows the sleeve band of FIG. 9 in more detail, with an individual printed circuit board (PCB) integrating the two 2D MEMs sensors with a single force sensitive resistor (FSR), being electronically measured with a circuit similar to the Wheatstone bridge shown in FIG. 13 for the Hg loop. Thus, the boards each include a magnetomer, a gravitomer (accelerometer) on an outer side and a force (pressure) sensor on the inner side. A buckle tightens the band. The pressure sensor may, for example, be implemented using a ribbon cable including carbon impregnated silicone rubber, for example, which changes resistance as pressure is applied.

Figure 15:
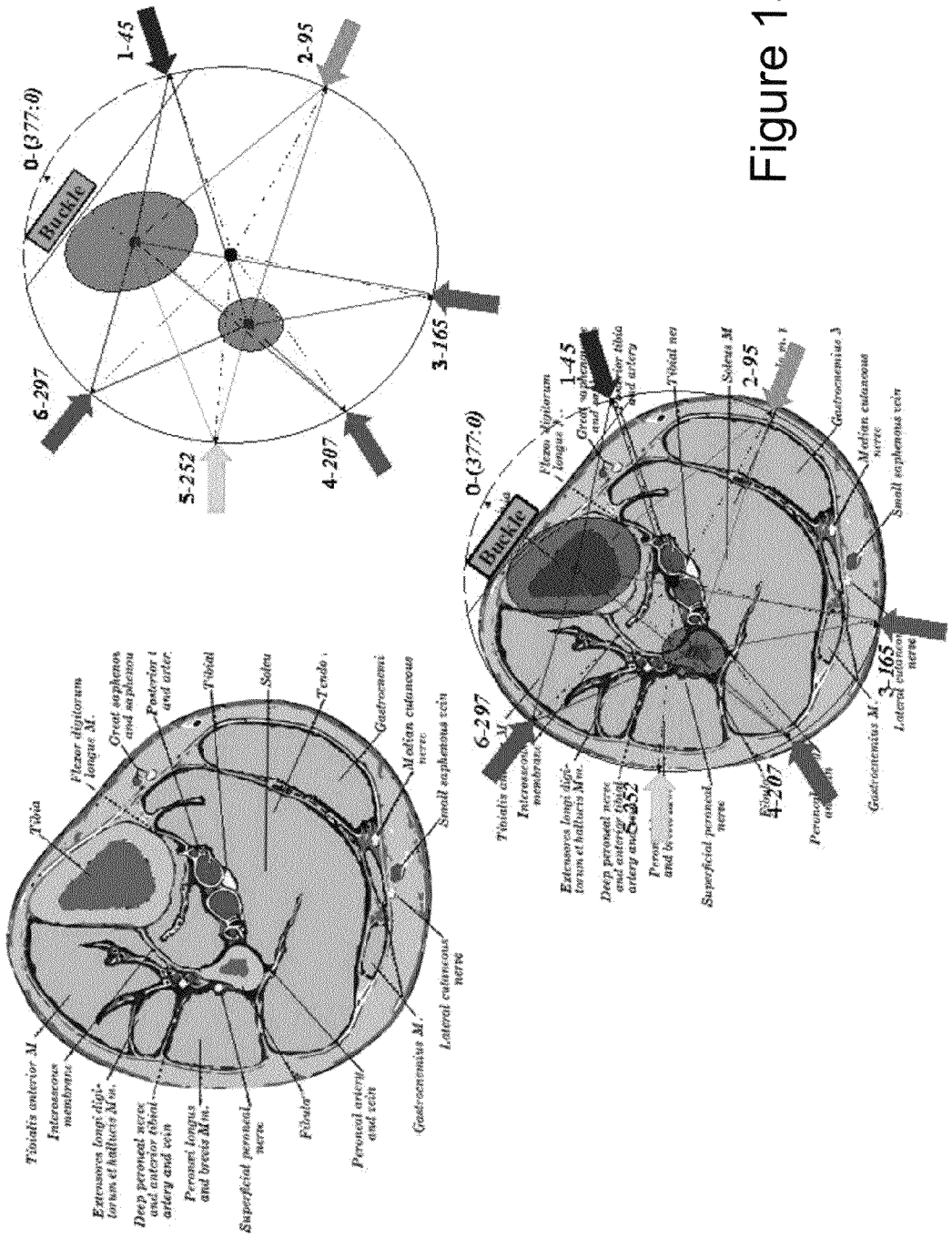
FIG. 15 shows left calf top view muscles (Gray440), w/6-MSM pressure location angle placements on an elliptical circumference about bone centers (UR avg. angle $\Delta\theta=59°$.
Figure 16:
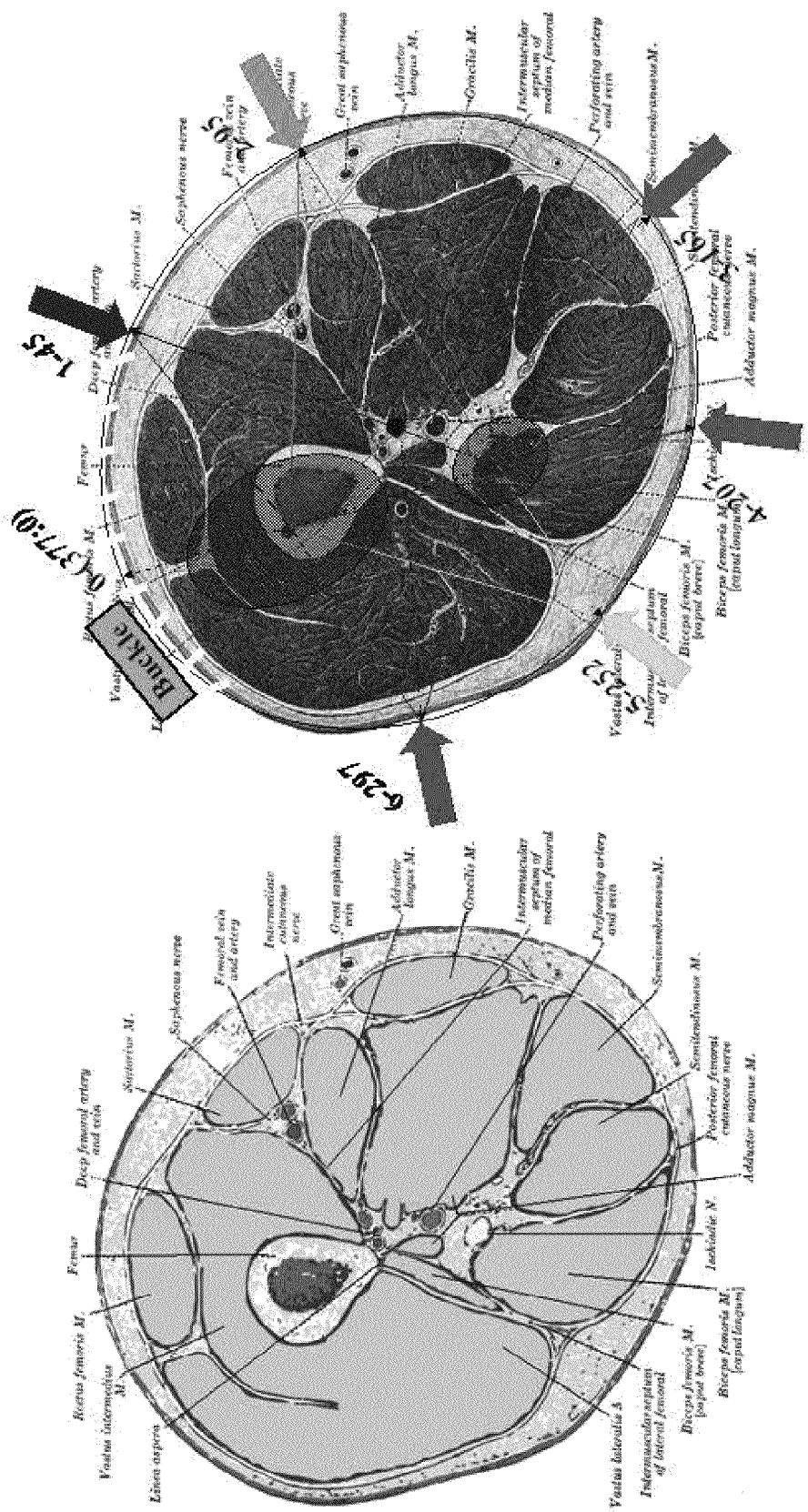
FIG. 16 shows left thigh top view muscles (Gray432), w/6-MSM pressure location angle placements similar to FIG. 15 about bone/ishiadic centers (R avg. angle $\Delta\theta=59°$.

The cross-section of the thigh and calf muscles (where the loop location measurements were sampled in FIG. 14), are reproduced in FIG. 15 (UL) for the calf (Gray440 1918) and in FIG. 16 for the thigh (Gray432 1918). FIG. 15 also shows an example of where the PCB FSR sensors are placed on the band (as arrows at band CW angle θ positions relative to the buckle placement on the leg), and encircles the muscles with specific pressure sensors measuring major muscle components. The six locations (UR) are referenced to an elliptical positioning foci about the two calf bones, with an angular separation placed with the six FSRs being on average at $\Delta\theta=59°$, when the buckle is also counted as a position, but without a pressure sensor, and is placed near the bone as a fiducial to the muscles of interest. The angular exposure of the pressure sensors encompasses the majority of the energy production regions in the muscles. FIG. 16 shows the same example placement approach for the thigh and a similar elliptical foci location about the bone and ishiadic nerve, with surprisingly the same average angular placement being also on the order of $\Delta\theta=59°$.

Figure 17:
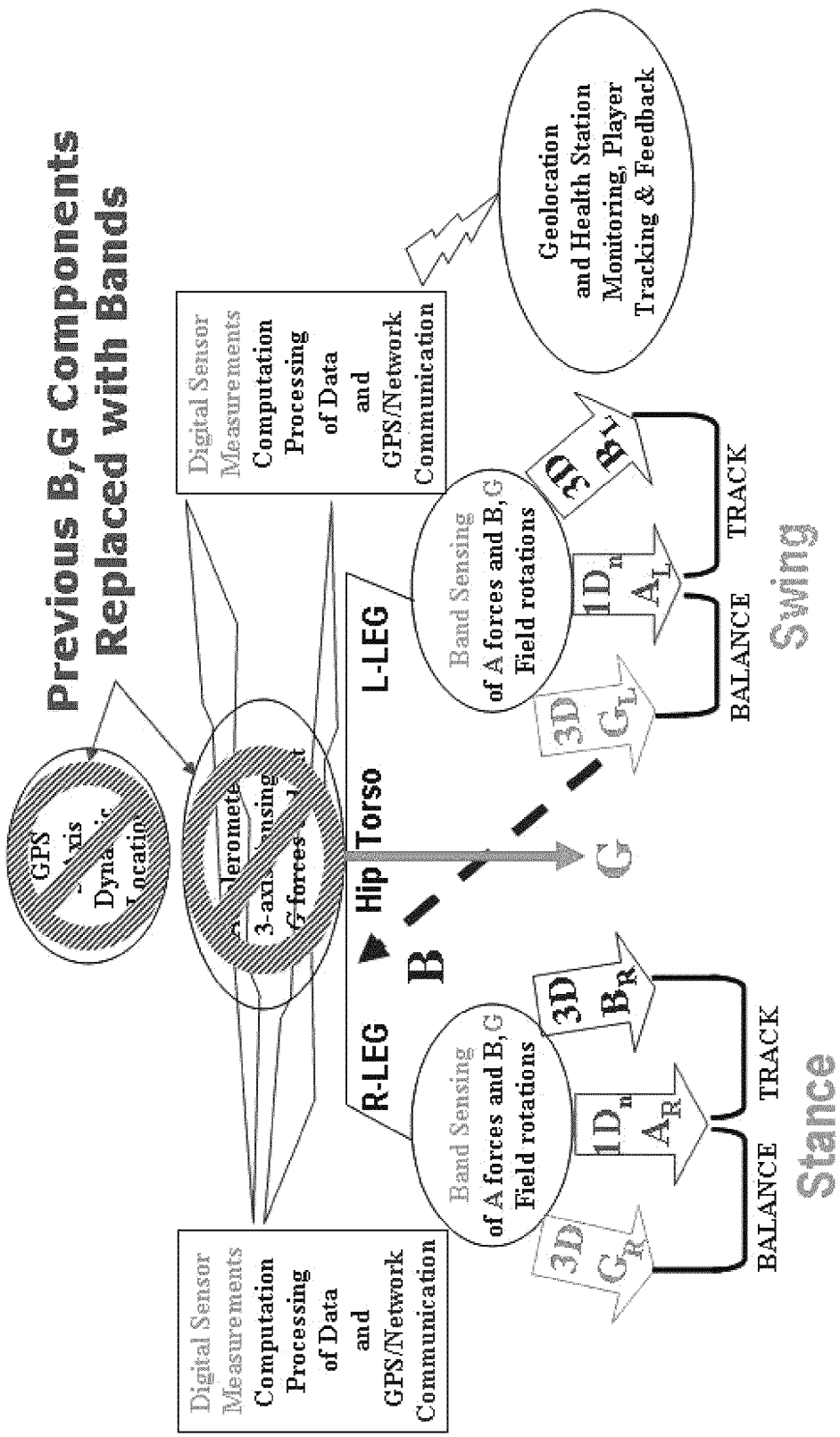
FIG. 17 shows previous system modified for RF band-to-band and laptop connectivity.

The complete system of gravitational and magnetic sensors with the loop pressure sensing is also migrated to the two-band system description of FIG. 17, where RF connectivity is used for interband connectivity, and the individual 3D vector sensing for magnetic (B) and gravitational (G) force fields are shown, along with the pressure inferred thrust acceleration (a); note the stance leg and the swing leg are in different sensing locations with relative angular and level changes between the L and R calves (and can also include the thigh band sets for Q angle and further refinement of Track and Balance, but not shown in the figure).

More specifically, in an example implementation, the buckles of the sensor bands contain electronics for, among other things, collecting data from the various sensors corresponding to pressure force (1D) and magnetic (3D) and gravitational (3D) field rotations. The data from the two buckles are combined to bring the sets of leg motion data into the gait motion data.

The FIG. 17 system also includes tracking which is provided, for example, using a GPS sensor incorporated in one or more of the sensor boards and/or in the buckle electronics. Tracking is useful where, for example, it is desired to provide sensing bands to multiple persons such as players playing a game (e.g., soccer, football, etc.). Tracking provides position information so that, for example, when two or more people interact, sensing band data can be properly associated with each of the interacting persons.

The FIG. 17 system can also provide feedback. Thus, one or more of the sensor boards may include a tactile feedback element so that a person feels a vibration, a jolt to a muscle, etc. when he/she gets out of balance, for example. Visual or aural feedback may alternatively or additionally be provided.

Figure 18:
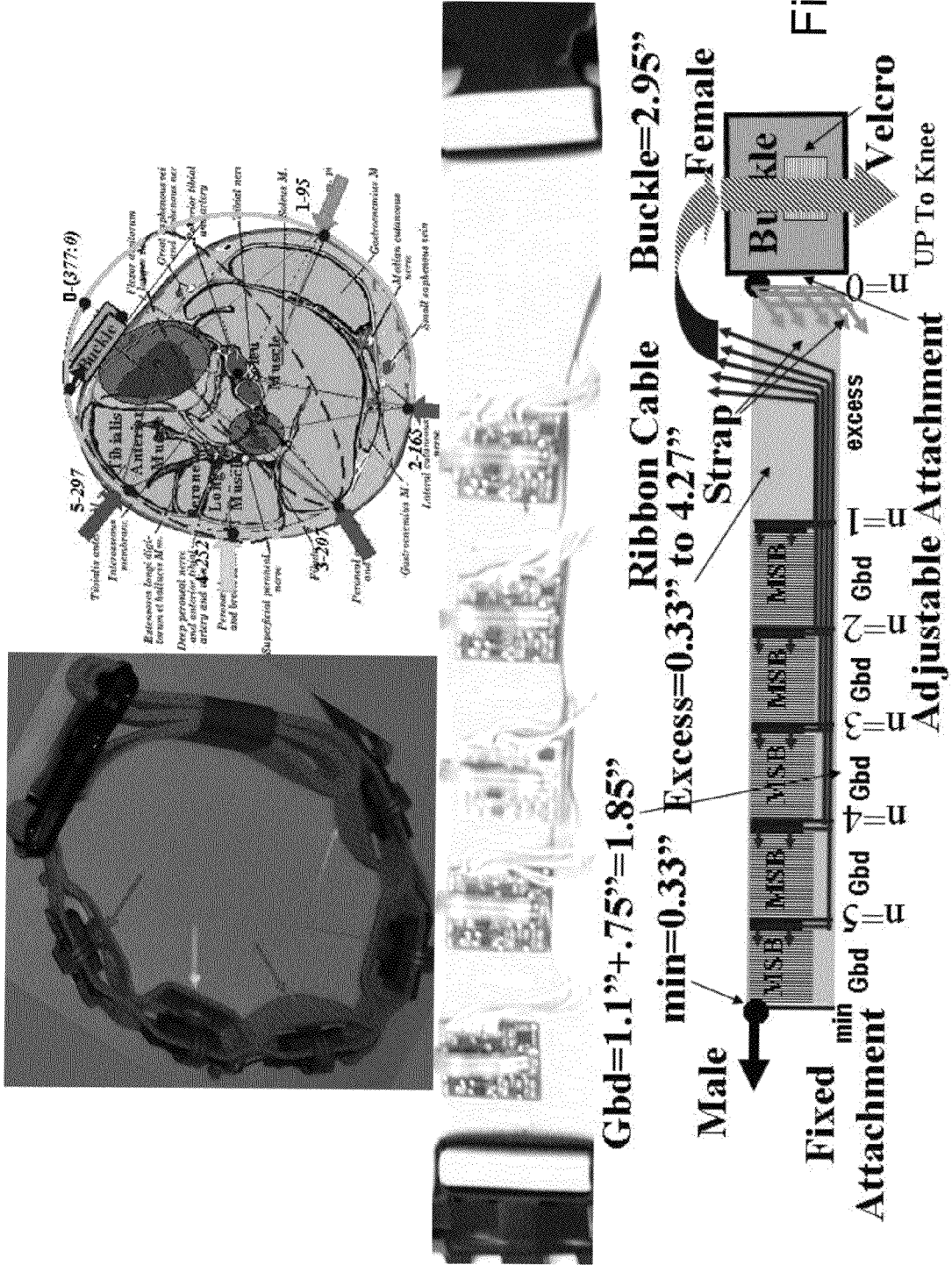
FIG. 18 shows calf band 5-MSM sensors (UL) at specific band-angles θ to FIG. 15 muscle actions (UR), w/picture-drawing layout and band closing buckle (also for power).

FIG. 18 shows an example band (UL) with five MSM PCBs, and the pressure muscle locations (UR) similar to FIG. 15 locations for six MSMs. Here, the changes in the band length, using statistics on human standard calf and thigh circumferences, allow for slight repositioning of a fixed band length of sensors, with a variable length between the last sensor and the buckle for adjustments (as a CCW MSM counting) to each individual limb. From the muscle locations in FIGS. 15 and 16, collected data has shown this adjustment feature to not be a problem in computing Track and Balance metrics. Most likely this is because of the larger muscles occupying a relatively large angular portion of the band circumference, relative to the measurement sample.

It is also possible to reduce the sensor count for boards containing the B, G MEMs, possibly to 3 or 4, and increase the pressure sensing board count to 8, for a reduction in system cost, but with an increase in muscle sensitivity and resolution. These embodiments are also being included, with the use of ICA data processing to measure pressure from the 'five' pseudo muscles of the dominant energy contributions. Note that in larger band length embodiment sizes, the 8 sensors can be spaced at lager intra-MSM distances, but at the same circumference angles.

FIG. 18 shows in the mid center of the figure, the actual example band MSMs and the buckle components, and a gap spacing indicated in the drawing at the bottom. Here, in the prototype, ribbon cables were used for MSM interconnection, power, and for band data collection, but in another embodiment, a flex circuit is used, and the MSM components are placed on the flex as additional boards with sensors on both sides. This form factor can also have the local and off body RF connectivity components, data digitization, metric computation and battery power enclosed in the buckle, with a second RF connectivity provided for remote, laptop wireless information display and recording of real-time action, as well as providing local band feedback stimulation signals on the leg.

Figure 19:
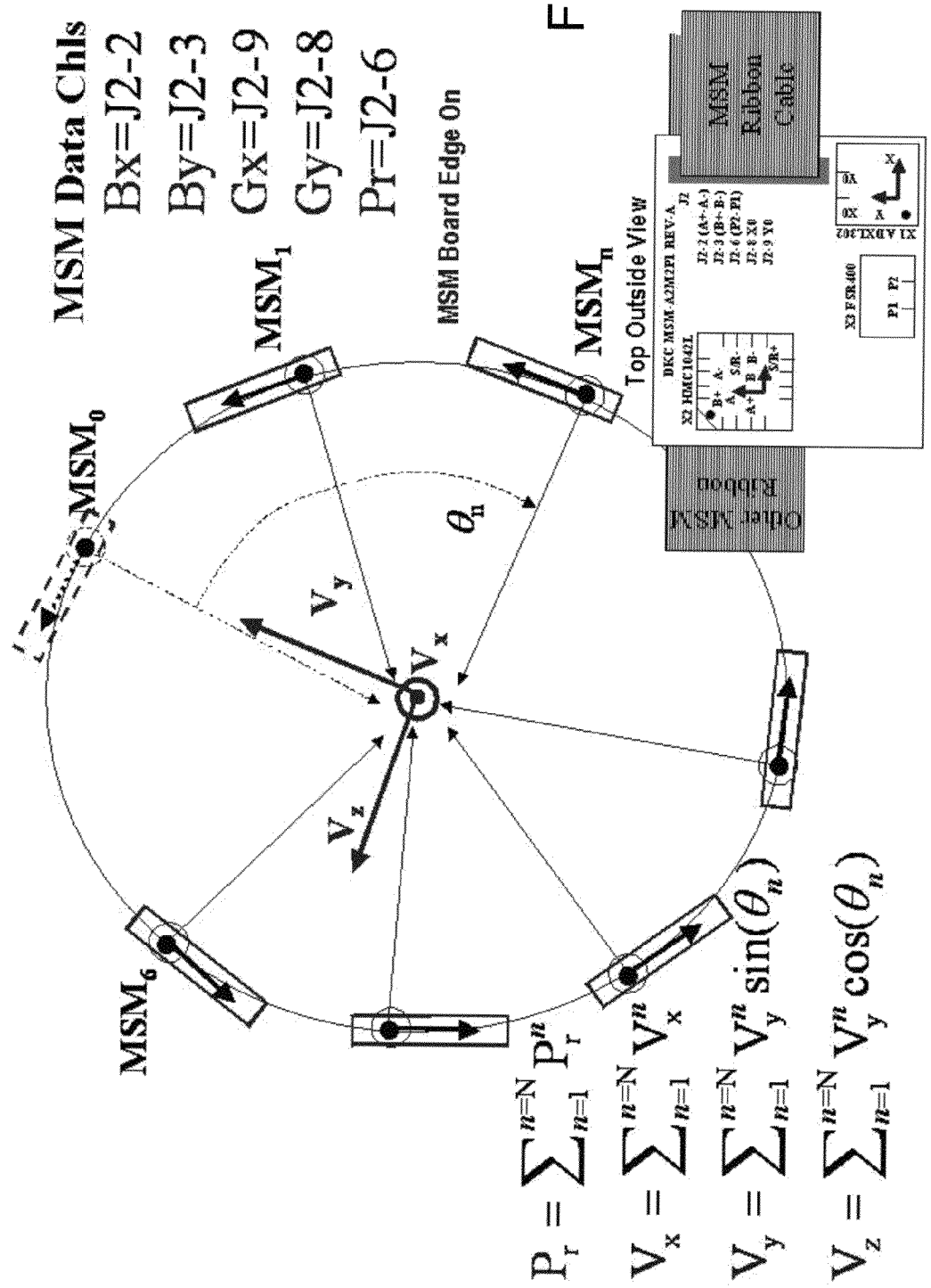
FIG. 19 shows multiple MSM 2D sensors digitally integrated for 3D measurements.

FIG. 19 shows the MSM board layout on the band, at similar angles to the locations of FIGS. 15, 16, and 18, and also shows an example algorithm summing the weighted 2D vectors of the MSM board placement (see figure inset, for Bx, By, and Gx, Gy as (X0Y0), and the FSR pressure sensing) for a 3D vector pseudo-sensing at the center of the band. The algorithm shows only the angle weightings for the CW angle positions in θ, but there is also a cos(φ) weighting from the calibration for the non-vertical alignment of the band to the thighs and legs during calibration. The algorithm could also use other 2D sensors in another embodiment to construct 3D rotational sensing, such as in other embodiments using MEMs gyros (e.g., (e.g., $V_x=\alpha$, $V_y=\beta$, $V_z=\gamma$ for $dV/dT=\omega$ gyro rates of these angular velocities of angular motion vs. the vector motion of B and G as shown in FIG. 19). The summed pressure sensors, $P_R$, equals the calibration for the Hg loop sensing during the calibration, making the metrics in psi units to translate to force, with the area of the sensor puck and active FSR surface area being included.

Figure 20:
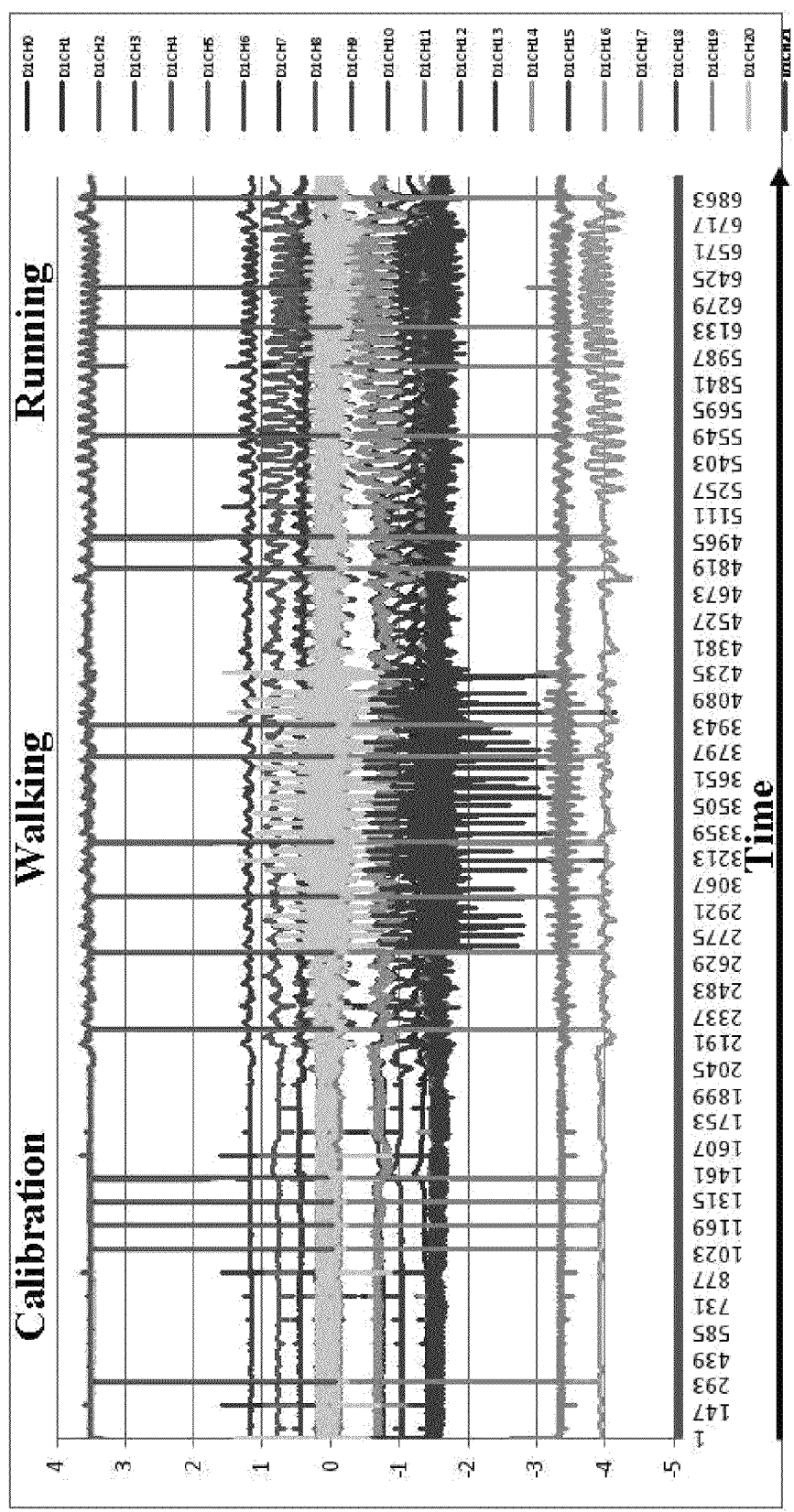
FIG. 20 shows digital data of 5-MSMs on calf band similar to FIG. 12 for Hg loops.
Figure 21:
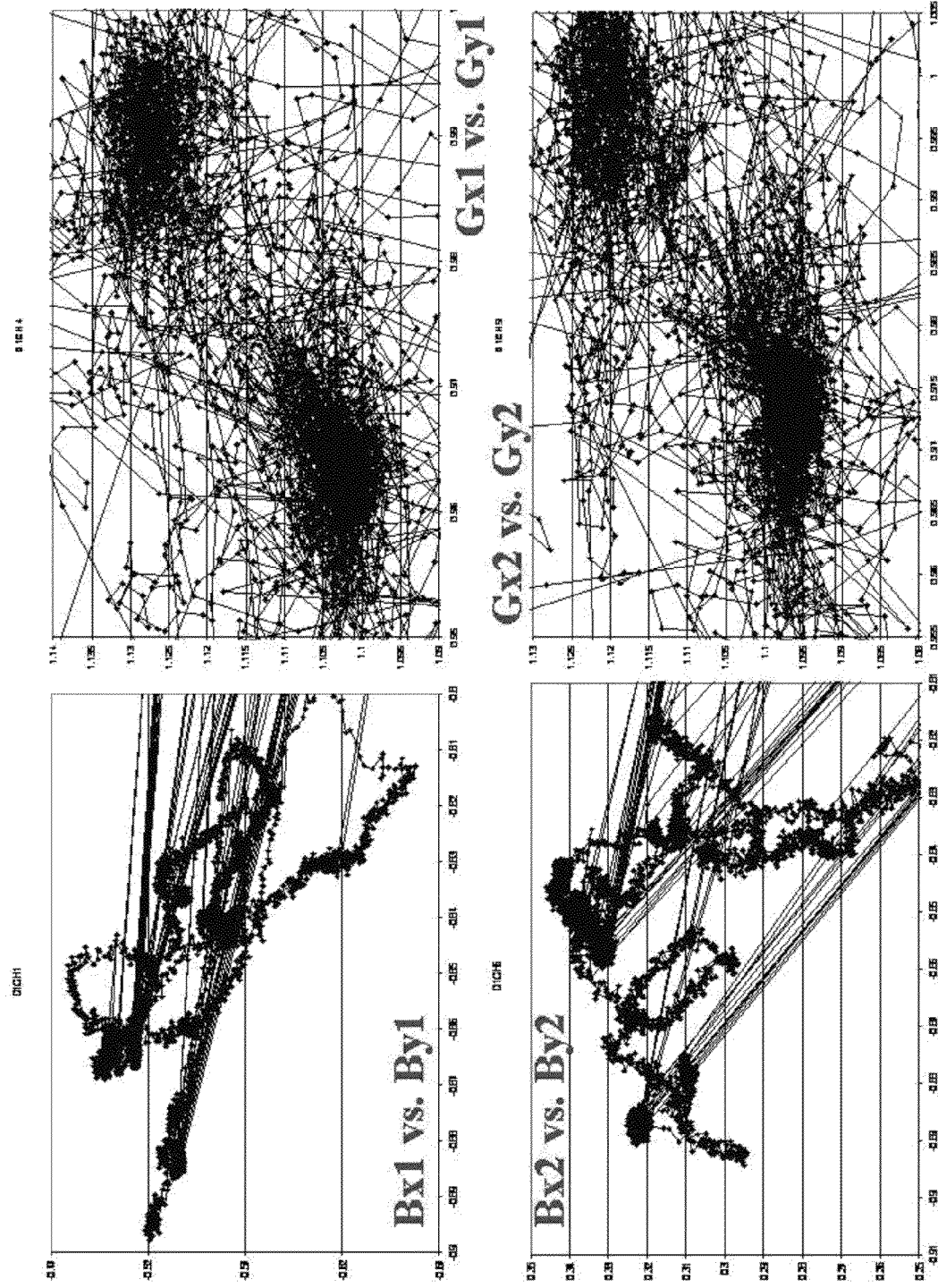
FIG. 21 shows MSM#1, #2 data scatter plots: L (B1-x/y, B2-x/y), R (G1-x/y, G2-x/y).
Figure 22:
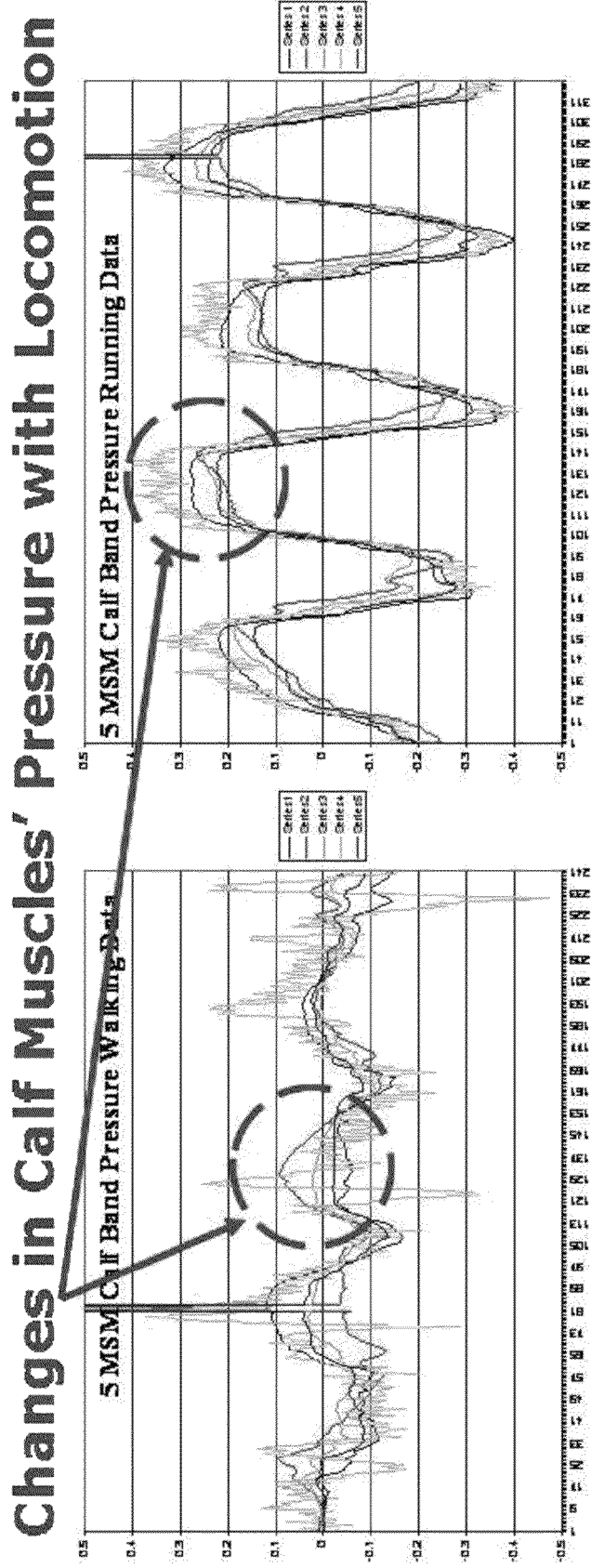
FIG. 22 shows FIG. 20 detailed 5 muscles' pressure activity variation vs. θ placement.

FIG. 20 shows data similar to FIGS. 5, 10, 12, with a calibration, walking, and running activity, only here the individual MEMS on the 5-MSM boards have many more channels being digitized with a 32 Channel ADC. FIG. 21 shows the magnetic and gravitational sensor scatter plots of data (e.g., for Bx vs. By and Gx vs. Gy, for the MSM #1 and #2 sensors). The data shows clear cyclic location metrics in time as the points sequence with the walking and running motion, yet trace out the same patterns, showing the limb motion in the relative orientation to be quite similar, but different for the two locations of the MSM boards on the band (roughly 2" apart). The gravitational data is similar, with the cyclic patterns being overlaid for the same time period data set, but with a very clear separation between the two gravitational orientations of the fields as being the same, for the case of a=g and a=0 (as shown in FIG. 3 for the modeled one leg stance), forming the two large elliptical regions of tight, circular looped data, for the stance (UR) and swing (LL) gait cycle motion phases. FIG. 22 shows a short time segment of the five individual sensor data plotted in time for just the calf-sensing band, during a walking and running activity, as noted in FIG. 20. There is a clear distinction between the different muscle regions with time that are superimposed with band MSM number, with the more typical "flat-topping" cycle of the running activity. The spikes on some of the data are the set/rest pulses used to remove the hysterias of the magnetic sensor, and can be digitally removed as well as can the noise on one of the channels.

Figure 23A:
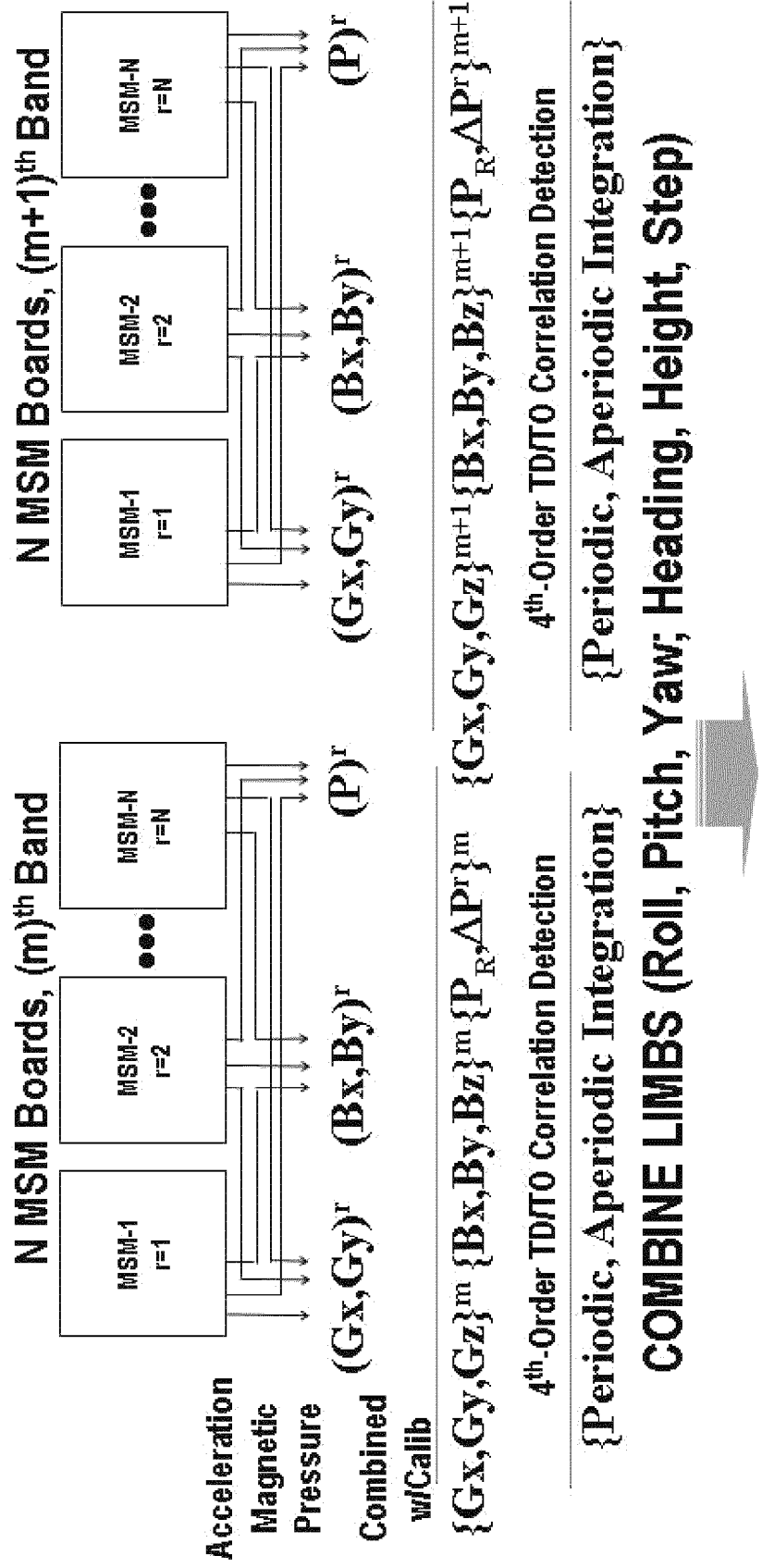
FIG. 23A shows 2-band digital processing for combined limb, 3D locomotion action.

FIG. 23A shows the computation and 3D vector data collected from a pair of bands ($m^{th}$ and $(m+1)^{th}$, for the $r^{th}$ board on each band), and a fourth order correlation of the leg motions are used to locate the aperiodic and periodic behavior in spatiotemporal dynamics as time locations shown in FIG. 7. Here, the integration of the periodic and aperiodic data is used to compute the Lagrangian energy metrics and action, as the limbs are moved during gait cycles with fourth-order detection of TD and TO points limiting the time periods of the integration. A linear approximation is used between the leg modeled parameters space ($\alpha_0$, $l_{LEG}$) of FIG. 7, and the mapping to q coordinates in the 3-axis angular motion band data space (e.g., B/B and G/G).

FIG. 23A shows two different bands (e.g., left leg and right leg at calf). Within each of the bands, the respective modules MSM provide acceleration (pressure), magnetic, and gravitational sensor data. These are shown as gravitational data Gx, Gy for the r-th module, magnetic field data Bx, Bx for the r-th module and pressure data for the r-th module. Thus, each module provides five measurements. This data is combined with the calibration data to provide a gravitational measurement in three axes (Gx, Gy, Gz), a magnetic measurement in three axes (Bx, By, Bz) and a pressure measurement including an average and differences about that average ($P_R$, $\Delta P^r$) for each band. These two sets of data are then correlated in time to determine the TO and TD transitions, which define the integration points. From these transition points in the time data, Balance and Track, and gait measurements can be determined, along with derived biomechanical and feedback parameters.

These same sensors are capable of measuring the changes of mass about this CM, which characterizes the aperiodic element of Balance, during the short, aperiodic times between the periodic gait sequences of steps and normal rotational cycles of the pumping arms, swinging shoulders, hips, and torso spine and neck, with bobbing head, shown in FIG. 3. Here, these angular rates can also be measured with MEMs gyros, where one might expect that during the swing phase in a similar manner to $\alpha_0$ shown in FIG. 7, there is a change of the angle from 110° to 130° to 60° to 70°, or a total of 100° in the 38% of the step cycle (0.5 sec), or at an angular rate of greater than 500°/sec. As mentioned earlier, differences in band sensors can be used to measure angular rates of rotation, and by integration of the products in the fourth-order excess autocorrelation function, one can isolate the swing and step phases. Now, the Lagrangian contributions of $KE=\frac{1}{2} Mv^2$ and PE=Mgh for the stance phase, and $KE=\frac{1}{2} I \omega^2$ and PE=Mgh for the swing legs will alternate during the gait cycle to construct the Track and Balance metrics. A Lagrangian representation of the mammal mass motion, allows for the separation of this CM-Track and ACM-Balance activities, with the proper placement and location monitoring of appendages having local pressure measurements being made to monitor muscle activity, and changes in limb location and gravitational acceleration to monitor footfall and appendage locations.

Figure 23B:
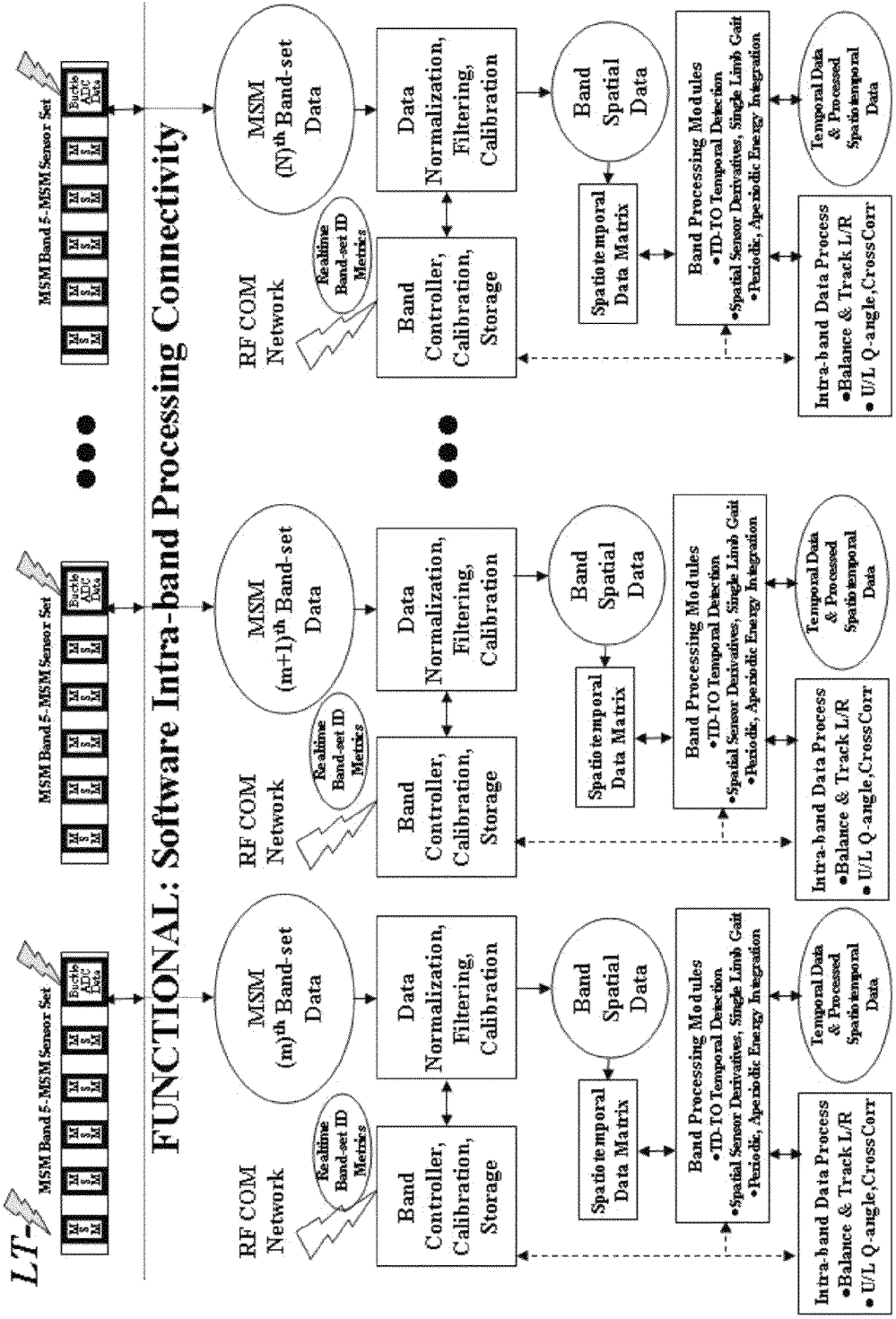
FIG. 23B shows N, FIG. 18 MSM bands in Physical RF-connectivity with a Laptop (LT) using intra-band MSM-data processing, and inter-band data processing algorithms.

FIG. 23B shows the physical-components of a set of N-bands above the dashed horizontal line with five-MSM modules and a buckle for battery power, RF connectivity and electronic control and data processing, and the functional-components of the data processing software (SW) operating in the physically labeled 'Buckle ADC Data' processor of each band below the dashed horizontal line. This physical/ functional data processing and RF connectivity has three modes of operation: 1) as a inter-band sets between two L/R limbs, 2) as a single mammal set with calf and thigh L/R inter-band RF connectivity, and 3) as a single or multiple mammal set with RF connectivity that includes a laptop ("LT") RF connectivity shown (with an additional RF-bolt in the physical network connectivity above the dashed line), for displaying real-time data metrics of Balance and Track from each ID'd mammal.

These three physical connectivity operational modes are functionally operating in a number of application configurations, such as in a minimal mode of only a calf-set of N=2, without a laptop for metric-data collection, but still saving the results from a single mammal locally that includes gait data from L/R cycles, or with the addition of two more bands, for N=4, again without a laptop, but as a thigh/calf L/R set that allows for Q computation and a better estimate of the aperiodic motion by including the thigh gyration data in addition to the calf thrust data. With a laptop connectivity added into the physical RF network, the individual band computations can be connected from the inter-band computations between 2 or 4 bands that included the mammal ID (shown as a data metric element on the right side of the RF-bolt above each Band Controller box).

The four functional boxes for intra-band data processing begin with a continuous digital data collection process using the analog-to-digital converter (ADC), shown in the band buckle of FIGS. 17 and 18, where the calibrated data has been stored in the included band controller and processing unit and is used to:

1) Calibrate the data, filter out artifacts, and to normalize the data with statistical or other nonlinear mapping techniques using a PDF cumulative function, where then this data is acquired from each band module organized as a band spatial data set for each sample in the time sequence of synchronous analysis, and then the set of
2) Multiple time samples becomes a time sequence of the spatial data, and is stored in the functional processing as a data matrix of spatiotemporal data, and this data set is operated on with the remaining function algorithm sets:
3) The band-processing module for computing
   a. the detection of TD and TO in order to locate the periodic and aperiodic points in the gait cycle data for a single limb,
   b. the spatial derivatives of the sensor data as d/dR formats,
   c. the single gait metrics for a time sequence of the data over both periodic and aperiodic data, and
   d. the energy computations of the PE and KE contributions to the Lagrangian metric using the EL EOM;
4) The intra-band data processing, for
   a. combining L/R limb gait and Balance & Track metrics, and
   b. calf/thigh (U/L) Q-angle metrics, and
   c. cross-correlation time and spatial data analysis (labeled "CrossCorr"), using the temporal data sets and process spatiotemporal data sets output of 3) above.

These multiple computations become a metric packet with a mammal ID and time stamp for inter-mammal synchronization, shown as realtime band-set ID metrics of the RF COM network, to be used in 1) the Laptop database function, 2) the on-band feedback, and 3) the multiple mammal interaction display in real-time.

The systems and methods described herein infer the more detailed modeling aspects of locomotion from inferred energy action within the measured muscles of just the sensor bands, which can be related back to muscle action in the toes and knee. Rotational actions will independently be limb measurements of the band, with the magnetic limb 3D location sensing and gravitational 3D gravity force sensing. Because the chosen muscle sensor is placed around the cross-sectional bandings of the thigh and calf, it is important to determine the number of muscle sensors and band sizes required for a large portion of the population. Here, the maximum circumference cross-section measurements would be made at the midpoint for a band stress measurement product, which uses a variable length for the thigh or calf, similar to the Mercury (Hg) loops used in the previous measurements (Solinsky U.S. Pat. No. 7,610,166).

The band lengths fall roughly into three percentile ranges (10% to 90%) for children, young adults, and mature adults. They are for Calf {small 28-35 cm, med 33-40 cm, and large 38-45 cm} and for Thigh {small 38-56 cm, med 42-60 cm, and large 46-64 cm} (McDowell 2008). This band structure in these three sizes, for use in pairs of thigh or calves or both, as a Track and Balance measurement system has the following features described in this application that include the following:

1. Using individual pressure sensors, constrained on the skin by attachment, being placed near major muscle groups or muscle regions for measuring pressure changes of synchronous timing of muscle action sequences, as related to locomotion metrics of Track and Balance.

2. Using muscle expansion and contraction of radial limb pressure (P) sensor measurements placed in fixed proximity to the body skin on lower body limb midpoints (e.g., thighs, leg-calves, and even ankles), to represent vector elements of foot thrust forces using a functional mapping ($\Im$), as $A=\Im\{P, A_p\}$, in alignment with the body limb bones (e.g., femur, tibia) being exerted through limb joints (hip-pelvis, knee-patella, ankle-heel). Here, P=radial force per unit sensor area, $A_p$, as a pressure $P_r$, for each $r^{th}$ sensor, written in a column vector form.

3. Using in (2) a force amplifier in the form of a hemispherical button or "puck" on a flat pressure sensor to increase measurement sensitivity of a simple, resistive-sensitive force sensor.

4. Using instead of (3) a bladder air bag with pressure monitoring for increasing force sensor measurement sensitivity.

5. Using (1) with additional Earth's fields of magnetic and gravitation 3-axis data for member relative location (placed on an ellipse of foci centered on bone cross-section locations) during muscle pressure measurements, or in another embodiment, gyro inertial motion sensing can be used to monitor angular motion.

6. Using (1,5) multiple single-axis and two, orthogonal-axis sensors in a circumference around a body member combined as a pseudo-computation for 3-axis magnetic, 3-axis gravitation, and 3-axis circumference radial-pressure force measurements (based on mean pressure as a pseudo Hg loop, and as a difference to this mean for each MSM sensor).

7. Using (6) with sensors placed along a flat band in a fixed, linear distance to compute a relative angular location on an elliptical circumference, defined by limb cross-sectional components of muscle and bone tissue, when attached to a limb member for position computation (5).

8. Locating a collection of pressure sensors on multiple limbs in a relative three-dimensional (3D) motion manner using magnetic vector sensor 3D measurements of the Earth's magnetic field (B), in proximity to the pressure sensors, to determine relative local limb Euler angular positions {in coplanar angle $\Delta\alpha$ and rotational plane angle $\Delta\beta$, as coplanar between the tibia and the fibula bones}, which are synchronous with pressure sensor measurements, and a fixed base location by a band attachment.

9. Locating a collection of pressure sensors on multiple limbs in a relative three-dimensional (3D) force vector (G) interaction from the Earth's gravitational acceleration (g) of the known body total mass (M) being supported by the limbs in contact with the ground at the time of measurement, where G=Mg using 3D accelerometer sensor measurements of the Earth's gravitational field, in proximity to the pressure sensors, to determine relative local limb gravitational forces synchronous with thrust pressure sensor measurements, which are synchronous with pressure sensor measurements, and a fixed base location by a band attachment.

10. Perform a calibration data collection of the instrumented limbs placed on the body, with mass M measured weight, at the calf (and at the thigh if used) using five forms, by a) having the body form in a standing (and is upright for two legged) position while facing magnetic North, and performing a body jump by lifting all feet off of the ground and returning; b) then rotating 90 degrees clockwise (CW, East), repeating the jump, c) then rotating 90 degrees CW (South), repeating jump, d) then rotating 90 degrees CW (East), repeating jump, e) then rotating 90 degrees CW back to the starting position (North), and repeating jump. In human upright locomotion applications using thigh sensors, an additional calibration of a North facing position while sitting in a chair with the legs positioned relative to the thighs in a relaxed angular format (roughly a 90 degree thigh-calf position), and in a stressed angular format (roughly a 0 degree leg position as a straight non-angular placement of the feet equal to the sitting thigh positions), together which will determine the knee angle for thigh-calf sensor calibration. Four-limbed mammal locomotion, calf calibration, can be performed using known step elevations, placed at compass points.

11. Combining (8,9) using the calibration data (10) and the relative physical position of the actual sensors to the band, when aligned to the limb structures as external 'flatness' manifestations of the internal limb bones, as a conic section of relatively referenced circumference angles (2,3) to this alignment, when the band is placed on the limb to solve for the base 3D standing positions of the sensors as a superposition of the individual sensors.

12. Combining (2,8,9) in a sum and difference manner over sequential samples in time (t) with calibration coefficients (10) to determine vector fields (A (as derived from pressure sets P), B, G), and transverse angular positions ($\alpha$) of the limbs relative to the ground normal (and angular rates of motion, $d\alpha/dt$), and rotational angular positions ($\beta$) relative to the forward facing normal (and angular rates of rotation, $d\beta/dt$). Other rates used in the computation are the relative sensor measurement changes in time and position under an ergodic assumption, around the band circumference (angle as a linear distance R) as $dB/dt$, $dG/dt$, $dP/dt$, $d\omega/dt$ and $dB/dR$, $dG/dR$, $dP/dR$, $d\omega/dR$ which can be integrated in space or time to produce data that has biases removed, after a derivative is estimated using just the difference of the sensor band position values.

13. Combining (2,8,9) calibrated pressure sensor measurements from paired limb sets (two calves, two thighs, or both) in a synchronous manner to represent Lagrangian dynamic motion elements of rotations about the body center of mass (ACM) rotational motion.

14. Combining (2,8,9) pressure sensor measurements from paired limb sets (two calves, two thighs, or both) in a synchronous manner to represent Lagrangian dynamic motion elements of translations of the body center of mass (CM) transverse motion.

15. Using nonlinear data mapping techniques with (14), such as a cumulative density function (CDF) used for point mapping, derived from a Gram-Charlier probability density function (PDF) using estimates of mean ($\mu$), variance ($\sigma^2$), skewness (S), and excess kurtosis (K), or from other estimated CDF forms, such as using an integration of a histogram (being a simple PDF estimate) to map data into a defined min/max value limit for measurement computations.

16. Using higher-ordered statistical correlation statistics for recognition of aperiodic data cycles boundaries in sensor measurements over time, as a beginning and an ending in locomotion data analysis.

17. Using integration of periodic motion between aperiodic gaps of touchdown (TD) to TO cycles for Track computation in locomotion data analysis, per the modeling of FIG. 7, and estimation of such model parameters of vertical height peak values or PE apex in a gait cycle.

18. Using integration of aperiodic motion between periodic gaps of TO to TD cycles for Balance computation in locomotion data analysis, per the modeling of FIG. 7.

19. Using a combination of (17,18) in multiple limb motion dynamics for Track and Balance computation metrics, as a L/R or calf/thigh (or both) cross-limb, higher-ordered correlation dynamic.

20. Using further cross-limb HOS correlation of band data in determining new metrics of locomotion in a Track and Balance simplification.

21. Defining within a gait cycle time period of foot placement on the ground, the dynamics of Newtonian Mechanics that are represented in second-order correlation statistics (e.g., Covariance), when integrated over a sub-period of the gait cycle time.

22. Defining within a gait cycle time period of foot placement on the ground, the dynamics of Newtonian Mechanics that are represented in higher-order statistics of specific fourth-order correlation statistics in excess of the second-order correlation statistic (e.g., Coelongation), when integrated over a sub-period of the gait cycle time.

23. Using a Lagrangian representation in generalized coordinates of motion for computing locomotion dynamics of Track and Balance metrics.

24. Combining (11,12) in a representation of forward dynamic body motion using a Lagrangian Equation formulation of Newtonian mechanics as Track metrics, with integration times over the relative periodic paired limb determined time periods (19,20).

25. Combining (11,12) in a representation of gyration dynamic body motion using a Lagrangian Equation formulation of Newtonian mechanics as Balance metrics, with integration times over the relative aperiodic paired limb determined time periods (20,21).

26. Combining (12,13) in a separable manner using (13,14) definitions for computing Track and Balance metrics simultaneous across all multiple limb pressure sensor measurements.

27. Combining (12,13) in a separable manner for periodic, dynamic motion in time that approximates a sinusoidal function.

28. Combining (12,13) in a separable manner for aperiodic, dynamic motion in time that does not approximate a sinusoidal function.

29. Using an aperiodic Lagrangian for generalized motion of pitch, roll, and yaw defined at many possible positions, including for example the base, small of the back and pelvis in about center of mass motion (ACM).

30. Using a periodic Lagrangian for generalized motion of heading, step, and height defined at many possible positions, including for example the base, small of the back in a center of mass motion (CM).

31. Combining the Lagrangian of Track as representing the forward CM linear momentum dynamics and the Lagrangian of Balance as representing the rotational and twisting angular momentum.

32. Using the defined periodic and aperiodic cycle integrations for solving for the two ACM and CM forms of the Lagrangian involving multiple limbs under gait cycle changes in sensor data analysis, defined by detected time period locations.

33. Using the assumption of conservation of angular momentum for defining balanced ACM motion, and violation of this assumption for defining errors in balance ACM locomotion.

34. Using a parametric amplifier model of the changes in appendage inertia contributions for representing the combined appendage angular momentum driving the Balance contributions.

35. Use a double inverted, compliant pendulum model for representing appendage inertial momentum driving the appendages attached to the pelvis for computation of Balance and Track metrics.

36. Using a representation of the appendage length, as changes in the mid-limb 3D location, and mass changes as a component of dynamic angular momentum from the double inverted, compliant pendulum motion in angular momentum combinations across multiple limbs for computation of Balance and Track metrics.

37. Mapping pressure force measurements of leg and calf sensing bands into pseudo-muscle decomposition using independent component analysis (ICA) to improve the components of energy isolation of work, in an optimized action over gait cycles.

38. Use neural-network (NN) mappings of sensor measurement coordinates into a generalized Lagrangian coordinate system through a process of gait cycle training.

39. Using historic database collections of Track and Balance to determine individual anomalies and/or trends leading to precursors of disease or potential injury conditions.

40. Using realtime measurements of Track and Balance using historic normalization from (38) to provide feedback to the individual as methods of alertment or continuous changes (using for example audible tone changes), which guide the individuals physical actions as an improvement in gait parameters and Track and Balance metrics.

41. Using metrics of Track and Balance that compute soul-slip, for applications in determining the value of a type of shoe for s specific need of human locomotion conditions.

42. Using metrics of Track and Balance to provide local band feedback stimulation signals to the leg near the band, such as might be from a small electrical "tickle".

43. Integrating the measurements of Track and Balance of a horse and rider as a system that optimizes energy efficiency of both the horse and the rider, using a set of calf bands on all six-limbs of the system, as described next.

Figure 24:
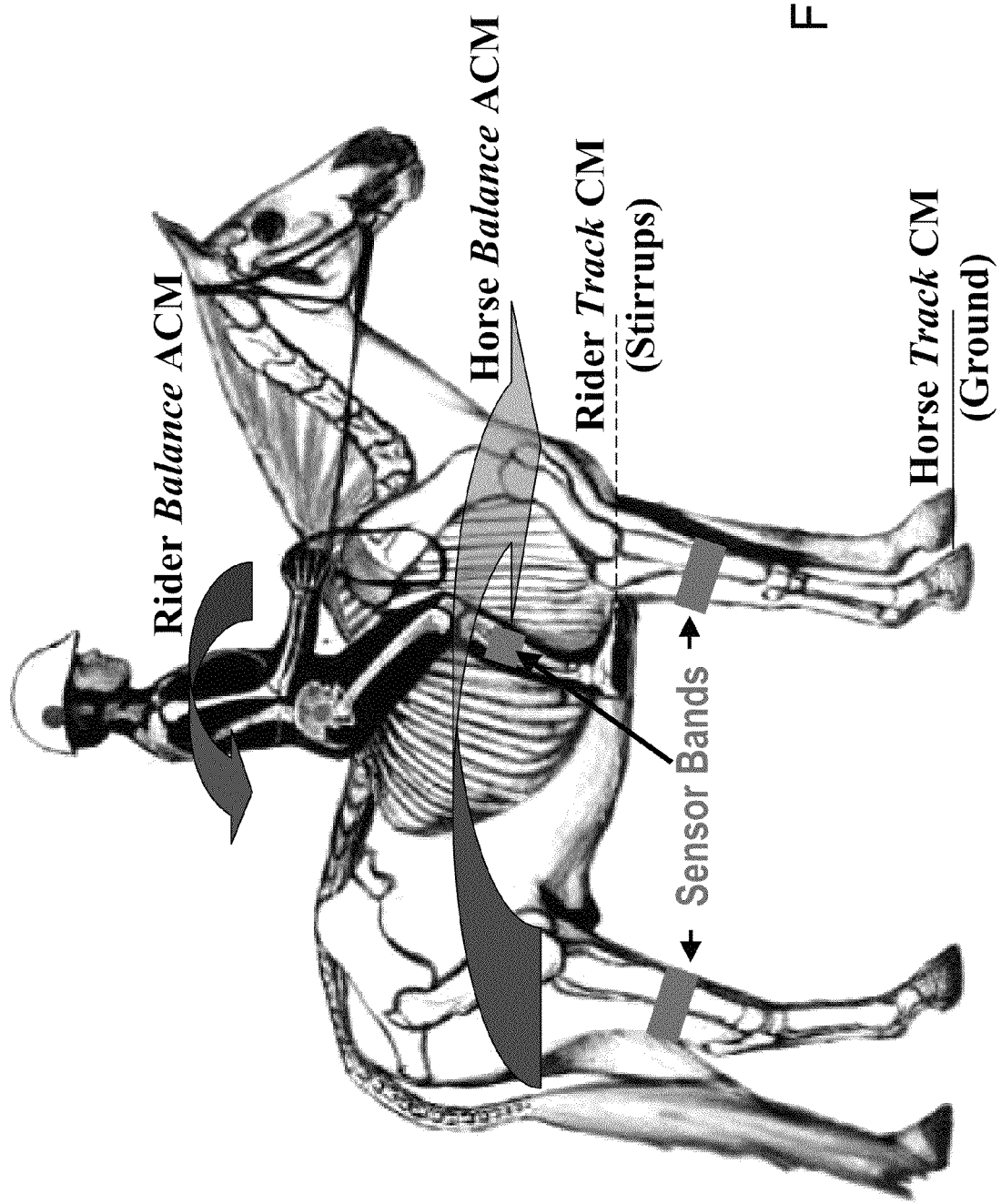
FIG. 24 shows multiple limb, 3-band placement per side on horse/rider calf muscles.

44. A more complex example application of the system (43) is shown in FIG. 24 for a horse and rider, where the Balance and Track is being computed between the rider's bands (shown on the right side calf only), and between the horse's calf bands (also shown on the right side calves only). FIG. 24 shows Track and Balance for the rider riding on the stirrups (so the rider's ground is the stirrup) and the horse is running on the running surface (so the horse's ground is the running surface). The sensor bands are only provided on the horse's calves because the horse's thigh is inside the body. Although not shown in FIG. 24, sensor bands could also be provided around the rider's thighs. The rider is trying to be in balance and the horse is trying to be in balance. The sensor bands can be used to determine, for example, whether a jockey/horse combination provides optimized locomotion for moving down a racetrack.

Here, the data can also:
a. Use the RF connectivity to compare the Balance and Track of the two systems, where the Track of the rider is affecting the Balance (shown as a rotation angular arrow) of the horse through the stirrups, and visa a versa, where the horse's Track in the two system dynamics is also affected by the rider's CM motion as a change to the horse's CM location, which can change its Balance, and such motion causing a change in the stirrups positions that affect the Track of the rider b. Allow the two to become as a single system in Balance on a Track of the total horse-rider mass unit, the actions that minimize the energy needed to achieve the intended speed in a professional horse racing situation, going over obstacles in a steeplechase situation, or for other recreational rider/horse combinations c. Perform an optimized use of energy in the combined motion that can provide feedback to the rider for creating "Olympian" performance, and for the trainer to better match the horse to the rider on the day of the race as a team for optimized energy expenditure during a race, as well as for many other horse/rider recreational sports.

The above-described systems and methods use pressure sensors attached circumferentially to lower body muscles, particularly to encircle the thigh and calf regions, to determine muscle functional actions related to locomotion. In alternative implementations, upper body muscle bands may also be used.

The disclosed example systems and methods obtain gait analysis information without using a foot sensor, but instead using multiple bands attached to the calves of each mammal's leg near the midpoint, and in the case of requiring biomechanical gait parameters related to knee angle and a double inverted pendulum modeling, an additional band is attached to the upright locomotion's upper limb at the thigh midpoint, where pressure sensors are used to measure locomotion muscle actions.

Gait analysis parameters can be derived from two paired-limb sensor bands, which do online real-time processing to combine both sensor band data sets in a complete step of stance and swing phases and stride gait analysis from two or four legged mammal applications.

Relative limb positions are located in 3D relative to the ground, by attaching flat bands around limbs, which contain multiple measurements from 2D orthogonal vector sensors (e.g., magnetic, gravitation, acceleration) spaced along the band, which are combined in a synchronized manner to integrate the data into a 3D vector solution at the "virtual" radial center of the limb in the earth's force fields of magnetic and gravitational forces, using initial compass point and jumped gravity data collection for calibration.

Force sensors of equal area are placed to electronically measure muscle pressure changes in the circumference along the band position location of the sensors on specific limb muscle locations as changing spatial locations from limb motion, in order to infer from spatio-temporal integrations of collected data, an energetic action to infer the muscle functionality dynamics related to gait parametric analysis.

Three sensor types are combined on a single multi-module board, or in a distributed format, to sample the 3D space of the band-encompassed limb volume representing temporal muscles actions with dynamic, spatio-temporal 3D limb location changes relative to the ground gravitational and foot thrust forces, and energy expenditures.

Aperiodic dynamics in upper and lower body motion data are detected, with mathematical techniques that include but are not limited to higher-ordered statistics (HOS; including but not being limited to that of fourth-ordered correlation and its zero-lagged value of excess kurtosis), from other periodic dynamics in upper and lower body motion data, with mathematical techniques that include but are not limited to lower-ordered statistics (such as Gaussian; including but not limited to equal or below second-order correlation and its zero-lagged value of variance), from other aperiodic dynamics data in upper and lower body motion data, as a process to define regions for the integration of dynamic limb motion from both linear and angular dynamics resulting from neural-muscular energy action processes.

A Euler-Lagrangian dynamic Equations of Motion (EL EOM) formulation in generalized coordinates ($q_1$, $q_2$, $q_3$, $q_4$) is used for the real body coordinates of heading, height, and step for the CM body mass, linear inertial momentum (Mv) as weight (Mg), and the ACM body mass, of angular momentum as inertia weighted angular velocity (I $\omega$) whereby the periodic motion of CM locomotion is in made in generalized coordinates relative to the 3D gravitational acceleration vector angle (being measured on the limb-band radial volumetric-center encompassment) as a relative height direction $q_1/q_1 = G/|G|$, and relative height-length value ($|q_1| = h$), determined from an arbitrary reference of beginning stationary calibration (e.g., CM located at the small of the back). The angular velocity, aperiodic motion of the ACM locomotion is made in generalized coordinates relative to the 3D Earth's magnetic force field vector angle (in degrees being measured on the limb-band radial volumetric-center encompassment) as $q_2 = \omega (= d/dt[B/|B|])$. The step alignment on the ground thrusts aligned between step locations in a gait cycle of the periodic footfalls of Track as 3D vector length $q_3/q_3 = s/s$) between steps having length ($s = |s|$), with angular vector components approximated from a heading defined by the compass heading derived from B, from a pitch up-from-the-ground, defined by the relative height differences between two steps (e.g., $\Delta h = s_2 - s_1$), and from a roll up-from-the ground on the left side to ground as a change in leg lengths to the ground between stance and swing phases (e.g., $\Delta l = l_2 - l_1$). The changes in the point mass density for the inertia representation, I, where here the distance of the mass locations along the angular rotation axis r are varying with the leg length during the swing-phase (ignoring arm and upper body actions); here $q_4 = <r>$, is mostly a length value from a table representation of approximate body weights of the $l^{th}$ limbs (e.g., $M_l$), which is at the approximation length of $q_4$ of the knee joint location (on the lower body from the pelvis when standing), but in a more complex embodiment, this could be computed with further limb mass approximations and with analysis at a higher fidelity within the periodic and aperiodic sections of the gait cycle.

Data is collected from sensor bands in a synchronized manner using RF connectivity, such as with a two limb sensor-set, or two mammals, each with a sensor set, that supports spatiotemporal correlation in second-ordered, and higher-ordered statistics (e.g., fourth-order Coelongation) in order to determine integration of periodic and aperiodic locomotion metrics of Track and Balance useful in monitoring diagnostics, therapy, and treatment for disorder, injuries, and recovery of the brain, spine, stroke and lower body muscles, and for elderly brain disorders from dementia, and Alzheimer and Parkinson diseases.

The example systems and methods integrate within and across numerous gait cycles, in a generalized Lagrangian representation for band measurements on dynamic limb motion, using a generalized coordinate system differentiating between components of periodic CM and aperiodic ACM dynamics, which provides metrics Track and Balance and gait parameter information being reported from numerous RF connected band components to estimate group interaction and individual locomotion event identification that is a precursor to potential injury of less optimized performance.

The example systems and methods can self calibrate a locomotion measurement system using sensor bands being notified of being in a calibration mode, either through external RF commands, or for detecting specific data patterns among multiple sensors, where all of the data is collected from simple body actions such as stepping, jumping, twisting etc., while in a position that faces the four compass points, and includes an upright, and sometimes also a sitting position in a chair for including thigh band calibration.

Multiple sensing bands are used on the body limbs to determine features of body locomotion when constrained with clothing, shoes, coats, etc., that indicates an improper fit or sizing when performing typical locomotion under everyday tasks and recreation.

Multiple measurement points on outer body limbs are used to determine discrete muscle action regions relative to the limb motions under locomotion tasks, with a metric of optimization of energy expended under Track and Balance metrics, but which is not limited to the lower body, but can include neck, arms, waist and other torso regions, but without the need for foot ("shoe") or hand ("glove") instrumentation. Recreational and sports training in group activities, where skills of non-injurious interaction is valued, can be assessed and Track and Balance metrics collected across the teams can be reviewed to show trends of individuals as they approach contact under varying stress and logistics of the game.

The example systems and methods can use the assumption that ACM angular momentum is conserved and assumes the gravitational force has no net effect on ACM dynamics, when forming derived metrics of Track and Balance from band measured data.

Cross-limb correlation analysis of band measured data for Track and Balance metrics, such as L-thigh to L-calf, L-thigh to R-thigh, R-thigh to R-calf, etc., can be used when forming derived metrics of Track and Balance from band measured data.

Combined mammal locomotion metrics of Track and Balance can be used in a system of metrics for more optimized energy expenditure such as in horse racing.

The described systems, methods, and techniques may be implemented in digital electronic circuitry, computer hardware, firmware, software, or in combinations of these elements. Apparatus embodying these techniques may include appropriate input and output devices, a computer processor, and a computer program product tangibly embodied in a non-transitory machine-readable storage device for execution by a programmable processor. A process embodying these techniques may be performed by a programmable processor executing a program of instructions to perform desired functions by operating on input data and generating appropriate output. The techniques may be implemented in one or more computer programs that are executable on a programmable system including at least one programmable processor coupled to receive data and instructions from, and to transmit data and instructions to, a data storage system, at least one input device, and at least one output device. Each computer program may be implemented in a high-level procedural or object-oriented programming language, or in assembly or machine language if desired; and in any case, the language may be a compiled or interpreted language. Suitable processors include, by way of example, both general and special purpose microprocessors. Generally, a processor will receive instructions and data from a read-only memory and/or a random access memory. Non-transitory storage devices suitable for tangibly embodying computer program instructions and data include all forms of non-volatile memory, including by way of example semiconductor memory devices, such as Erasable Programmable Read-Only Memory (EPROM), Electrically Erasable Programmable Read-Only Memory (EEPROM), and flash memory devices; magnetic disks such as internal hard disks and removable disks; magneto-optical disks; and Compact Disc Read-Only Memory (CD-ROM). Any of the foregoing may be supplemented by, or incorporated in, specially-designed ASICs (application-specific integrated circuits).

The following documents generally relate to technology discussed in this patent application:

U.S. Pat. No. 7,648,472
U.S. Pat. No. 7,647,196
U.S. Pat. No. 7,640,804
U.S. Pat. No. 7,632,239
U.S. Pat. No. 7,627,451
U.S. Pat. No. 7,620,520
U.S. Pat. No. 7,611,520
U.S. Pat. No. 7,610,166
U.S. Pat. No. 7,552,538
US 2008/0146968
US 2007/0229552
US 2007/0021689
US 2006/0195050
US 2006/0155386
US 2006/0000420
U.S. Pat. No. 6,836,744
U.S. Pat. No. 6,831,603
U.S. Pat. No. 6,807,826
U.S. Pat. No. 6,784,826
US 2004/0154192
U.S. Pat. No. 6,699,207
U.S. Pat. No. 6,663,519
U.S. Pat. No. 6,360,597
U.S. Pat. No. 6,292,106
U.S. Pat. No. 5,955,667
U.S. Pat. No. 5,952,585
U.S. Pat. No. 5,899,963
U.S. Pat. No. 5,724,265
U.S. Pat. No. 5,623,944
U.S. Pat. No. 5,613,690
U.S. Pat. No. 5,511,561
U.S. Pat. No. 5,474,087
U.S. Pat. No. 5,311,880
U.S. Pat. No. 5,299,454
U.S. Pat. No. 5,186,062
U.S. Pat. No. 4,969,471
U.S. Pat. No. 4,834,057
U.S. Pat. No. 4,813,436
U.S. Pat. No. 4,745,930
U.S. Pat. No. 4,635,932
U.S. Pat. No. 4,631,676
U.S. Pat. No. 4,600,016
U.S. Pat. No. 4,416,293

H Gray, *Anatomy of the Human Body*, www.thedora.com/anatomy; Human Body>IV.Myology>/The_Muscles_and Fasciae_of_the_Iliac_region.html, _Thigh.html, _Leg.html, _Ankle.html, _Foot.html (1918). (Ibid.); Human Body>XII.Surface Anatomy and Surface Markings>surface_anatomy_of_the_lower_extremity.html (1918).

D E Hokanson, D S Sumner, D E Stirandness, "An Electrically Calibrated Plethysmograph for Direct Measurement of Limb Blood Flow," IEEE Trans Bio Eng BME22 (1) 25-29 (January 1975).

W J Freeman, *Mass Action in the Nervous System*, Academic Press, NY, N.Y., (1975).

N Yamazaki, H Ishida, T Kimura, M Okada, "Biomechanical analysis of primate bipedal walking by computer simulation," J of Human Evolution 8 (3) 337-349 (March 1979).

J G Reid, P A Costigan, "Trunk muscle balance and muscular force," Spine 12 (8) 783-786 (October 1987).

G M Shepherd, "Neurobiology," 2nd Ed, Oxford Pres, pg 286, 412 (1988). See also H Markl, "The perception of gravity and of angular acceleration in invertebrates," Handbook of Sensory Physiology 6 *Vestibular Systems*, Springer-Verlag pg 17-74 (1974).

A. Katbab, "Analysis of human torso motion with muscle actuators," Ann. Biomedical Eng., 17 (1) 17-91 (January 1989).

P J Pretorius, N T Malan, H W Huisman, P J Laubscher, F C Eloff, F A J deKlert, S J van der Merwe, "The use of a continuous non-invasive blood pressure recorder to study experimental stressors," IEEE Eng in Med & Bio Soc $11^{th}$ Int Conf, CE2770, pg 0128-0129 (June 1989).

G Nemeth, H Ohlsen, "Moment arms of hip abductor and adductor muscles in vivo computed tomography," Clinical Biomechanics 4 (3) 133-136 (August 1989).

A Urso, R Shankar, B Szabo, "Design of a High Signal to Ratio Electrical Impedance Plethysmograph," Proceed SouthEastcom, Session 11F5, pg 1100-1104 (1990).

N N Byl (also N Niles), P Sinnott, "Variations in balance and body sway in middle-aged adults: Subjects with healthy backs compared with subjects with low-back dysfunction," Spine 16 (3) 325-330 (March 1991).

R J Elble, SS Thomas, C Higgins, J Colliver, "Stride-dependent changes in gait of older people," J of Neurology 238 pg 1-5 (1991).

S I Sagatum, T I Fossen, "Lagrange Formulation of Underwater Vehicles," IEEE Conference (ISSN#0-7803-0233), pg 1029-1034 (August 1991).

G S Berns, M L Hull, H A Patterson, "Strain in the anteromedial bundle of the anterior cruciate ligament under combination loading," J Orthop Res 10 (2) 167-176 (March 1992).

J Perry, *Gait Analysis: normal and pathological function*, pg 114-124, 414-421 (1992).

E Barrey, P Galloux, JP Valette, B Alvinet, R Wolter, "Stride characteristics of over ground versus treadmill locomotion in saddle horses," Acta Anatomica 146 (2-3) 90-94 (1993).

J E Bullock-Saxton, Vladimir Janda, M I Bullock, "Reflex activation of gluteal muscles in walking: An approach to restoration of muscle function for patients with lower back pain," Spine 18 (6) 704-708 (May 1993).

D Intiso, V Santilli, M G Grasso, R Rossi, I Caruso, "Rehabilitation of walking with electromyographic biofeedback in foot-drop after stroke," 25, pg 1189-1192 (1994).

V Dietz, K L Leenders, G Colombo, "Leg muscle activation during gait in Parkinson's disease: influence of body loading," ECG and Clinical Neurophysiology/EMG and Motor Control 105 (5) 400-405 (October 1997).

R E Ballard, D E Watenpaugh, G A Breit, G Murphy, D C Holley, A R Hargens, "Leg intramuscular pressures during locomotion in humans," J Appl Physiol 84 pg 1976-1981 (February 1998).

E M Abdel-Rahman, M S Hefzy, "3D dynamic behavior of the human knee joint under impact loading," Med Engr Physics 20 (4) 276-290 (June 1998).

M Vistintin, H Barbeau, N Korner-Bitensky, N E Mayo, "A new approach to retrain gait in stroke patients through body weight support and treadmill stimulation," Stroke, 29, pg 1122-1128 (June 1998).

K Hase, N Yamazaki, "Computational evolution of human bipedal walking by a neuro-musculo-skeletal model," Artificial Life Robotics, Otila Japan, 3 (3) 133-138 (September 1999).

W J Freeman, "A proposed name for aperiodic brain activity: stochastic chaos," Neural Networks 13, pg 11-13 (2000).

L Y Griffin, J Agel, M J Albohm, E A Arendt, R W Dick, W E Garrett, J G Garrick, T E Hewett, L Huston, M L Ireland, R J Johnson, W B Kibler, S Lephart, J L Lewis, T N Lindenfield, B R Mandelbaum, P Marchak, C C Teitz, E M Wojtys, "Non-contact ACL injuries, risk factors, and prevention strategies," J Am Acad Orthop Surg 8 (3) 141-150 (May/June 2000).

B P Boden, G S Dean, J A Feagin, W E Garrett, "Mechanisms of anterior cruciate ligament injury," Orthopedics 23 (6) 573-578 (June 2000).

M Rebel, H H Paessler, "The effect of knee brace on coordination and neuronal leg muscle control: an early post-operative functional study in anterior cruciate ligament reconstructed patients," Knee, Surg, Sports Traumatol, Arthrose 9, pg 272-291 (2001).

M S Puniello, C A McGibbon, D E Krebs, "Lifting strategy and stability in strength-impaired elders," Spine 26 (7) 731-737 (April 2001).

M L Kaplan, J H Heegaard, "Predictive algorithms for neuromuscular control of human locomotion," J Biomechanics 34 (8) 1077-1083 (August 2001).

L Vogt, K Pfeifer, M Portscher, W Banzer, "Influences of nonspecific low back pain on 3D lumbar spine kinematics locomotion," Spine 26 (17) 1910-1919 (September 2001).

Y S Song, R E Debski, V Musahl, M Thomas, M Gabriel, J Gil, SL-Y Woo, "Stress distribution within the anteromedial and poster lateral bundles of ACL under anterior tibial load," U Pittsburgh MRC, Dec. 14, 2001, (http://www.ruf.rice.edu/~preors/Yuhua-Song.pdf).

S Delorme, M Lamontagne, S Tavoularis, "Kinematic measurements of snowboarder's ankles," World Congress on BioMech, Calgary Canada (2002).

A I Beutler, L W Cooper, D T Kirkendall, W E Garrett, "Electromyographic analysis of single-leg, closed chain exercises: Implications for rehabilitation after anterior cruciate ligament reconstruction," J of Athletic Training 37 (1) 13-18 (March 2002).

A S Ali, K A Rowen, J F Iles, "Vestibular actions on back and lower limb muscles during postural tasks in man," J. Physiol. 546.2, pg 615-624 (Dec. 6, 2002).

F E Zajac, R R Neptune, S A Kautz, "Biomechanics and muscle coordination of human walking: Part I Introduction to concepts, power transfer, dynamics and simulations," Gait & Posture 16 (3) 215-232 (December 2002).

F E Zajac, R R Neptune, S A Kautz, "Biomechanics and muscle coordination of human walking: Part II Lessons from dynamical simulations and clinical implications," Gait & Posture 17 (1) 1-17 (February 2003).

A Seyfarth, H Geyer, H Herr, "Swing-leg retraction: a simple control model for stable running. J of Exp. Biology 206, pg 2547-2555 (Feb. 22, 2003).

R Brill, "Motion analysis finds modern applications," Honolulu Star-Bulletin Business, *Facts of the Matter, http://archives.starbulletin.com/*2003/06/15/business/brill.html, (Jun. 15, 2003); (see also http://www.mofoxtrot.com/wilson/foxtrot.htm and http://bowlingsite.mcf.com/Movement/Hcan.html).

M G Pandy, "Simple and complex models for studying muscle function in walking," Phil. Trans. R. Soc. Lond. B 358, pg 1501-1509 (Aug. 11, 2003).

H Sjostrom, J H Allum, M G Carpenter, A L Adkin, F Honegger, T Ettlin, "Trunk sway measures of postural stability during clinical balance tests in patients with chronic whiplash injury symptoms," Spine 28 (15) 1725-1734 (August 2003).

R. Allendorfer, D E Koditschek, P Holmes "Towards a factored analysis of legged locomotion models," IEEE proceedings Int. Conf Robotics & Automation, Taipei, Taiwan, pg 37-44 (Sep. 14-19, 2003).

S G McLean, A J van den Bogert, "Development and validation of a 3-D model to predict knee joint loading during dynamic movement," Trans. of ASME 125, pg 864-874 (December 2003).

Y P Ivanenko, R E Popple, F Lacquaniti, "Five basic muscle activation patterns account for muscle activity during human locomotion," J Physiol 556.1, pg 267-282 (2004).

S G McLean, X Huang, A Su, A J van den Bogert, "Sagittal plane biomechanics cannot injure the ACL during sidestep cutting," Clinical Biomechanics 19, pg 828-838 (Jun. 6, 2004).

A Lamontagne, J Fung, "Implications for speed-intensive gait training after stroke," Stroke 35 pg 3543-2548 (November 2004).

P Terrier, V Turner, Y Schultz, "GPS analysis of human locomotion; further evidence for long-range correlations in stride-to-stride fluctuations," Human Movement Science 24 (1) 97-115 (2005).

G S Berns, M L Hull, H A Patterson, "Strain in the anteromedial bundle of the anterior cruciate ligament under combination loading," J of Orthopaedic Research 10 (2) 167-176 (February 2005).

T Krosshaug, T E Anderson, O-E Olsen, G Myklebust, R Bahr, "Research approaches to describe the mechanisms of injuries in sport: limitations and possibilities," Br J Sports Med 39, pg 330-339 (Feb. 27, 2005).

B J West, N Scafetta, "A multifractal dynamic model of human gait," Fractals in Bio & Med, Birk. Basel (May 2006), pg 131-140 (2005).

T J Withrow, L J Huston, E M Wojtys, J A Ashton-Miller, "The relationship between quadriceps muscle force, knee flexion, and anterior cruciate ligament strain in an in vitro simulated jump landing," AOSSM $31^{st}$ Meeting, Keystone Colo., (July 2005); published in Am J Sports Med 34 (2) 269-274 (February 2006).

V P Ivanenko, G Cappellini, R E Popple, F Lacquaniti, "Coordination of locomotion with voluntary movements in humans," J of Neuroscience 25 (31) 7238-7352 (August 2005).

C Toulotte, A Thevenon, E Watelain, C Fabre, "Identification of healthy and elderly fallers and non-fallers by gait analysis under dual-task conditions," Clinical Rehabilitation 20 (3) 269-276 (2006).

M G Bowden, C K Balasubramanian, R R Neptune, S A Katz, "Anterior-posterior ground reaction forces as a measure of paretic leg contribution in hemiparetic walking," Stroke 37 pg 872-876 (March 2006).

G Brambilla, J Buchi, A J Ijspeert, "Adaptive four legged locomotion control based on nonlinear dynamical systems," Proceedings $9^{th}$ Int Conf on the Simulation of Adaptive Behavior (SAB 2006), pg 1-12 (Preprint May 2006).

H Geyer, A Seyfarth, R Blickhan, "Compliant leg behavior explains basic dynamics of walking and running," Royal Soc. Proceedings B, pg 1-7 (June 2006).

L L Nuffer, P M Medvick, H P Foote, J C Solinsky, "Multi-/Hyper-Spectral Image Enhancement for Biological Cell Analysis," Cytometry, Part A 69A (8) 897-903 (Aug. 1, 2006).

W Wang, R Crompton, A Minetti, M Gunther, W Sellers, R Abboud, R M Alexander, "A muscle-driven model of human walking and estimate of metabolic expenditure on muscles," J of Biomechanics 39 (1) S36 (Aug. 25, 2006).

S D Glassman, K Bridwell, J R Dimar, W Horton, S Berven, F Schwab, "The impact of positive sagittal balance in adult spinal deformity," Spine 30 (18) 2024-2029 (September 2006).

A Hreljac, R T Imamura, R F Escamilla, W B Edwards, "When does a gait transition occur during human locomotion," J of Sports Science and Med 6, pg 36-43 (2007).

N Scafetta, R E Moon, B J West, "Fractal response of physiological signals to stress conditions, environmental changes, and neurodegenerative diseases," COMPLEXITY, Wiley Interscience, 12 (5) 12-17 (2007).

S Mallau, G Bollini, JL Jouve, C Assiante, "Locomotor skills and balance strategies in adolescents idiopathic scoliosis," Spine 32 (1) E14-E22 (January 2007).

U van Daele, F Hagman, S Truijen, P Vorlat, B van Gheluwe, P Vaes, "Differences in balance strategies between non-specific chronic low back pain patients and healthy control subjects during unstable sitting," Spine 34 (11) 1233-1238 (May 2007).

A A Biewener, M A Daley, "Unsteady motion: integrating muscle function with the whole body dynamics and neuromuscular control," J Exp Biology 210, pg 2949-2960 (Jun. 12, 2007).

D Saha, S Gard, S Fatone, S Ondra, "The effect of trunk-flexed postures on balance and metabolic energy expenditure during standing," Biomechanics 32 (15) 1605-1611 (July 2007).

G Scivoletto, A Romanelli, A Mariotti, D Marinucci, F Tamburella, A Mammone, E Cosentino, S Sterzi, M Molinari, "Clinical factors that affect walking level and performance in chronic spinal cord lesion patients," Spine 33 (3) 259-264 (February 2008).

K J Parsons, T Pafau, A M Wilson, "High-speed gallop locomotion in the thoroughbred racehorse I. The effect of incline on stride parameters," J of Exp Biology 211 pg 935-944 (February 2008). See also, K Phillips (<kathryn@biologists.com>), "How horses gallop up hill," http://jeb.biologist.org/cgi/content/full/211/6/ii (2008).

K J Parsons, T Pafau, A M Wilson, "High-speed gallop locomotion in the thoroughbred racehorse. II. The effect of incline on center of mass movement and mechanical energy fluctuation," J of Exp Biology 211 pg 945-956 (February 2008a).

C H Cheung, K H Lin, J L Wang, "Co-contraction of cervical muscles during Sagittal and coronal neck motions at different movement speeds," Eur J Appl Physiol 103 (6) 647-654 (August 2008).

M A McDowell, C D Fryar, C L Ogden, K M Flegal, "Anthropometric Reference Data for Children and Adults, 2003-2006," CDC National Health Statistics Reports (10) (Oct. 22, 2008).

R R Neptune, D J Clark, S A Kautz, "Modular control of human walking: a simulation study," J Biomechanics 42 (9) 1282-1287 (2009).

C K Balasubramanian, R R Neptune, S A Kautz, "Variability in spatiotemporal step characteristics and its relationship to walking performance post stroke," Gait & Posture 29, pg 408-414 (2009).

R R Neptune, C P McGowan, S A Kautz, "Forward Dynamics Simulations Provide Insight Into Muscle Mechanical Work During Human Locomotion," Exercise Sports Sci Rev 37 (4) 203-210 (2009b).

D R Wilderman, S E Ross, D A Padua, "Thigh muscle activity, knee motion, and impact force during side-step pivoting, in agility trained female basketball players," J Athletic Training 44 (1) 14-25 (February 2009).

B Chuckpaiwong, J A Nunley, R M Queen, "Correlation between static foot type measurements and clinical assessments," Foot Ankle Int. 30 (3) 205-212 (March 2009).

A P Claus, J A Hides, G L Moseley, P W Hodges, "Different ways to balance the spine: Subtle changes in Sagittal spinal curves affect regional muscle activity," Spine 34 (6) E208-E214 (March 2009).

K M Brown, D E Bursey, L J Arneson, C A Andrews, P M Ludewig, W M Glasoe, "Consideration for digitization precision when building coordinate axes for a foot model," J BioMech 42 (19) 1263-1269 (April 2009).

N Scafetta, D Marchi, B J West, "Understanding the complexity of human gait dynamics," CHAOS 19 (026108), pg 1-20 (May 2009).

S Gillain, E Warzee, F Lekeu, V Wojtasik, D Maquet, JL Croisier, E Salmon, J Petermans, "The value of instrumental gait analysis in the elderly healthy, MCI or Alzheimer's disease subjects and a comparison with other clinical tests used in single and dual-task conditions," Ann Phys Rehabil Med 52 (6) 453-474 (May 2009).

C Enzinger, H Dawes, H Johansen-Berg, D Wade, M Bogdanovic, J Collett, C Guy, U Kischka, S Ropele, F Frazekas, PM Matthews, "Brain activity changes associated with treadmill training after stroke," Stroke 40 pg 2460-2467 (July 2009).

J Chappell, D Kirkendall, C Giuliani, B Yu, W E Garrett, "Kinematics and EMG landing preparation in vertical stop-jumps: Risks for non-contact ACL injury," AJSM__20060510_BYU.doc, Preprint (received December 2009).

W E Garrett, B Yu, "Chapter 10: Congruence between existing prevention programs and research on risk factors and mechanisms of non-contact ACL injury," Chapter__10_Injury_mechanism_Risk_Factors_training_Program.doc, Preprint (received December 2009).

W E Garrett, B Yu, "Mechanisms of Non-Contact ACL Injuries," Garrett ACL mechanism.doc, Preprint (received December 2009b).

R M Kiss, "Comparison between kinematic and ground reaction force techniques for determining gait events during treadmill walking at different speeds," Med Eng and Physics (in press March 2010).

C B Beaman, C L Peterson, R R Neptune, S A Kautz, "Differences in self-selected and fast-comfortable walking in post-stroke hemiparetic persons," Gait & Posture 31 311-316 (2010).

L Olson, http://olympics.fanhouse.com/2010/02/17/star-crossed-in-snowboard-cross/(2010).

Q-angle1 http://www.healthexpertadvice.org/medical_dictionary/index.php?I=Q (2010).

Q-angle2 http://nbata.com/EducationResearch/GlossaryofTerms/Knee/tabid/1619/Default.aspx (2010).

Q-angle3 http://www.womens-weight-training-programs.com/weighttrainingterms.html (2010).

Energy1 http://en.wikipedia.org/wiki/Kinetic_energy (2010).

Energy2 http://en.wikipedia.org/wiki/Principle_of_least_action (2010).
Answers1 http://www.answers.com/topis/lower-limb (2010).
Answers2 http://www.answers.com/topic/lower-limb#Muscles (2010).
Gray432 http://en.wikipedia.org/wiki/File:Gray432_color.png (2010).
Gray440 http://en.wikipedia.org/wiki/File:Gray440_color.png, (2010).
Anatomy http://fitstep.com/Advanced/Anatomy (2010).
Anatomy2 http://en.wikipedia.org/wiki/Anatomical_terms_of_motion (2010).
Biosyn Systems http://biosynsystems.com (2010).
Mathiyakom http://www.usc.edu/dept/LAS/kinesiology/exsc301/LabManual/Introduction.pdf (2010).
Locomotion http://www.univie.ac.at/cga/courses/be522/tsp.html (2010).
Stride http://moon.ouhsc.edu/dthompso/gait/knmatics/stride.htm (2010).
McNicholas http://www.mcnicholaskneeclinic.co.uk/pdfs/aclreconstruction.pdf (2010).
Performance_Corps http://www.performancecorps.com/Performance_Corps/Articles.html (2010).
Polhemus http://www.polhemus.com/polhemus_editor/assets/USOCWeightLiftingElbow.pdf (2010).
Polhemus2 http://www.polhemus.com/?page=Motion_Case_Studies_AMM (2010).
Automatics http://automaticswingtrainer.com/ (2010).
Ascension-tech http://ascension-tech.com (2010).
Baker http://www.brainandspinalcord.org/blog/2010/01/21/physical-exercise-a-panacea-for-body-and-brain/ (2010).
SOAR http://www.soarmedical.com/ (2010).

The contents of each of the above-identified documents is incorporated herein in its entirety. The identification of a document in the above list is not an admission that the document constitutes prior art to the subject patent application.

While this application describes certain examples, it is to be understood that the systems and methods described herein are not limited to these examples, but on the contrary, and are intended to encompass various modifications and equivalent arrangements included within the spirit and scope of the appended claims.

I claim:

1. A method of determining mammal locomotion metrics using first and second sensor bands, each sensor band respectively attached to one of paired limbs of a mammal and comprising a first sensor for sensing muscle circumferential pressure and providing pressure data based thereon, a second sensor for sensing gravity and providing gravity data based thereon and a third sensor for sensing a magnetic field and providing magnetic field data based thereon, the method comprising:
    collecting pressure data, gravity data and magnetic field data from the first, second and third sensors of the first and second sensor bands;
    correlating the collected data in time to determine take-off and touch-down transitions surrounding swing events of the limbs; and
    determining aspects of linear momentum and angular momentum associated with motions of the paired limbs based on the determined take-off and touch-down transitions.

2. The method according to claim 1, wherein the take-off and touch-down are determined by separating periodic and aperiodic motions.

3. A system for determining mammal locomotion metrics, the system comprising:
    a first pair of sensor bands, each sensor band of the pair of sensor bands configured for attachment to a respective one of paired limbs of a mammal and comprising a first sensor for sensing muscle circumferential pressure and providing pressure data based thereon, a second sensor for sensing gravity and providing gravity data based thereon and a third sensor for sensing a magnetic field and providing magnetic field data based thereon; and
    processing circuitry for receiving the pressure data, the gravity data and the magnetic field data from the sensor bands when the sensor bands are attached to the limbs of the mammal, correlating the received data in time to determine take-off and touch-down transitions surrounding swing events of the limbs, and for determining aspects of linear momentum and angular momentum associated with motions of the paired limbs based on the determined take-off and touch-down transitions.

4. The system according to claim 3, further comprising a second pair of sensor bands, each sensor band of the second pair of sensor bands configured for respective attachment to one of the paired limbs of the mammal and comprising a first sensor for sensing muscle circumferential pressure and providing pressure data based thereon, a second sensor for sensing gravity and providing gravity data based thereon and a third sensor for sensing a magnetic field and providing magnetic field data based thereon, wherein the processing circuitry further receives the pressure data, the gravity data and the magnetic field data from the second pair of sensor bands and uses the second pair sensor band data in the correlating to determine take-off and touch-down transitions and the determining of the aspects of linear momentum and angular momentum associated with motions of the paired limbs.

5. A system for measuring track and balance motion comprising:
    plural first sensor bands each configured for attachment to a respective calves of a mammal and providing first track and balance-related data;
    processing circuitry for receiving the first track and balance-related data from the sensor bands when the sensor bands are attached to the calves of the mammal and for estimating track and balance metrics across multiple gait cycles based on the received first track and balance-related data;
    plural second sensor bands each configured for attachment to a respective thigh of the mammal and providing second track and balance-related data, wherein the second track and balance-related data is used in the estimating of track and balance metrics across multiple gait cycles; and
    plural third sensor bands configured for attachment to upper limbs of the mammal and providing third track and balance-related data, wherein the third track and balance-related data is used in the estimating of track and balance metrics across multiple gait cycles.

* * * * *